(12) United States Patent
Bae

(10) Patent No.: US 7,919,576 B2
(45) Date of Patent: *Apr. 5, 2011

(54) IMMUNOGENIC CD19 PEPTIDES

(75) Inventor: Joo-eun Bae, Norwood, MA (US)

(73) Assignee: Rush University Medical Center, Chicago, IL (US)

( * ) Notice: Subject to any disclaimer, the term of this patent is extended or adjusted under 35 U.S.C. 154(b) by 75 days.

This patent is subject to a terminal disclaimer.

(21) Appl. No.: 12/206,394

(22) Filed: Sep. 8, 2008

(65) Prior Publication Data

US 2009/0068235 A1 Mar. 12, 2009

Related U.S. Application Data

(62) Division of application No. 10/884,862, filed on Jul. 2, 2004, now Pat. No. 7,812,116.

(60) Provisional application No. 60/484,689, filed on Jul. 3, 2003.

(51) Int. Cl.
    *C07K 5/00* (2006.01)
    *A61K 39/00* (2006.01)

(52) U.S. Cl. ............................ 530/300; 424/184.1; 514/2

(58) Field of Classification Search ........................ None
    See application file for complete search history.

(56) References Cited

U.S. PATENT DOCUMENTS

| | | | |
|---|---|---|---|
| 4,603,112 A | 7/1986 | Paoletti et al. |
| 4,769,330 A | 9/1988 | Paoletti et al. |
| 4,777,127 A | 10/1988 | Suni et al. |
| 5,017,487 A | 5/1991 | Stunnenberg et al. |
| 5,108,921 A | 4/1992 | Low et al. |
| 5,939,526 A | 8/1999 | Gaugler et al. |
| 6,271,019 B1 | 8/2001 | Van Baren et al. |
| 6,291,430 B1 | 9/2001 | Chaux et al. |
| 6,306,640 B1 | 10/2001 | Nicolette |
| 6,344,203 B1 | 2/2002 | Sandrin et al. |
| 6,440,386 B1 | 8/2002 | Leung et al. |
| 2003/0206916 A1* | 11/2003 | Bae et al. .................. 424/185.1 |

FOREIGN PATENT DOCUMENTS

| | | |
|---|---|---|
| EP | 0345242 | 12/1989 |
| GB | 2200651 | 8/1988 |
| WO | WO 89/01973 | 3/1989 |
| WO | WO 90/11092 | 10/1990 |
| WO | WO 91/02805 | 3/1991 |

OTHER PUBLICATIONS

Harig et al, Blood, vol. 98, p. 2999-3005, 2001.*
Tedder et al , J Immunol vol. 143, p. 712-717, 1989.*
Algino et al., "CD20 (pan-B cell antigen) expression on bone marrow-derived cells" *Am J Clin Pathol* 106(1):78-81, Jul. 1996 (abstract).
Altman JD et al, "Phenotypic analysis of antigen-specific T lymphocytes" *Science* 274:94-96, 1996 (abstract).
Bakker et al, "Generation of antimelanoma cytotoxic T lymphocytes from healthy donors after presentation of melanoma-associated antigen-derived epitopes by dendritic cells in vitro" *Cancer Res* 55: 5330-5334, 1995 (abstract).
Baur MP et al., "Genetic analysis of IDDM: the GAW5 multiplex family dataset" *Genet Epidemiol* 6: 15-20, 1989 (abstract).
Beatty GL et al., "Regulation of tumor growth by IFN-gamma in cancer immunotherapy" *Immunol Res* 24: 201-210, 2001 (abstract).
Bejcek et al., "Development and characterization of three recombinant single chain antibody fragments (scFvs) directed against ehe CD19 antigen" *Cancer Res* 55 (11): 2346-2351, 1995 (abstract).
Berkner, "Development of adenovirus vectors for the expression of heterologous genes" *Biotechniques* 6: 616-627, 1988.
Bordignon, "Retroviral vector-mediated high-efficiency expression of adenosine deminase (ADA) in hematopoietic long-term cultures of ADA-deficient marrow cells" *Proc Natl Acad Sci USA* 86: 6748-52, 1989.
Brossart P et al., "Selective activation of Fas/Fas ligand-mediated bytotoxicity by a self peptide" *J Exp Med* 183: 2449-2458, 1996 (abstract).
Chen et al.," Human papillomavirus type 16 nucleoprotein E7 is a tumor rejection antigen" *Proc Natl Acad Sci USA* 88: 110-114, 1991 (abstract).
Correll et al., "Production of human glucocerebrosidase in mice after retrovira gene transfer into multipotential hematopoietic progenitor cells" *Proc Natl Aced Sci USA* 86, p. 8912, 1989 (abstract).
Coulie et al., "Antigens recognized on human tumors by cytolytic T lymphocytes: towards vaccination?" *Stem Cells* 13: 393-403, 1995 (abstract).
Culver K, "Lymphocytes as cellular vehicles for gene therapy in mouse and man" Proc Natl Acad Sci USA 88, p. 3155, 1991.
Dörken et al., "Leucocyte Typing IV: White Cell Differentiation Antigens," In: Knapp W., Dörken B, Gilks WR et al., eds. Leucocyte Typing IV: *White Cell Differentiation Antigens*. Oxford: Oxford University Press: 46-48, 1989.
Einfeld et al.," Molecular cloning of the human B cell CD20 receptor predicts a hydrophobic protein with multiple transmembrane domains" *EMBO J* 7 (3): 711-717, 1988 (abstract).
Fisher-Hoch et al, "Protection of rhesus monkeys from fatal Lassa fever by vaccination with a recombinant vaccinia virus containing the Lassa virus glycoprotein gene" *Proc Natl Acad Sci* 86: 317-321, 1989 (abstract).
Flexner et al., "Vaccinia virus expression vectors" *Ann NY Acad Sci* 569: 86-103, 1989.
Flexner et al., "Attenuation and immunogenicity in primates of vaccinia virus recombinants expressing human interleukin-2" *Vaccine* 8: 17-21, 1990 (abstract).
Freeman et al, Cloning of B7-2: a CTLA-4 counter-receptor that costimulates human T cell proliferation *Science* 262: 909-991, 1993 (abstract).
Gajewski et al., "Immunization of HLA-A2+ melanoma patients with MAGE-3 or MelanA peptide-pulsed autologous PlMC plus rhIL-12" *Clin Cancer Res* 7, p. 895, 2001.

(Continued)

*Primary Examiner* — Misook Yu
*Assistant Examiner* — Lei Yao
(74) *Attorney, Agent, or Firm* — Foley & Lardner LLP

(57) ABSTRACT

The invention provides relatively short immunogenic peptides derived from CD19 antigens, and biologically active variants thereof, which elicit an immune response. Nucleic acids encoding the immunogenic peptides and antibodies specific for the peptides are also provided. The immunogenic peptides can be included in pharmaceutical compositions, such as cancer vaccines, and used for the treatment of cancer.

4 Claims, 7 Drawing Sheets

OTHER PUBLICATIONS

*Gene Expression Technology*, Goeddel ed., Academic Press, Inc., 1991.

Gomez-Nunez et al., "Peptide binding motif predictive algorithms correspond with experimental binding of leukemia vaccine candidate peptides to HLA-A *0201 molecules," *Leukemia Research* 30 (2006), 1293-1298.

Greenberg J, "Therapy of murine leukemia with cyclophosphamide and immune Lyt-2+ cells: cytolytic T cells can mediate eradication of disseminated leukemia" *Immunol* 136 (5), p. 1917, 1986 (abstract).

Grube, M et al., "Are Normally Expressed B-Cell Differentiation Antigens Possible Target Antigens for Cellular Immunotherapy in B-Cell Malignancies?" Abstracts of the 44th Annual Meeting of the Amer Soc of Hematology, Philadelphia, Dec. 2002.

Grube, M et al., "Autoreactive, cytotoxic T lymphocytes specific for peptides derived from normal B-cell differentiation antigens in healthy individuals and patients with B-cell malignancies," *Clin Cancer Res* 10 (3): 1047-1056, 2004.

Guzman et al., "Efficient and selective adenovirus-mediated gene transfer into vascular neointima" *Circulation* 88: 2838-2848, 1993 (abstract).

Guzman et al., "Efficient gene transfer into myocardium by direct injection of adenovirus vectors" *Cir Res* 73: 1202-1207, 1993 (abstract).

H.G. Rammensee et al., MHC Ligands and Peptide Motifs, Landes *Bioscience*, 1997.

Hall, "IL-12 at the crossroads" Science 268: 1432-1434, 1995.

Harper et al., *J of Immunology* 147:1037-1044 and NCBI accession No. 2134978, 1991.

Hassainya, Y. et al "Identification of Naturally Processed HLA-A2— Restricted Proinsulin Epitopes by Reverse Immunology," *Diabetes*, vol. 54, Jul. 2005; published by American Diabetes Association.

Herlyn et al., "Anti-idiotypic antibodies bear the internal image of a human tumor antigen" *Science* 232, p. 100, 1986 (abstract).

Hoojberg et al., *J Immunother Emphais Tumor Immunol* Suppl 2:43-45, 1996.

Hopp et al., "A short polypeptide marker sequence useful for recombinant protein and purification" *BioTechnology* 6, p. 1204, 1988.

Houbiers JG et al, "In vitro induction of human cytotoxic T lymphocyte responses against peptides of mutant and wild-type p53" *Eur J Immunol* 23: 2072-2077, 1993 (abstract).

Hultin et al., "CD20 (pan-B cell) antigen is expressed at a low level on a subpopulation of human T lymphocytes" *Cytometry* 14: 196-204, 1993 (abstract).

Ikeda H et al., "The roles of IFN gamma in protection against tumor development and cancer immunoediting" *Cytokine Growth Factor Rev* 13: 95-109, 2002 (abstract).

Kass-Eisler et al., "Quantitative determination of adenovirus-mediated gene delivery to rat cardiac myocytes in vitro and in vivo" *Proc Natl Acad Sci* 90: 11498-11502, 1993 (abstract).

Kast et al., "Eradicaton of adenovirus E1-induced tumors by E1A-specific cytotoxic T lymphocytes" *Cell* 59: 603-614, 1989.

Kolls et al., "Prolonged and effective blockade of tumor necrosis factor activity through adenovirus-mediated gene transfer" *Proc Natl Acad Sci* 91: 215-219, 1994 (abstract).

Lau et al., "Phase I trial of intravenous peptide-pulsed dendritic cells in patients with metastatic melanoma" *J Immun* 24 (1), p. 66, 2001 (abstract).

Liu et al, "A BsmFI PCR/RFLP in the canine CD19 gene" *Anim Genet* 29(1): 64-65, 1998.

Lodge et al., "Dendritic cell-based immunotherapy of prostate cancer: immune monitoring of a phase II clinical trial" *Cancer Res* 60, p. 829, 2000.

Loken et al., "Flow cytometric analysis of human bone marrow. II. Normal B lymphocyte developments" *Blood* 70: 1316-1324, 1987 (abstract).

Lynch et al., "Immunotherapeutic elimination of syngeneic tumors in vivo by cytotoxic T lymphocytes generated in vitro from lymphocytes from the draining lymph nodes of tumor-bearing mice" *Eur J Immunol* 21: 1403-1410, 1991 (abstract).

Macardle et al., "CD20" *J Bio. Regul Homeost Agents* 16 (2): 136-138, 2002, (mus musculus).

Miller A D et al., "Improved retroviral vectors for gene transfer and expression" *BioTechniques* 7: 980-990, 1989 (abstract).

Mishra, S. et al., "Prediction and molecular modeling of T-cell epitopes derived from placental alkaline phosphatase for use in cancer immunotherapy," *J. Biomol. Struct. Dyn.*, Oct. 2006; 24(2): 109-21 (Abstract only).

Molecular Cloning: *A Laboratory Manual*, J. Sambrook et al., eds., Second Edition, Cold Spring Harbor Laboratory Press, Cold Spring Harbor, N.Y., 1989.

Morse et al., "A Phase I study of active immunotherapy with carcinoembryonic antigen peptide (CAP-1)-pulsed, autologous human cultured dendritic cells in patients with metastatic malignancies expressing carcinoembryonic antigen" *Clin Cancer Res* 5, p. 1331, 1999 (abstract).

Nabavi et al., "Signalling through the MHC class II cytoplasmic domain is required for antigen presentation and induces B7 expression" *Nature* 360, p. 266, 1992 (abstract).

Nachman et al., "Pseudodipeptie analogs of the pyrokinin/PBAN (FXPRLa) insect neuropeptide family containing carrbocyclic Pro-mimetic conformational components" *Regul Pept* 57: 359-370, 1995 (abstract).

Nestle et al., *Amer J of Path* 150:641-651, 1997.

Nijman HW et al., "Identification of peptide sequences that potentially trigger HLA-A2.1-restricted cytotoxic T lymphocytes" *Eur J Immunol* 23: 1215-1219, 1993.

Otero et al., "CD19 function in early and late B cell development: I. Maintenance of follicular and marginal zone B cells requires CD19-dependent survival signals" *J Immunol* 170(1):73-83, 2003 (abstract).

Porgador A et al., "Bone marrow-generated dendritic cells pulsed with a class I-restricted peptide are potent inducers of cytotoxic T lymphocytes" *J Exp Med* 182:255-260, 1995 (abstract).

Riddle et al., "Restoration of Viral Immunity in Immunodeficient Humans by the Adoptive Transfer of T Cell Clones,:" Science 257, p. 238-241, 1992.

Rill D R, "An approach for the analysis of relapse and marrow reconstitution after autologous marrow transplantation using retrovirus-mediated gene transfer" *Blood* 79 (10):2694-2700, 1991 (abstract).

Roberts et al., "Vaccination with CD20 peptides induces a biologically active, specific immune response in mice" *Blood* 99 (10):3748-3755, 2002 (abstract).

Roberts et al., "Vaccination with CD20 peptides induces a biologically active, specific immune response in mice," *Blood* 99 (10):3748-3755, 2002.

Romani N et al., "Proliferating dendritic cell progenitors in human blood" *J Exp Med* 180:83-89, 1994.

Rosenfeld et al, "Adenovirus-mediated transfer of a recombinant alpha 1-antitrypsin gene to the lung epithelium in vivo" *Science* 252:431-434, 1991 (abstract).

Salter et al., "Impaired assembly and transport of HLA-A and -B antigens in a mutant TxB cell hybrid" *EMBO J* 5:943-949, 1986.

Scheuermann et al,"CD 19 antigen in leukemia and lymphoma diagnosis and immunotherapy" *Leuk Lymphoma* 18(5-6):385-397, 1995 (abstract).

Schmidt et al., "Cell-free tumor antigen peptide-based cancer vaccines" *Proc Natl Acad Sci* 94, p. 3262, 1997 (abstract).

Sciarra and Cutie, "Aerosols," in *Remington's Pharmaceutical Sciences*, 18th edition, Gennaro et al:1694-1712, 1990.

Spira et al., "The identification of monoclonal class switch variants by sib selection and an ELISA assay" *J Immunol Methods* 74, p. 307, 1984 (abstract).

Stamenkovic et al., "Analysis of two cDNA clones encoding the B lymphocyte antigen CD20 (B1, Bp35), a type III integral membrane protein" *J Exp Med* 167 (6):1975-1980, 1988 (abstract).

Stamenkovic et al, "CD19, the earliest differentiation antigen of the B cell lineage, bears three extra cellular immunoglobulin-like domains and an Epstein-Barr virus-related cytoplasmic tail" *J Exp Med* 168:1205-1210, 1988 (abstract).

Steinman AM, "The dendritic cell system and its role in immunogenicity" *Annu Rev Immunol* 9:271-296, 1991 (abstract).

Steplewski et al., "Isolation and characterization of anti-monosialoganglioside monoclonal antibody 19-9 class-switch variants" *Proc Natl Acad Sci* 82, p. 8653, 1985 (abstract).

Strausberg et al., "Generation and initial analysis of more than 15,000 full-length human and mouse cDNA sequences" *Proc Natl Acad Sci USA* 99 (26):16899-16903, 2002 (abstract).

Sun et al., "Cloning, sequencing and expression of swine CD19" http://www.ncbi.nlm.nih.gov/entrez/query.fcgi?cmd=Retrieve&db=protein&list_uids=18496846&dopt=GenPept, 2002.

Tanaka et al., "Intratumoral injection of dendritic cells after treatment of anticancer drugs induces tumor-specific antitumor effect in vivo" *Int J Cancer* 101, p. 265, 2002 (abstract).

Tedder et al., Structure of the gene encoding the human B lymphocyte differentiation antigen CD20 (B1) *J Immunol* 142 (7):2560-2568, 1989 (abstract).

Tedder et al., "Isolation and structure of a cDNA encoding the B1 (CD20) cell-surface antigen of human B lymphocytes" *Proc Natl Acad Sci USA* 85 (1):208-212, 1988 (abstract).

Tedder et al., "Isolation of cDNAs encoding the CD19 antigen of human and mouse B lymphocytes. A new member of the immunoglobulin superfamily" *J Immunol* 143:712-717, 1989 (abstract).

Tedder et al., "The CD19/CD21 signal transduction complex of B lymphocytes" *Immunol Today* 15, p. 437, 1994 (abstract).

Tomb et al., *Nature* 388:539-543 and NCBI accession No. 7464360, 1997.

Tourdot et al., "A general strategy to enhance immunogenicity of low-affinity HLA-A2. 1-associated peptides:implication in the identification of cryptic tumor epitopes" *Eur J Immunol* 30:3411-3421, 2000.

Tulpule et al., "Anti-B4 (CD 19) monoclonal antibody, conjugated with ricin (B4-blocked ricin: B4bR) in refractory AIDS-lymphoma" *Proc Ann Meet Am Soc Clin Oncol* 13, p. A10, 1994 (abstract).

Ulmer et al., "Heterologous protection against influenza by injection of DNA encoding a viral protein" *Science* 259:1745-1748, 1993 (abstract).

Ulmer et al., "Heterologous protection against influenza by injection of DNA encoding a viral protein" Science 259:1745-1749, 1993, reviewed by Cohen, *Science* 259:1691-1692, 1993.

Van den Eynde & Brichard, :New tumor antigens recognized by T cells *Curr Opin Immunol* 7:674-681, 1995 (abstract).

Vectors: *Essential Data Series*, Gacesa and Ramji, eds, John Wiley & Sons, NY, 1994.

Young et al., "The B7/BB1 antigen provides one of several costimulatory signals for the activation of CD4+ T Lymphocytes by human blood dendritic cells in vitro" *J Clin Invest* 90, p. 229, 1992 (abstract).

Zhou et al., "Structure and domain organization of the CD19 antigen of human, mouse, and guinea pig B lymphocytes. Conservation of the extensive cytoplasmic domain" *J Immunol* 147(4):1424-1432, 1991 (abstract).

Zhou et al., Structure of the genes encoding the CD19 antigen of human and mouse B lymphocytes: *Immunogenetics* 35(2):102-111, 1992 (abstract).

Zitvogel L et al., "Therapy of murine tumors with tumor peptide-pulsed dendritic cells: dependence on T cells, B7 costimulation, and T helper cell 1-associated cytokines" *J Exp Med* 183:87-97, 1996 (abstract).

Zweerink HJ et al., "Presentation of endogenous peptides to MHC class 1-restricted cytotoxic T lymphocytes in transport deletion mutant T2 cells" *J Immunol* 150:1763-1771, 1993.

* cited by examiner

Generation of CD20 peptide-specific CTLs

Cytotoxic activity of CD19 peptide-specific CTLs to ST486 (Burkett's lymphoma cell line)

Cytotoxic activity of CD20 peptide- specific CTLs to ST486 (Burkett's lymphoma cell line)

Cytotoxic activity of CD20 peptide- specific CTLs to IFN-γ/TNF-α treated ST486 (Burkett's lymphoma cell line)

Expansion of CD20 peptide-specific CTLs using CD3/CD28 beads and IL-2

Cytotoxic activity of expanded CD20 peptide-specific CTLs to ST486 (Burkett's lymphoma cell line)

SEQUENCE LISTING

```
<160> NUMBER OF SEQ ID NOS: 328

<210> SEQ ID NO 1
<211> LENGTH: 9
<212> TYPE: PRT
<213> ORGANISM: Homo sapiens

<400> SEQUENCE: 1

Arg Leu Leu Phe Phe Leu Leu Phe Leu
1               5

<210> SEQ ID NO 2
<211> LENGTH: 9
<212> TYPE: PRT
<213> ORGANISM: Homo sapiens

<400> SEQUENCE: 2

Thr Leu Ala Tyr Leu Ile Phe Cys Leu
1               5

<210> SEQ ID NO 3
<211> LENGTH: 9
<212> TYPE: PRT
<213> ORGANISM: Homo sapiens

<400> SEQUENCE: 3

Leu Leu Phe Leu Thr Pro Met Glu Val
1               5

<210> SEQ ID NO 4
<211> LENGTH: 9
<212> TYPE: PRT
<213> ORGANISM: Homo sapiens

<400> SEQUENCE: 4

Lys Leu Met Ser Pro Lys Leu Tyr Val
1               5

<210> SEQ ID NO 5
<211> LENGTH: 9
<212> TYPE: PRT
<213> ORGANISM: Homo sapiens

<400> SEQUENCE: 5

Leu Leu Phe Phe Leu Leu Phe Leu Val
1               5
```

<210> SEQ ID NO 6
<211> LENGTH: 9
<212> TYPE: PRT
<213> ORGANISM: Homo sapiens

<400> SEQUENCE: 6

Ser Leu Phe Leu Gly Ile Leu Ser Val
1               5

<210> SEQ ID NO 7
<211> LENGTH: 9
<212> TYPE: PRT
<213> ORGANISM: Homo sapiens

<400> SEQUENCE: 7

Ala Ile Ser Gly Met Ile Leu Ser Ile
1               5

<210> SEQ ID NO 8
<211> LENGTH: 9
<212> TYPE: PRT
<213> ORGANISM: Homo sapiens

<400> SEQUENCE: 8

Phe Ile Arg Ala His Thr Pro Tyr Ile
1               5

<210> SEQ ID NO 9
<211> LENGTH: 9
<212> TYPE: PRT
<213> ORGANISM: Homo sapiens

<400> SEQUENCE: 9

Ser Leu Asn Phe Ile Arg Ala His Thr
1               5

<210> SEQ ID NO 10
<211> LENGTH: 9
<212> TYPE: PRT
<213> ORGANISM: Homo sapiens

<400> SEQUENCE: 10

Leu Lys Met Glu Ser Leu Asn Phe Ile
1               5

<210> SEQ ID NO 11
<211> LENGTH: 9
<212> TYPE: PRT
<213> ORGANISM: Homo sapiens

<400> SEQUENCE: 11

Ser His Phe Leu Lys Met Glu Ser Leu
1               5

<210> SEQ ID NO 12
<211> LENGTH: 9
<212> TYPE: PRT
<213> ORGANISM: Homo sapiens

<400> SEQUENCE: 12

Tyr Leu Phe Leu Gly Ile Leu Ser Val
1               5

<210> SEQ ID NO 13

<211> LENGTH: 556
<212> TYPE: PRT
<213> ORGANISM: Homo sapiens

<400> SEQUENCE: 13

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400
```

```
Pro Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu His Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 14
<211> LENGTH: 297
<212> TYPE: PRT
<213> ORGANISM: Homo sapiens

<400> SEQUENCE: 14

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220
```

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
            245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Gly Pro Pro Gln Asp Gln Glu Ser
        275                 280                 285

Ser Pro Ile Glu Asn Asp Ser Ser Pro
    290                 295

<210> SEQ ID NO 15
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa is an anchor amino acid such as Leu or
      Ile
<220> FEATURE:
<221> NAME/KEY: MISC_FEATURE
<222> LOCATION: (3)..(8)
<223> OTHER INFORMATION: Xaa can be any amino acid

<400> SEQUENCE: 15

Xaa Xaa Xaa Xaa Xaa Xaa Xaa Xaa
1               5

<210> SEQ ID NO 16
<211> LENGTH: 9
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa is an anchor amino acid such as Val

<400> SEQUENCE: 16

Xaa Xaa Xaa Xaa Xaa Xaa Xaa Xaa Xaa
1               5

<210> SEQ ID NO 17
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa is an anchor amino acid such as Leu or
      Ile
<220> FEATURE:
<221> NAME/KEY: MISC_FEATURE
<222> LOCATION: (3)..(8)
<223> OTHER INFORMATION: Xaa can be any amino acid
<220> FEATURE:
<221> NAME/KEY: MISC_FEATURE
<222> LOCATION: (9)..(9)

<223> OTHER INFORMATION: Xaa is an anchor amino acid such as Val

<400> SEQUENCE: 17

Xaa Xaa Xaa Xaa Xaa Xaa Xaa Xaa Xaa
1               5

<210> SEQ ID NO 18
<211> LENGTH: 4
<212> TYPE: PRT
<213> ORGANISM: Homo sapiens

<400> SEQUENCE: 18

Leu Leu Phe Phe
1

<210> SEQ ID NO 19
<211> LENGTH: 4
<212> TYPE: PRT
<213> ORGANISM: Homo sapiens

<400> SEQUENCE: 19

Leu Leu Phe Leu
1

<210> SEQ ID NO 20
<211> LENGTH: 5
<212> TYPE: PRT
<213> ORGANISM: Homo sapiens

<400> SEQUENCE: 20

Phe Leu Leu Phe Leu
1               5

<210> SEQ ID NO 21
<211> LENGTH: 6
<212> TYPE: PRT
<213> ORGANISM: Homo sapiens

<400> SEQUENCE: 21

Phe Phe Leu Leu Phe Leu
1               5

<210> SEQ ID NO 22
<211> LENGTH: 6
<212> TYPE: PRT
<213> ORGANISM: Homo sapiens

<400> SEQUENCE: 22

Leu Leu Phe Phe Leu Leu
1               5

<210> SEQ ID NO 23
<211> LENGTH: 7
<212> TYPE: PRT
<213> ORGANISM: Homo sapiens

<400> SEQUENCE: 23

Leu Phe Phe Leu Leu Phe Leu
1               5

<210> SEQ ID NO 24
<211> LENGTH: 8
<212> TYPE: PRT
<213> ORGANISM: Homo sapiens

<400> SEQUENCE: 24

```
Leu Leu Phe Phe Leu Leu Phe Leu
1               5

<210> SEQ ID NO 25
<211> LENGTH: 4
<212> TYPE: PRT
<213> ORGANISM: Homo sapiens

<400> SEQUENCE: 25

Lys Met Glu Ser
1

<210> SEQ ID NO 26
<211> LENGTH: 4
<212> TYPE: PRT
<213> ORGANISM: Homo sapiens

<400> SEQUENCE: 26

Met Glu Ser Leu
1

<210> SEQ ID NO 27
<211> LENGTH: 5
<212> TYPE: PRT
<213> ORGANISM: Homo sapiens

<400> SEQUENCE: 27

Lys Met Glu Ser Leu
1               5

<210> SEQ ID NO 28
<211> LENGTH: 6
<212> TYPE: PRT
<213> ORGANISM: Homo sapiens

<400> SEQUENCE: 28

Leu Lys Met Glu Ser Leu
1               5

<210> SEQ ID NO 29
<211> LENGTH: 2096
<212> TYPE: DNA
<213> ORGANISM: Homo sapiens

<400> SEQUENCE: 29
gaattcctct gaccaccatg ccacctcctc gcctcctctt cttcctcctc ttcctcaccc     60
ccatggaagt caggcccgag gaacctctag tggtgaaggt ggaagaggga gataacgctg    120
tgctgcagtg cctcaagggg acctcagatg gccccactca gcagctgacc tggtctcggg    180
agtccccgct taaacccttc ttaaaactca gcctggggct gccaggcctg gaatccaca    240 tgaggccccct ggcatcctgg cttttcatct tcaacgtctc tcaacagatg ggggcttct    300 acctgtgcca gccggggccc ccctctgaga aggcctggca gcctggctgg acagtcaatg    360
tggagggcag cggggagctg ttccggtgga atgtttcgga cctaggtggc ctgggctgtg    420
gcctgaagaa caggtcctca gagggcccca gctccccttc cgggaagctc atgagcccca    480
agctgtatgt gtgggccaaa gaccgccctg agatctggga gggagagcct ccgtgtgtcc    540
caccgaggga cagcctgaac cagagcctca gccaggacct caccatggcc cctggctcca    600
cactctggct gtcctgtggg gtaccccctg actctgtgtc caggggcccc ctctcctgga    660
cccatgtgca ccccaagggg cctaagtcat tgctgagcct agagctgaag gacgatcgcc    720
```

-continued

| | |
|---|---|
| cggccagaga tatgtgggta atggagacgg gtctgttgtt gccccgggcc acagctcaag | 780 |
| acgctggaaa gtattattgt caccgtggca acctgaccat gtcattccac ctggagatca | 840 |
| ctgctcggcc agtactatgg cactggctgc tgaggactgg tggctggaag gtctcagctg | 900 |
| tgactttggc ttatctgatc ttctgcctgt gttcccttgt gggcattctt catcttcaaa | 960 |
| gagccctggt cctgaggagg aaaagaaagc gaatgactga ccccaccagg agattcttca | 1020 |
| aagtgacgcc tcccccagga agcgggcccc agaaccagta cgggaacgtg ctgtctctcc | 1080 |
| ccacacccac ctcaggcctc ggacgcgccc agcgttgggc cgcaggcctg ggggcactg | 1140 |
| ccccgtctta tggaaacccg agcagcgacg tccaggcgga tggagccttg gggtcccgga | 1200 |
| gcccgccggg agtgggccca agaagagg aaggggaggg ctatgaggaa cctgacagtg | 1260 |
| aggaggactc cgagttctat gagaacgact ccaaccttgg gcaggaccag ctctcccagg | 1320 |
| atggcagcgg ctacgagaac cctgaggatg agccctgggt cctgaggat gaagactcct | 1380 |
| tctccaacgc tgagtcttat gagaacgagg atgaagagct gacccagccg gtcgccagga | 1440 |
| caatggactt cctgagccct catgggtcag cctgggaccc cagccgggaa gcaacctccc | 1500 |
| tggggtccca gtcctatgag gatatgagag gaatcctgta tgcagccccc cagctccact | 1560 |
| ccattcgggg ccagcctgga cccaatcatg aggaagatgc agactcttat gagaacatgg | 1620 |
| ataatcccga tggccagac ccagcctggg gaggaggggg ccgcatgggc acctggagca | 1680 |
| ccaggtgatc ctcaggtggc cagcctggat ctcctcaagt ccccaagatt cacacctgac | 1740 |
| tctgaaatct gaagacctcg agcagatgat gccaacctct ggagcaatgt tgcttaggat | 1800 |
| gtgtgcatgt gtgtaagtgt gtgtgtgtgt gtgtgtgtgt gtgtgtgtgt atacatgcca | 1860 |
| gtgacacttc cagtccccctt tgtattcctt aaataaactc aatgagctct tccaatccaa | 1920 |
| aaatgttaaa attagccagg catagttgtg tgtgcctaca gtgctacagg aggctgaggc | 1980 |
| aagaggattg cttgagttaa ggaaggaagt caaggctgca gtgagctatg gtcatgccac | 2040 |
| tgcactccag cctgggcaac agcaagaccc tgtgtccaaa aaaaaaaag gaattc | 2096 |

<210> SEQ ID NO 30
<211> LENGTH: 1474
<212> TYPE: DNA
<213> ORGANISM: Homo sapiens

<400> SEQUENCE: 30

| | |
|---|---|
| aaagacaaac tgcacccact gaactccgca gctagcatcc aaatcagccc ttgagatttg | 60 |
| aggccttgga gactcaggag ttttgagagc aaaatgacaa cacccagaaa ttcagtaaat | 120 |
| gggactttcc cggcagagcc aatgaaaggc cctattgcta tgcaatctgg tccaaaacca | 180 |
| ctcttcagga ggatgtcttc actggtgggc cccacgcaaa gcttcttcat gagggaatct | 240 |
| aagactttgg gggctgtcca gattatgaat gggctcttcc acattgccct gggggtctt | 300 |
| ctgatgatcc cagcagggat ctatgcaccc atctgtgtga ctgtgtggta ccctctctgg | 360 |
| ggaggcatta tgtatattat ttccggatca ctcctggcag caacggagaa aaactccagg | 420 |
| aagtgtttgg tcaaggaaa atgataatg aattcattga gcctctttgc tgccatttct | 480 |
| ggaatgattc tttcaatcat ggacatactt aatattaaaa tttcccatt tttaaaaatg | 540 |
| gagagtctga atttattag agctcacaca ccatatatta acatatacaa ctgtgaacca | 600 |
| gctaatccct ctgagaaaaa ctccccatct acccaatact gttacagcat acaatctctg | 660 |
| ttcttgggca ttttgtcagt gatgctgatc tttgccttct tccaggaact tgtaatagct | 720 |
| ggcatcgttg agaatgaatg gaaaagaacg tgctccagac ccaaatctaa catagttctc | 780 |

-continued

```
ctgtcagcag aagaaaaaaa agaacagact attgaaataa agaagaagt ggttgggcta       840
actgaaacat cttcccaacc aaagaatgaa gaagacattg aaattattcc aatccaagaa       900
gaggaagaag aagaaacaga gacgaacttt ccagaacctc cccaagatca ggaatcctca       960
ccaatagaaa atgacagctc tccttaagtg atttcttctg ttttctgttt ccttttttaa      1020
acattagtgt tcatagcttc aagagacat gctgactttc atttcttgag gtactctgca      1080
catacgcacc acatctctat ctggcctttg catggagtga ccatagctcc ttctctctta      1140
cattgaatgt agagaatgta gccattgtag cagcttgtgt tgtcacgctt cttcttttga      1200
gcaactttct tacactgaag aaaggcagaa tgagtgcttc agaatgtgat ttcctactaa      1260
cctgttcctt ggataggctt tttagtatag tatttttttt tgtcattttc tccatcagca      1320
accagggaga ctgcacctga tggaaaagat atatgactgc ttcatgacat tcctaaacta      1380
tcttttttttt attccacatc tacgttttttg gtggagtccc tttttatcat ccttaaaaca      1440
atgatgcaaa agggctttag agcacaatgg atct                                  1474
```

<210> SEQ ID NO 31
<211> LENGTH: 9
<212> TYPE: PRT
<213> ORGANISM: Homo sapiens

<400> SEQUENCE: 31

Gly Ile Leu Gly Phe Val Phe Thr Leu
1               5

<210> SEQ ID NO 32
<211> LENGTH: 9
<212> TYPE: PRT
<213> ORGANISM: Homo sapiens

<400> SEQUENCE: 32

Lys Leu Ser Leu Gly Leu Pro Gly Leu
1               5

<210> SEQ ID NO 33
<211> LENGTH: 9
<212> TYPE: PRT
<213> ORGANISM: Homo sapiens

<400> SEQUENCE: 33

Tyr Leu Ile Phe Cys Leu Cys Ser Leu
1               5

<210> SEQ ID NO 34
<211> LENGTH: 9
<212> TYPE: PRT
<213> ORGANISM: Homo sapiens

<400> SEQUENCE: 34

Leu Leu Arg Thr Gly Gly Trp Lys Val
1               5

<210> SEQ ID NO 35
<211> LENGTH: 9
<212> TYPE: PRT
<213> ORGANISM: Homo sapiens

<400> SEQUENCE: 35

Ser Leu Pro Thr Pro Thr Ser Gly Leu
1               5

```
<210> SEQ ID NO 36
<211> LENGTH: 9
<212> TYPE: PRT
<213> ORGANISM: Homo sapiens

<400> SEQUENCE: 36

Cys Leu Cys Ser Leu Val Gly Ile Leu
1               5

<210> SEQ ID NO 37
<211> LENGTH: 9
<212> TYPE: PRT
<213> ORGANISM: Homo sapiens

<400> SEQUENCE: 37

Tyr Ala Ala Pro Gln Leu His Ser Ile
1               5

<210> SEQ ID NO 38
<211> LENGTH: 9
<212> TYPE: PRT
<213> ORGANISM: Homo sapiens

<400> SEQUENCE: 38

Ile Leu His Leu Gln Arg Ala Leu Val
1               5

<210> SEQ ID NO 39
<211> LENGTH: 9
<212> TYPE: PRT
<213> ORGANISM: Homo sapiens

<400> SEQUENCE: 39

Ser Leu Gly Leu Pro Gly Leu Gly Ile
1               5

<210> SEQ ID NO 40
<211> LENGTH: 9
<212> TYPE: PRT
<213> ORGANISM: Homo sapiens

<400> SEQUENCE: 40

Asp Leu Gly Gly Leu Gly Cys Gly Leu
1               5

<210> SEQ ID NO 41
<211> LENGTH: 9
<212> TYPE: PRT
<213> ORGANISM: Homo sapiens

<400> SEQUENCE: 41

Gly Ile Leu His Leu Gln Arg Ala Leu
1               5

<210> SEQ ID NO 42
<211> LENGTH: 9
<212> TYPE: PRT
<213> ORGANISM: Homo sapiens

<400> SEQUENCE: 42

Gly Leu Leu Leu Pro Arg Ala Thr Ala
1               5

<210> SEQ ID NO 43
<211> LENGTH: 9
<212> TYPE: PRT
```

<213> ORGANISM: Homo sapiens

<400> SEQUENCE: 43

Leu Ile Phe Cys Leu Cys Ser Leu Val
1               5

<210> SEQ ID NO 44
<211> LENGTH: 9
<212> TYPE: PRT
<213> ORGANISM: Homo sapiens

<400> SEQUENCE: 44

Leu Leu Phe Phe Leu Leu Phe Leu Thr
1               5

<210> SEQ ID NO 45
<211> LENGTH: 9
<212> TYPE: PRT
<213> ORGANISM: Homo sapiens

<400> SEQUENCE: 45

Gly Leu Gly Ile His Met Arg Pro Leu
1               5

<210> SEQ ID NO 46
<211> LENGTH: 9
<212> TYPE: PRT
<213> ORGANISM: Homo sapiens

<400> SEQUENCE: 46

His Met Arg Pro Leu Ala Ser Trp Leu
1               5

<210> SEQ ID NO 47
<211> LENGTH: 9
<212> TYPE: PRT
<213> ORGANISM: Homo sapiens

<400> SEQUENCE: 47

Val Leu Trp His Trp Leu Leu Arg Thr
1               5

<210> SEQ ID NO 48
<211> LENGTH: 9
<212> TYPE: PRT
<213> ORGANISM: Homo sapiens

<400> SEQUENCE: 48

Gly Ile Leu Tyr Ala Ala Pro Gln Leu
1               5

<210> SEQ ID NO 49
<211> LENGTH: 9
<212> TYPE: PRT
<213> ORGANISM: Homo sapiens

<400> SEQUENCE: 49

Lys Val Glu Glu Gly Asp Asn Ala Val
1               5

<210> SEQ ID NO 50
<211> LENGTH: 9
<212> TYPE: PRT
<213> ORGANISM: Homo sapiens

<400> SEQUENCE: 50

Ser Leu Ser Gln Asp Leu Thr Met Ala
1               5

<210> SEQ ID NO 51
<211> LENGTH: 9
<212> TYPE: PRT
<213> ORGANISM: Homo sapiens

<400> SEQUENCE: 51

Leu Thr Met Ala Pro Gly Ser Thr Leu
1               5

<210> SEQ ID NO 52
<211> LENGTH: 9
<212> TYPE: PRT
<213> ORGANISM: Homo sapiens

<400> SEQUENCE: 52

Ser Thr Leu Trp Leu Ser Cys Gly Val
1               5

<210> SEQ ID NO 53
<211> LENGTH: 9
<212> TYPE: PRT
<213> ORGANISM: Homo sapiens

<400> SEQUENCE: 53

Asn Gln Tyr Gly Asn Val Leu Ser Leu
1               5

<210> SEQ ID NO 54
<211> LENGTH: 9
<212> TYPE: PRT
<213> ORGANISM: Homo sapiens

<400> SEQUENCE: 54

Lys Ala Trp Gln Pro Gly Trp Thr Val
1               5

<210> SEQ ID NO 55
<211> LENGTH: 9
<212> TYPE: PRT
<213> ORGANISM: Homo sapiens

<400> SEQUENCE: 55

Met Ala Pro Gly Ser Thr Leu Trp Leu
1               5

<210> SEQ ID NO 56
<211> LENGTH: 9
<212> TYPE: PRT
<213> ORGANISM: Homo sapiens

<400> SEQUENCE: 56

Asp Met Trp Val Met Glu Thr Gly Leu
1               5

<210> SEQ ID NO 57
<211> LENGTH: 9
<212> TYPE: PRT
<213> ORGANISM: Homo sapiens

<400> SEQUENCE: 57

Leu Thr Met Ser Phe His Leu Glu Ile
1               5

<210> SEQ ID NO 58
<211> LENGTH: 9
<212> TYPE: PRT
<213> ORGANISM: Homo sapiens

<400> SEQUENCE: 58

His Leu Glu Ile Thr Ala Arg Pro Val
1               5

<210> SEQ ID NO 59
<211> LENGTH: 9
<212> TYPE: PRT
<213> ORGANISM: Homo sapiens

<400> SEQUENCE: 59

Val Ser Ala Val Thr Leu Ala Tyr Leu
1               5

<210> SEQ ID NO 60
<211> LENGTH: 9
<212> TYPE: PRT
<213> ORGANISM: Homo sapiens

<400> SEQUENCE: 60

Cys Ser Leu Val Gly Ile Leu His Leu
1               5

<210> SEQ ID NO 61
<211> LENGTH: 9
<212> TYPE: PRT
<213> ORGANISM: Homo sapiens

<400> SEQUENCE: 61

Ser Leu Val Gly Ile Leu His Leu Gln
1               5

<210> SEQ ID NO 62
<211> LENGTH: 9
<212> TYPE: PRT
<213> ORGANISM: Homo sapiens

<400> SEQUENCE: 62

Asp Met Arg Gly Ile Leu Tyr Ala Ala
1               5

<210> SEQ ID NO 63
<211> LENGTH: 9
<212> TYPE: PRT
<213> ORGANISM: Homo sapiens

<400> SEQUENCE: 63

Ser Pro Leu Lys Pro Phe Leu Lys Leu
1               5

<210> SEQ ID NO 64
<211> LENGTH: 9
<212> TYPE: PRT
<213> ORGANISM: Homo sapiens

<400> SEQUENCE: 64

Gly Leu Pro Gly Leu Gly Ile His Met
1               5

<210> SEQ ID NO 65

```
<211> LENGTH: 9
<212> TYPE: PRT
<213> ORGANISM: Homo sapiens

<400> SEQUENCE: 65

Ala Ser Trp Leu Phe Ile Phe Asn Val
1               5

<210> SEQ ID NO 66
<211> LENGTH: 9
<212> TYPE: PRT
<213> ORGANISM: Homo sapiens

<400> SEQUENCE: 66

Leu Met Ser Pro Lys Leu Tyr Val Trp
1               5

<210> SEQ ID NO 67
<211> LENGTH: 9
<212> TYPE: PRT
<213> ORGANISM: Homo sapiens

<400> SEQUENCE: 67

Lys Gly Pro Lys Ser Leu Leu Ser Leu
1               5

<210> SEQ ID NO 68
<211> LENGTH: 9
<212> TYPE: PRT
<213> ORGANISM: Homo sapiens

<400> SEQUENCE: 68

Ser Leu Leu Ser Leu Glu Leu Lys Asp
1               5

<210> SEQ ID NO 69
<211> LENGTH: 9
<212> TYPE: PRT
<213> ORGANISM: Homo sapiens

<400> SEQUENCE: 69

Trp Val Met Glu Thr Gly Leu Leu Leu
1               5

<210> SEQ ID NO 70
<211> LENGTH: 9
<212> TYPE: PRT
<213> ORGANISM: Homo sapiens

<400> SEQUENCE: 70

Phe Cys Leu Cys Ser Leu Val Gly Ile
1               5

<210> SEQ ID NO 71
<211> LENGTH: 9
<212> TYPE: PRT
<213> ORGANISM: Homo sapiens

<400> SEQUENCE: 71

Pro Glu Glu Pro Leu Val Val Lys Val
1               5

<210> SEQ ID NO 72
<211> LENGTH: 9
<212> TYPE: PRT
<213> ORGANISM: Homo sapiens
```

```
<400> SEQUENCE: 72

Leu Thr Trp Ser Arg Glu Ser Pro Leu
1               5

<210> SEQ ID NO 73
<211> LENGTH: 9
<212> TYPE: PRT
<213> ORGANISM: Homo sapiens

<400> SEQUENCE: 73

Val Asn Val Glu Gly Ser Gly Glu Leu
1               5

<210> SEQ ID NO 74
<211> LENGTH: 9
<212> TYPE: PRT
<213> ORGANISM: Homo sapiens

<400> SEQUENCE: 74

Ser Leu Asn Gln Ser Leu Ser Gln Asp
1               5

<210> SEQ ID NO 75
<211> LENGTH: 9
<212> TYPE: PRT
<213> ORGANISM: Homo sapiens

<400> SEQUENCE: 75

Trp Leu Ser Cys Gly Val Pro Pro Asp
1               5

<210> SEQ ID NO 76
<211> LENGTH: 9
<212> TYPE: PRT
<213> ORGANISM: Homo sapiens

<400> SEQUENCE: 76

Leu Leu Leu Pro Arg Ala Thr Ala Gln
1               5

<210> SEQ ID NO 77
<211> LENGTH: 9
<212> TYPE: PRT
<213> ORGANISM: Homo sapiens

<400> SEQUENCE: 77

Val Leu Ser Leu Pro Thr Pro Thr Ser
1               5

<210> SEQ ID NO 78
<211> LENGTH: 9
<212> TYPE: PRT
<213> ORGANISM: Homo sapiens

<400> SEQUENCE: 78

Arg Ala Gln Arg Trp Ala Ala Gly Leu
1               5

<210> SEQ ID NO 79
<211> LENGTH: 9
<212> TYPE: PRT
<213> ORGANISM: Homo sapiens

<400> SEQUENCE: 79
```

Glu Leu Thr Gln Pro Val Ala Arg Thr
1               5

<210> SEQ ID NO 80
<211> LENGTH: 9
<212> TYPE: PRT
<213> ORGANISM: Homo sapiens

<400> SEQUENCE: 80

Phe Leu Leu Phe Leu Thr Pro Met Glu
1               5

<210> SEQ ID NO 81
<211> LENGTH: 9
<212> TYPE: PRT
<213> ORGANISM: Homo sapiens

<400> SEQUENCE: 81

Gly Asp Asn Ala Val Leu Gln Cys Leu
1               5

<210> SEQ ID NO 82
<211> LENGTH: 9
<212> TYPE: PRT
<213> ORGANISM: Homo sapiens

<400> SEQUENCE: 82

Ala Val Leu Gln Cys Leu Lys Gly Thr
1               5

<210> SEQ ID NO 83
<211> LENGTH: 9
<212> TYPE: PRT
<213> ORGANISM: Homo sapiens

<400> SEQUENCE: 83

Trp Leu Phe Ile Phe Asn Val Ser Gln
1               5

<210> SEQ ID NO 84
<211> LENGTH: 9
<212> TYPE: PRT
<213> ORGANISM: Homo sapiens

<400> SEQUENCE: 84

Trp Gln Pro Gly Trp Thr Val Asn Val
1               5

<210> SEQ ID NO 85
<211> LENGTH: 9
<212> TYPE: PRT
<213> ORGANISM: Homo sapiens

<400> SEQUENCE: 85

Leu Phe Arg Trp Asn Val Ser Asp Leu
1               5

<210> SEQ ID NO 86
<211> LENGTH: 9
<212> TYPE: PRT
<213> ORGANISM: Homo sapiens

<400> SEQUENCE: 86

Gly Leu Gly Cys Gly Leu Lys Asn Arg
1               5

<210> SEQ ID NO 87
<211> LENGTH: 9
<212> TYPE: PRT
<213> ORGANISM: Homo sapiens

<400> SEQUENCE: 87

Leu Leu Pro Arg Ala Thr Ala Gln Asp
1               5

<210> SEQ ID NO 88
<211> LENGTH: 9
<212> TYPE: PRT
<213> ORGANISM: Homo sapiens

<400> SEQUENCE: 88

Thr Gly Gly Trp Lys Val Ser Ala Val
1               5

<210> SEQ ID NO 89
<211> LENGTH: 9
<212> TYPE: PRT
<213> ORGANISM: Homo sapiens

<400> SEQUENCE: 89

Ser Ala Val Thr Leu Ala Tyr Leu Ile
1               5

<210> SEQ ID NO 90
<211> LENGTH: 9
<212> TYPE: PRT
<213> ORGANISM: Homo sapiens

<400> SEQUENCE: 90

His Leu Gln Arg Ala Leu Val Leu Arg
1               5

<210> SEQ ID NO 91
<211> LENGTH: 9
<212> TYPE: PRT
<213> ORGANISM: Homo sapiens

<400> SEQUENCE: 91

Gly Leu Gly Gly Thr Ala Pro Ser Tyr
1               5

<210> SEQ ID NO 92
<211> LENGTH: 9
<212> TYPE: PRT
<213> ORGANISM: Homo sapiens

<400> SEQUENCE: 92

Thr Ser Asp Gly Pro Thr Gln Gln Leu
1               5

<210> SEQ ID NO 93
<211> LENGTH: 9
<212> TYPE: PRT
<213> ORGANISM: Homo sapiens

<400> SEQUENCE: 93

Leu Lys Pro Phe Leu Lys Leu Ser Leu
1               5

<210> SEQ ID NO 94
<211> LENGTH: 9

```
<212> TYPE: PRT
<213> ORGANISM: Homo sapiens

<400> SEQUENCE: 94

Trp Asn Val Ser Asp Leu Gly Gly Leu
1               5

<210> SEQ ID NO 95
<211> LENGTH: 9
<212> TYPE: PRT
<213> ORGANISM: Homo sapiens

<400> SEQUENCE: 95

Ser Cys Gly Val Pro Pro Asp Ser Val
1               5

<210> SEQ ID NO 96
<211> LENGTH: 9
<212> TYPE: PRT
<213> ORGANISM: Homo sapiens

<400> SEQUENCE: 96

Leu Leu Ser Leu Glu Leu Lys Asp Asp
1               5

<210> SEQ ID NO 97
<211> LENGTH: 9
<212> TYPE: PRT
<213> ORGANISM: Homo sapiens

<400> SEQUENCE: 97

Val Met Glu Thr Gly Leu Leu Leu Pro
1               5

<210> SEQ ID NO 98
<211> LENGTH: 9
<212> TYPE: PRT
<213> ORGANISM: Homo sapiens

<400> SEQUENCE: 98

Thr Met Ser Phe His Leu Glu Ile Thr
1               5

<210> SEQ ID NO 99
<211> LENGTH: 9
<212> TYPE: PRT
<213> ORGANISM: Homo sapiens

<400> SEQUENCE: 99

Leu Glu Ile Thr Ala Arg Pro Val Leu
1               5

<210> SEQ ID NO 100
<211> LENGTH: 9
<212> TYPE: PRT
<213> ORGANISM: Homo sapiens

<400> SEQUENCE: 100

Leu His Leu Gln Arg Ala Leu Val Leu
1               5

<210> SEQ ID NO 101
<211> LENGTH: 9
<212> TYPE: PRT
<213> ORGANISM: Homo sapiens
```

```
<400> SEQUENCE: 101

Val Leu Arg Arg Lys Arg Lys Arg Met
1               5

<210> SEQ ID NO 102
<211> LENGTH: 9
<212> TYPE: PRT
<213> ORGANISM: Homo sapiens

<400> SEQUENCE: 102

Gly Leu Gly Arg Ala Gln Arg Trp Ala
1               5

<210> SEQ ID NO 103
<211> LENGTH: 9
<212> TYPE: PRT
<213> ORGANISM: Homo sapiens

<400> SEQUENCE: 103

Trp Ala Ala Gly Leu Gly Gly Thr Ala
1               5

<210> SEQ ID NO 104
<211> LENGTH: 9
<212> TYPE: PRT
<213> ORGANISM: Homo sapiens

<400> SEQUENCE: 104

Tyr Glu Asn Pro Glu Asp Glu Pro Leu
1               5

<210> SEQ ID NO 105
<211> LENGTH: 9
<212> TYPE: PRT
<213> ORGANISM: Homo sapiens

<400> SEQUENCE: 105

Ser Ala Trp Asp Pro Ser Arg Glu Ala
1               5

<210> SEQ ID NO 106
<211> LENGTH: 9
<212> TYPE: PRT
<213> ORGANISM: Homo sapiens

<400> SEQUENCE: 106

Ser Leu Gly Ser Gln Ser Tyr Glu Asp
1               5

<210> SEQ ID NO 107
<211> LENGTH: 9
<212> TYPE: PRT
<213> ORGANISM: Homo sapiens

<400> SEQUENCE: 107

Phe Leu Thr Pro Met Glu Val Arg Pro
1               5

<210> SEQ ID NO 108
<211> LENGTH: 9
<212> TYPE: PRT
<213> ORGANISM: Homo sapiens

<400> SEQUENCE: 108

Glu Val Arg Pro Glu Glu Pro Leu Val
```

```
1               5

<210> SEQ ID NO 109
<211> LENGTH: 9
<212> TYPE: PRT
<213> ORGANISM: Homo sapiens

<400> SEQUENCE: 109

Val Arg Pro Glu Glu Pro Leu Val Val
1               5

<210> SEQ ID NO 110
<211> LENGTH: 9
<212> TYPE: PRT
<213> ORGANISM: Homo sapiens

<400> SEQUENCE: 110

Pro Leu Val Val Lys Val Glu Glu Gly
1               5

<210> SEQ ID NO 111
<211> LENGTH: 9
<212> TYPE: PRT
<213> ORGANISM: Homo sapiens

<400> SEQUENCE: 111

Val Glu Glu Gly Asp Asn Ala Val Leu
1               5

<210> SEQ ID NO 112
<211> LENGTH: 9
<212> TYPE: PRT
<213> ORGANISM: Homo sapiens

<400> SEQUENCE: 112

Val Leu Gln Cys Leu Lys Gly Thr Ser
1               5

<210> SEQ ID NO 113
<211> LENGTH: 9
<212> TYPE: PRT
<213> ORGANISM: Homo sapiens

<400> SEQUENCE: 113

Arg Glu Ser Pro Leu Lys Pro Phe Leu
1               5

<210> SEQ ID NO 114
<211> LENGTH: 9
<212> TYPE: PRT
<213> ORGANISM: Homo sapiens

<400> SEQUENCE: 114

Phe Leu Lys Leu Ser Leu Gly Leu Pro
1               5

<210> SEQ ID NO 115
<211> LENGTH: 9
<212> TYPE: PRT
<213> ORGANISM: Homo sapiens

<400> SEQUENCE: 115

Phe Ile Phe Asn Val Ser Gln Gln Met
1               5
```

```
<210> SEQ ID NO 116
<211> LENGTH: 9
<212> TYPE: PRT
<213> ORGANISM: Homo sapiens

<400> SEQUENCE: 116

Ser Gln Gln Met Gly Gly Phe Tyr Leu
1               5

<210> SEQ ID NO 117
<211> LENGTH: 9
<212> TYPE: PRT
<213> ORGANISM: Homo sapiens

<400> SEQUENCE: 117

Tyr Leu Cys Gln Pro Gly Pro Pro Ser
1               5

<210> SEQ ID NO 118
<211> LENGTH: 9
<212> TYPE: PRT
<213> ORGANISM: Homo sapiens

<400> SEQUENCE: 118

Gly Pro Ser Ser Pro Ser Gly Lys Leu
1               5

<210> SEQ ID NO 119
<211> LENGTH: 9
<212> TYPE: PRT
<213> ORGANISM: Homo sapiens

<400> SEQUENCE: 119

Ser Gly Lys Leu Met Ser Pro Lys Leu
1               5

<210> SEQ ID NO 120
<211> LENGTH: 9
<212> TYPE: PRT
<213> ORGANISM: Homo sapiens

<400> SEQUENCE: 120

Val Trp Ala Lys Asp Arg Pro Glu Ile
1               5

<210> SEQ ID NO 121
<211> LENGTH: 9
<212> TYPE: PRT
<213> ORGANISM: Homo sapiens

<400> SEQUENCE: 121

Ile Trp Glu Gly Glu Pro Pro Cys Val
1               5

<210> SEQ ID NO 122
<211> LENGTH: 9
<212> TYPE: PRT
<213> ORGANISM: Homo sapiens

<400> SEQUENCE: 122

Asp Leu Thr Met Ala Pro Gly Ser Thr
1               5

<210> SEQ ID NO 123
<211> LENGTH: 9
<212> TYPE: PRT
```

<213> ORGANISM: Homo sapiens

<400> SEQUENCE: 123

Thr Met Ala Pro Gly Ser Thr Leu Trp
1               5

<210> SEQ ID NO 124
<211> LENGTH: 9
<212> TYPE: PRT
<213> ORGANISM: Homo sapiens

<400> SEQUENCE: 124

Val His Pro Lys Gly Pro Lys Ser Leu
1               5

<210> SEQ ID NO 125
<211> LENGTH: 9
<212> TYPE: PRT
<213> ORGANISM: Homo sapiens

<400> SEQUENCE: 125

Ile Thr Ala Arg Pro Val Leu Trp His
1               5

<210> SEQ ID NO 126
<211> LENGTH: 9
<212> TYPE: PRT
<213> ORGANISM: Homo sapiens

<400> SEQUENCE: 126

Ala Arg Pro Val Leu Trp His Trp Leu
1               5

<210> SEQ ID NO 127
<211> LENGTH: 9
<212> TYPE: PRT
<213> ORGANISM: Homo sapiens

<400> SEQUENCE: 127

Arg Thr Gly Gly Trp Lys Val Ser Ala
1               5

<210> SEQ ID NO 128
<211> LENGTH: 9
<212> TYPE: PRT
<213> ORGANISM: Homo sapiens

<400> SEQUENCE: 128

Gly Trp Lys Val Ser Ala Val Thr Leu
1               5

<210> SEQ ID NO 129
<211> LENGTH: 9
<212> TYPE: PRT
<213> ORGANISM: Homo sapiens

<400> SEQUENCE: 129

Leu Gly Ser Arg Ser Pro Pro Gly Val
1               5

<210> SEQ ID NO 130
<211> LENGTH: 9
<212> TYPE: PRT
<213> ORGANISM: Homo sapiens

<400> SEQUENCE: 130

Leu Thr Gln Pro Val Ala Arg Thr Met
1               5

<210> SEQ ID NO 131
<211> LENGTH: 9
<212> TYPE: PRT
<213> ORGANISM: Homo sapiens

<400> SEQUENCE: 131

Phe Leu Ser Pro His Gly Ser Ala Trp
1               5

<210> SEQ ID NO 132
<211> LENGTH: 9
<212> TYPE: PRT
<213> ORGANISM: Homo sapiens

<400> SEQUENCE: 132

Pro Leu Ala Ser Trp Leu Phe Ile Phe
1               5

<210> SEQ ID NO 133
<211> LENGTH: 9
<212> TYPE: PRT
<213> ORGANISM: Homo sapiens

<400> SEQUENCE: 133

Leu Asn Gln Ser Leu Ser Gln Asp Leu
1               5

<210> SEQ ID NO 134
<211> LENGTH: 9
<212> TYPE: PRT
<213> ORGANISM: Homo sapiens

<400> SEQUENCE: 134

Gly Asn Leu Thr Met Ser Phe His Leu
1               5

<210> SEQ ID NO 135
<211> LENGTH: 9
<212> TYPE: PRT
<213> ORGANISM: Homo sapiens

<400> SEQUENCE: 135

Arg Trp Ala Ala Gly Leu Gly Gly Thr
1               5

<210> SEQ ID NO 136
<211> LENGTH: 9
<212> TYPE: PRT
<213> ORGANISM: Homo sapiens

<400> SEQUENCE: 136

Ser Tyr Gly Asn Pro Ser Ser Asp Val
1               5

<210> SEQ ID NO 137
<211> LENGTH: 9
<212> TYPE: PRT
<213> ORGANISM: Homo sapiens

<400> SEQUENCE: 137

Ser Asp Val Gln Ala Asp Gly Ala Leu
1               5

<210> SEQ ID NO 138
<211> LENGTH: 9
<212> TYPE: PRT
<213> ORGANISM: Homo sapiens

<400> SEQUENCE: 138

Ala Leu Gly Ser Arg Ser Pro Pro Gly
1               5

<210> SEQ ID NO 139
<211> LENGTH: 9
<212> TYPE: PRT
<213> ORGANISM: Homo sapiens

<400> SEQUENCE: 139

Asn Leu Gly Gln Asp Gln Leu Ser Gln
1               5

<210> SEQ ID NO 140
<211> LENGTH: 9
<212> TYPE: PRT
<213> ORGANISM: Homo sapiens

<400> SEQUENCE: 140

Ser Tyr Glu Asn Glu Asp Glu Glu Leu
1               5

<210> SEQ ID NO 141
<211> LENGTH: 9
<212> TYPE: PRT
<213> ORGANISM: Homo sapiens

<400> SEQUENCE: 141

Pro Val Ala Arg Thr Met Asp Phe Leu
1               5

<210> SEQ ID NO 142
<211> LENGTH: 9
<212> TYPE: PRT
<213> ORGANISM: Homo sapiens

<400> SEQUENCE: 142

Ile Leu Tyr Ala Ala Pro Gln Leu His
1               5

<210> SEQ ID NO 143
<211> LENGTH: 9
<212> TYPE: PRT
<213> ORGANISM: Homo sapiens

<400> SEQUENCE: 143

Pro Pro Pro Arg Leu Leu Phe Phe Leu
1               5

<210> SEQ ID NO 144
<211> LENGTH: 9
<212> TYPE: PRT
<213> ORGANISM: Homo sapiens

<400> SEQUENCE: 144

Phe Phe Leu Leu Phe Leu Thr Pro Met
1               5

<210> SEQ ID NO 145

```
<211> LENGTH: 9
<212> TYPE: PRT
<213> ORGANISM: Homo sapiens

<400> SEQUENCE: 145

Cys Leu Lys Gly Thr Ser Asp Gly Pro
1               5

<210> SEQ ID NO 146
<211> LENGTH: 9
<212> TYPE: PRT
<213> ORGANISM: Homo sapiens

<400> SEQUENCE: 146

Pro Leu Lys Pro Phe Leu Lys Leu Ser
1               5

<210> SEQ ID NO 147
<211> LENGTH: 9
<212> TYPE: PRT
<213> ORGANISM: Homo sapiens

<400> SEQUENCE: 147

Pro Phe Leu Lys Leu Ser Leu Gly Leu
1               5

<210> SEQ ID NO 148
<211> LENGTH: 9
<212> TYPE: PRT
<213> ORGANISM: Homo sapiens

<400> SEQUENCE: 148

Leu Gly Leu Pro Gly Leu Gly Ile His
1               5

<210> SEQ ID NO 149
<211> LENGTH: 9
<212> TYPE: PRT
<213> ORGANISM: Homo sapiens

<400> SEQUENCE: 149

Gln Met Gly Gly Phe Tyr Leu Cys Gln
1               5

<210> SEQ ID NO 150
<211> LENGTH: 9
<212> TYPE: PRT
<213> ORGANISM: Homo sapiens

<400> SEQUENCE: 150

Ser Gly Glu Leu Phe Arg Trp Asn Val
1               5

<210> SEQ ID NO 151
<211> LENGTH: 9
<212> TYPE: PRT
<213> ORGANISM: Homo sapiens

<400> SEQUENCE: 151

Glu Leu Phe Arg Trp Asn Val Ser Asp
1               5

<210> SEQ ID NO 152
<211> LENGTH: 9
<212> TYPE: PRT
<213> ORGANISM: Homo sapiens
```

<400> SEQUENCE: 152

Ser Asp Leu Gly Gly Leu Gly Cys Gly
1               5

<210> SEQ ID NO 153
<211> LENGTH: 9
<212> TYPE: PRT
<213> ORGANISM: Homo sapiens

<400> SEQUENCE: 153

Gly Leu Lys Asn Arg Ser Ser Glu Gly
1               5

<210> SEQ ID NO 154
<211> LENGTH: 9
<212> TYPE: PRT
<213> ORGANISM: Homo sapiens

<400> SEQUENCE: 154

Pro Cys Val Pro Arg Asp Ser Leu
1               5

<210> SEQ ID NO 155
<211> LENGTH: 9
<212> TYPE: PRT
<213> ORGANISM: Homo sapiens

<400> SEQUENCE: 155

Val Ser Arg Gly Pro Leu Ser Trp Thr
1               5

<210> SEQ ID NO 156
<211> LENGTH: 9
<212> TYPE: PRT
<213> ORGANISM: Homo sapiens

<400> SEQUENCE: 156

His Pro Lys Gly Pro Lys Ser Leu Leu
1               5

<210> SEQ ID NO 157
<211> LENGTH: 9
<212> TYPE: PRT
<213> ORGANISM: Homo sapiens

<400> SEQUENCE: 157

Ser Leu Glu Leu Lys Asp Asp Arg Pro
1               5

<210> SEQ ID NO 158
<211> LENGTH: 9
<212> TYPE: PRT
<213> ORGANISM: Homo sapiens

<400> SEQUENCE: 158

Ala Arg Asp Met Trp Val Met Glu Thr
1               5

<210> SEQ ID NO 159
<211> LENGTH: 9
<212> TYPE: PRT
<213> ORGANISM: Homo sapiens

<400> SEQUENCE: 159

Met Trp Val Met Glu Thr Gly Leu Leu
1               5

<210> SEQ ID NO 160
<211> LENGTH: 9
<212> TYPE: PRT
<213> ORGANISM: Homo sapiens

<400> SEQUENCE: 160

Lys Tyr Tyr Cys His Arg Gly Asn Leu
1               5

<210> SEQ ID NO 161
<211> LENGTH: 9
<212> TYPE: PRT
<213> ORGANISM: Homo sapiens

<400> SEQUENCE: 161

Trp Leu Leu Arg Thr Gly Gly Trp Lys
1               5

<210> SEQ ID NO 162
<211> LENGTH: 9
<212> TYPE: PRT
<213> ORGANISM: Homo sapiens

<400> SEQUENCE: 162

Val Thr Leu Ala Tyr Leu Ile Phe Cys
1               5

<210> SEQ ID NO 163
<211> LENGTH: 9
<212> TYPE: PRT
<213> ORGANISM: Homo sapiens

<400> SEQUENCE: 163

Ala Gly Leu Gly Gly Thr Ala Pro Ser
1               5

<210> SEQ ID NO 164
<211> LENGTH: 9
<212> TYPE: PRT
<213> ORGANISM: Homo sapiens

<400> SEQUENCE: 164

Gln Ala Asp Gly Ala Leu Gly Ser Arg
1               5

<210> SEQ ID NO 165
<211> LENGTH: 9
<212> TYPE: PRT
<213> ORGANISM: Homo sapiens

<400> SEQUENCE: 165

Asp Ser Asn Leu Gly Gln Asp Gln Leu
1               5

<210> SEQ ID NO 166
<211> LENGTH: 9
<212> TYPE: PRT
<213> ORGANISM: Homo sapiens

<400> SEQUENCE: 166

Gln Ser Tyr Glu Asp Met Arg Gly Ile
1               5

```
<210> SEQ ID NO 167
<211> LENGTH: 9
<212> TYPE: PRT
<213> ORGANISM: Homo sapiens

<400> SEQUENCE: 167

Ser Tyr Glu Asp Met Arg Gly Ile Leu
1               5

<210> SEQ ID NO 168
<211> LENGTH: 9
<212> TYPE: PRT
<213> ORGANISM: Homo sapiens

<400> SEQUENCE: 168

Ser Ile Arg Gly Gln Pro Gly Pro Asn
1               5

<210> SEQ ID NO 169
<211> LENGTH: 9
<212> TYPE: PRT
<213> ORGANISM: Homo sapiens

<400> SEQUENCE: 169

Met Glu Val Arg Pro Glu Glu Pro Leu
1               5

<210> SEQ ID NO 170
<211> LENGTH: 9
<212> TYPE: PRT
<213> ORGANISM: Homo sapiens

<400> SEQUENCE: 170

Gln Leu Thr Trp Ser Arg Glu Ser Pro
1               5

<210> SEQ ID NO 171
<211> LENGTH: 9
<212> TYPE: PRT
<213> ORGANISM: Homo sapiens

<400> SEQUENCE: 171

Gly Ile His Met Arg Pro Leu Ala Ser
1               5

<210> SEQ ID NO 172
<211> LENGTH: 9
<212> TYPE: PRT
<213> ORGANISM: Homo sapiens

<400> SEQUENCE: 172

Arg Pro Leu Ala Ser Trp Leu Phe Ile
1               5

<210> SEQ ID NO 173
<211> LENGTH: 9
<212> TYPE: PRT
<213> ORGANISM: Homo sapiens

<400> SEQUENCE: 173

Ser Pro Ser Gly Lys Leu Met Ser Pro
1               5

<210> SEQ ID NO 174
<211> LENGTH: 9
```

```
<212> TYPE: PRT
<213> ORGANISM: Homo sapiens

<400> SEQUENCE: 174

Lys Leu Tyr Val Trp Ala Lys Asp Arg
1               5

<210> SEQ ID NO 175
<211> LENGTH: 9
<212> TYPE: PRT
<213> ORGANISM: Homo sapiens

<400> SEQUENCE: 175

Glu Ile Trp Glu Gly Glu Pro Pro Cys
1               5

<210> SEQ ID NO 176
<211> LENGTH: 9
<212> TYPE: PRT
<213> ORGANISM: Homo sapiens

<400> SEQUENCE: 176

Thr Leu Trp Leu Ser Cys Gly Val Pro
1               5

<210> SEQ ID NO 177
<211> LENGTH: 9
<212> TYPE: PRT
<213> ORGANISM: Homo sapiens

<400> SEQUENCE: 177

Gly Val Pro Pro Asp Ser Val Ser Arg
1               5

<210> SEQ ID NO 178
<211> LENGTH: 9
<212> TYPE: PRT
<213> ORGANISM: Homo sapiens

<400> SEQUENCE: 178

Ser Val Ser Arg Gly Pro Leu Ser Trp
1               5

<210> SEQ ID NO 179
<211> LENGTH: 9
<212> TYPE: PRT
<213> ORGANISM: Homo sapiens

<400> SEQUENCE: 179

Pro Lys Ser Leu Leu Ser Leu Glu Leu
1               5

<210> SEQ ID NO 180
<211> LENGTH: 9
<212> TYPE: PRT
<213> ORGANISM: Homo sapiens

<400> SEQUENCE: 180

Glu Thr Gly Leu Leu Leu Pro Arg Ala
1               5

<210> SEQ ID NO 181
<211> LENGTH: 9
<212> TYPE: PRT
<213> ORGANISM: Homo sapiens
```

```
<400> SEQUENCE: 181

Tyr Cys His Arg Gly Asn Leu Thr Met
1               5

<210> SEQ ID NO 182
<211> LENGTH: 9
<212> TYPE: PRT
<213> ORGANISM: Homo sapiens

<400> SEQUENCE: 182

Val Gly Ile Leu His Leu Gln Arg Ala
1               5

<210> SEQ ID NO 183
<211> LENGTH: 9
<212> TYPE: PRT
<213> ORGANISM: Homo sapiens

<400> SEQUENCE: 183

Ala Leu Val Leu Arg Arg Lys Arg Lys
1               5

<210> SEQ ID NO 184
<211> LENGTH: 9
<212> TYPE: PRT
<213> ORGANISM: Homo sapiens

<400> SEQUENCE: 184

Arg Met Thr Asp Pro Thr Arg Arg Phe
1               5

<210> SEQ ID NO 185
<211> LENGTH: 9
<212> TYPE: PRT
<213> ORGANISM: Homo sapiens

<400> SEQUENCE: 185

Gly Pro Gln Asn Gln Tyr Gly Asn Val
1               5

<210> SEQ ID NO 186
<211> LENGTH: 9
<212> TYPE: PRT
<213> ORGANISM: Homo sapiens

<400> SEQUENCE: 186

Asn Val Leu Ser Leu Pro Thr Pro Thr
1               5

<210> SEQ ID NO 187
<211> LENGTH: 9
<212> TYPE: PRT
<213> ORGANISM: Homo sapiens

<400> SEQUENCE: 187

Gln Leu Ser Gln Asp Gly Ser Gly Tyr
1               5

<210> SEQ ID NO 188
<211> LENGTH: 9
<212> TYPE: PRT
<213> ORGANISM: Homo sapiens

<400> SEQUENCE: 188

Glu Asp Glu Glu Leu Thr Gln Pro Val
```

```
1               5

<210> SEQ ID NO 189
<211> LENGTH: 9
<212> TYPE: PRT
<213> ORGANISM: Homo sapiens

<400> SEQUENCE: 189

Arg Thr Met Asp Phe Leu Ser Pro His
1               5

<210> SEQ ID NO 190
<211> LENGTH: 9
<212> TYPE: PRT
<213> ORGANISM: Homo sapiens

<400> SEQUENCE: 190

Asp Pro Ser Arg Glu Ala Thr Ser Leu
1               5

<210> SEQ ID NO 191
<211> LENGTH: 9
<212> TYPE: PRT
<213> ORGANISM: Homo sapiens

<400> SEQUENCE: 191

Gly Gly Arg Met Gly Thr Trp Ser Thr
1               5

<210> SEQ ID NO 192
<211> LENGTH: 9
<212> TYPE: PRT
<213> ORGANISM: Homo sapiens

<400> SEQUENCE: 192

Leu Thr Pro Met Glu Val Arg Pro Glu
1               5

<210> SEQ ID NO 193
<211> LENGTH: 9
<212> TYPE: PRT
<213> ORGANISM: Homo sapiens

<400> SEQUENCE: 193

Pro Arg Asp Ser Leu Asn Gln Ser Leu
1               5

<210> SEQ ID NO 194
<211> LENGTH: 9
<212> TYPE: PRT
<213> ORGANISM: Homo sapiens

<400> SEQUENCE: 194

Arg Gly Pro Leu Ser Trp Thr His Val
1               5

<210> SEQ ID NO 195
<211> LENGTH: 9
<212> TYPE: PRT
<213> ORGANISM: Homo sapiens

<400> SEQUENCE: 195

His Val His Pro Lys Gly Pro Lys Ser
1               5
```

-continued

```
<210> SEQ ID NO 196
<211> LENGTH: 9
<212> TYPE: PRT
<213> ORGANISM: Homo sapiens

<400> SEQUENCE: 196

Ala Thr Ala Gln Asp Ala Gly Lys Tyr
1               5

<210> SEQ ID NO 197
<211> LENGTH: 9
<212> TYPE: PRT
<213> ORGANISM: Homo sapiens

<400> SEQUENCE: 197

Asn Leu Thr Met Ser Phe His Leu Glu
1               5

<210> SEQ ID NO 198
<211> LENGTH: 9
<212> TYPE: PRT
<213> ORGANISM: Homo sapiens

<400> SEQUENCE: 198

Thr Ala Arg Pro Val Leu Trp His Trp
1               5

<210> SEQ ID NO 199
<211> LENGTH: 9
<212> TYPE: PRT
<213> ORGANISM: Homo sapiens

<400> SEQUENCE: 199

Arg Pro Val Leu Trp His Trp Leu Leu
1               5

<210> SEQ ID NO 200
<211> LENGTH: 9
<212> TYPE: PRT
<213> ORGANISM: Homo sapiens

<400> SEQUENCE: 200

Leu Val Leu Arg Arg Lys Arg Lys Arg
1               5

<210> SEQ ID NO 201
<211> LENGTH: 9
<212> TYPE: PRT
<213> ORGANISM: Homo sapiens

<400> SEQUENCE: 201

Asp Pro Thr Arg Arg Phe Phe Lys Val
1               5

<210> SEQ ID NO 202
<211> LENGTH: 9
<212> TYPE: PRT
<213> ORGANISM: Homo sapiens

<400> SEQUENCE: 202

Pro Gln Asn Gln Tyr Gly Asn Val Leu
1               5

<210> SEQ ID NO 203
<211> LENGTH: 9
<212> TYPE: PRT
```

<213> ORGANISM: Homo sapiens

<400> SEQUENCE: 203

Glu Phe Tyr Glu Asn Asp Ser Asn Leu
1               5

<210> SEQ ID NO 204
<211> LENGTH: 9
<212> TYPE: PRT
<213> ORGANISM: Homo sapiens

<400> SEQUENCE: 204

Ala Thr Ser Leu Gly Ser Gln Ser Tyr
1               5

<210> SEQ ID NO 205
<211> LENGTH: 9
<212> TYPE: PRT
<213> ORGANISM: Homo sapiens

<400> SEQUENCE: 205

Gln Leu His Ser Ile Arg Gly Gln Pro
1               5

<210> SEQ ID NO 206
<211> LENGTH: 9
<212> TYPE: PRT
<213> ORGANISM: Homo sapiens

<400> SEQUENCE: 206

Pro Ala Trp Gly Gly Gly Gly Arg Met
1               5

<210> SEQ ID NO 207
<211> LENGTH: 9
<212> TYPE: PRT
<213> ORGANISM: Homo sapiens

<400> SEQUENCE: 207

Pro Leu Trp Gly Gly Ile Met Tyr Ile
1               5

<210> SEQ ID NO 208
<211> LENGTH: 9
<212> TYPE: PRT
<213> ORGANISM: Homo sapiens

<400> SEQUENCE: 208

Lys Met Ile Met Asn Ser Leu Ser Leu
1               5

<210> SEQ ID NO 209
<211> LENGTH: 9
<212> TYPE: PRT
<213> ORGANISM: Homo sapiens

<400> SEQUENCE: 209

Phe Leu Gly Ile Leu Ser Val Met Leu
1               5

<210> SEQ ID NO 210
<211> LENGTH: 9
<212> TYPE: PRT
<213> ORGANISM: Homo sapiens

<400> SEQUENCE: 210

```
Leu Ile Phe Ala Phe Phe Gln Glu Leu
1               5

<210> SEQ ID NO 211
<211> LENGTH: 9
<212> TYPE: PRT
<213> ORGANISM: Homo sapiens

<400> SEQUENCE: 211

Gln Ile Met Asn Gly Leu Phe His Ile
1               5

<210> SEQ ID NO 212
<211> LENGTH: 9
<212> TYPE: PRT
<213> ORGANISM: Homo sapiens

<400> SEQUENCE: 212

Ile Met Tyr Ile Ile Ser Gly Ser Leu
1               5

<210> SEQ ID NO 213
<211> LENGTH: 9
<212> TYPE: PRT
<213> ORGANISM: Homo sapiens

<400> SEQUENCE: 213

Gly Met Ile Leu Ser Ile Met Asp Ile
1               5

<210> SEQ ID NO 214
<211> LENGTH: 9
<212> TYPE: PRT
<213> ORGANISM: Homo sapiens

<400> SEQUENCE: 214

Glu Ile Lys Glu Glu Val Val Gly Leu
1               5

<210> SEQ ID NO 215
<211> LENGTH: 9
<212> TYPE: PRT
<213> ORGANISM: Homo sapiens

<400> SEQUENCE: 215

Ile Ile Ser Gly Ser Leu Leu Ala Ala
1               5

<210> SEQ ID NO 216
<211> LENGTH: 9
<212> TYPE: PRT
<213> ORGANISM: Homo sapiens

<400> SEQUENCE: 216

Ser Leu Phe Ala Ala Ile Ser Gly Met
1               5

<210> SEQ ID NO 217
<211> LENGTH: 9
<212> TYPE: PRT
<213> ORGANISM: Homo sapiens

<400> SEQUENCE: 217

Ala Met Gln Ser Gly Pro Lys Pro Leu
1               5
```

<210> SEQ ID NO 218
<211> LENGTH: 9
<212> TYPE: PRT
<213> ORGANISM: Homo sapiens

<400> SEQUENCE: 218

Ile Met Asp Ile Leu Asn Ile Lys Ile
1               5

<210> SEQ ID NO 219
<211> LENGTH: 9
<212> TYPE: PRT
<213> ORGANISM: Homo sapiens

<400> SEQUENCE: 219

Ser Ile Gln Ser Leu Phe Leu Gly Ile
1               5

<210> SEQ ID NO 220
<211> LENGTH: 9
<212> TYPE: PRT
<213> ORGANISM: Homo sapiens

<400> SEQUENCE: 220

Pro Leu Phe Arg Arg Met Ser Ser Leu
1               5

<210> SEQ ID NO 221
<211> LENGTH: 9
<212> TYPE: PRT
<213> ORGANISM: Homo sapiens

<400> SEQUENCE: 221

Ile Tyr Ala Pro Ile Cys Val Thr Val
1               5

<210> SEQ ID NO 222
<211> LENGTH: 9
<212> TYPE: PRT
<213> ORGANISM: Homo sapiens

<400> SEQUENCE: 222

Met Ile Leu Ser Ile Met Asp Ile Leu
1               5

<210> SEQ ID NO 223
<211> LENGTH: 9
<212> TYPE: PRT
<213> ORGANISM: Homo sapiens

<400> SEQUENCE: 223

Ile Leu Ser Val Met Leu Ile Phe Ala
1               5

<210> SEQ ID NO 224
<211> LENGTH: 9
<212> TYPE: PRT
<213> ORGANISM: Homo sapiens

<400> SEQUENCE: 224

Gln Thr Ile Glu Ile Lys Glu Glu Val
1               5

<210> SEQ ID NO 225

```
<211> LENGTH: 9
<212> TYPE: PRT
<213> ORGANISM: Homo sapiens

<400> SEQUENCE: 225

Ser Leu Val Gly Pro Thr Gln Ser Phe
1               5

<210> SEQ ID NO 226
<211> LENGTH: 9
<212> TYPE: PRT
<213> ORGANISM: Homo sapiens

<400> SEQUENCE: 226

Ile Met Asn Gly Leu Phe His Ile Ala
1               5

<210> SEQ ID NO 227
<211> LENGTH: 9
<212> TYPE: PRT
<213> ORGANISM: Homo sapiens

<400> SEQUENCE: 227

Ala Leu Gly Gly Leu Leu Met Ile Pro
1               5

<210> SEQ ID NO 228
<211> LENGTH: 9
<212> TYPE: PRT
<213> ORGANISM: Homo sapiens

<400> SEQUENCE: 228

Gly Ile Tyr Ala Pro Ile Cys Val Thr
1               5

<210> SEQ ID NO 229
<211> LENGTH: 9
<212> TYPE: PRT
<213> ORGANISM: Homo sapiens

<400> SEQUENCE: 229

Tyr Ile Ile Ser Gly Ser Leu Leu Ala
1               5

<210> SEQ ID NO 230
<211> LENGTH: 9
<212> TYPE: PRT
<213> ORGANISM: Homo sapiens

<400> SEQUENCE: 230

Leu Met Ile Pro Ala Gly Ile Tyr Ala
1               5

<210> SEQ ID NO 231
<211> LENGTH: 9
<212> TYPE: PRT
<213> ORGANISM: Homo sapiens

<400> SEQUENCE: 231

Ser Leu Leu Ala Ala Thr Glu Lys Asn
1               5

<210> SEQ ID NO 232
<211> LENGTH: 9
<212> TYPE: PRT
<213> ORGANISM: Homo sapiens
```

<400> SEQUENCE: 232

Ile Leu Asn Ile Lys Ile Ser His Phe
1               5

<210> SEQ ID NO 233
<211> LENGTH: 9
<212> TYPE: PRT
<213> ORGANISM: Homo sapiens

<400> SEQUENCE: 233

Leu Val Ile Ala Gly Ile Val Glu Asn
1               5

<210> SEQ ID NO 234
<211> LENGTH: 9
<212> TYPE: PRT
<213> ORGANISM: Homo sapiens

<400> SEQUENCE: 234

Thr Ile Glu Ile Lys Glu Glu Val Val
1               5

<210> SEQ ID NO 235
<211> LENGTH: 9
<212> TYPE: PRT
<213> ORGANISM: Homo sapiens

<400> SEQUENCE: 235

Arg Met Ser Ser Leu Val Gly Pro Thr
1               5

<210> SEQ ID NO 236
<211> LENGTH: 9
<212> TYPE: PRT
<213> ORGANISM: Homo sapiens

<400> SEQUENCE: 236

Lys Thr Leu Gly Ala Val Gln Ile Met
1               5

<210> SEQ ID NO 237
<211> LENGTH: 9
<212> TYPE: PRT
<213> ORGANISM: Homo sapiens

<400> SEQUENCE: 237

Gly Ala Val Gln Ile Met Asn Gly Leu
1               5

<210> SEQ ID NO 238
<211> LENGTH: 9
<212> TYPE: PRT
<213> ORGANISM: Homo sapiens

<400> SEQUENCE: 238

Leu Phe His Ile Ala Leu Gly Gly Leu
1               5

<210> SEQ ID NO 239
<211> LENGTH: 9
<212> TYPE: PRT
<213> ORGANISM: Homo sapiens

<400> SEQUENCE: 239

-continued

His Ile Ala Leu Gly Gly Leu Leu Met
1               5

<210> SEQ ID NO 240
<211> LENGTH: 9
<212> TYPE: PRT
<213> ORGANISM: Homo sapiens

<400> SEQUENCE: 240

Ile Met Asn Ser Leu Ser Leu Phe Ala
1               5

<210> SEQ ID NO 241
<211> LENGTH: 9
<212> TYPE: PRT
<213> ORGANISM: Homo sapiens

<400> SEQUENCE: 241

Phe Ala Ala Ile Ser Gly Met Ile Leu
1               5

<210> SEQ ID NO 242
<211> LENGTH: 9
<212> TYPE: PRT
<213> ORGANISM: Homo sapiens

<400> SEQUENCE: 242

Leu Ser Ile Met Asp Ile Leu Asn Ile
1               5

<210> SEQ ID NO 243
<211> LENGTH: 9
<212> TYPE: PRT
<213> ORGANISM: Homo sapiens

<400> SEQUENCE: 243

Ser Ile Met Asp Ile Leu Asn Ile Lys
1               5

<210> SEQ ID NO 244
<211> LENGTH: 9
<212> TYPE: PRT
<213> ORGANISM: Homo sapiens

<400> SEQUENCE: 244

Ile Gln Ser Leu Phe Leu Gly Ile Leu
1               5

<210> SEQ ID NO 245
<211> LENGTH: 9
<212> TYPE: PRT
<213> ORGANISM: Homo sapiens

<400> SEQUENCE: 245

Val Ile Ala Gly Ile Val Glu Asn Glu
1               5

<210> SEQ ID NO 246
<211> LENGTH: 9
<212> TYPE: PRT
<213> ORGANISM: Homo sapiens

<400> SEQUENCE: 246

Met Ile Pro Ala Gly Ile Tyr Ala Pro
1               5

```
<210> SEQ ID NO 247
<211> LENGTH: 9
<212> TYPE: PRT
<213> ORGANISM: Homo sapiens

<400> SEQUENCE: 247

Ile Pro Ala Gly Ile Tyr Ala Pro Ile
1               5

<210> SEQ ID NO 248
<211> LENGTH: 9
<212> TYPE: PRT
<213> ORGANISM: Homo sapiens

<400> SEQUENCE: 248

Cys Leu Val Lys Gly Lys Met Ile Met
1               5

<210> SEQ ID NO 249
<211> LENGTH: 9
<212> TYPE: PRT
<213> ORGANISM: Homo sapiens

<400> SEQUENCE: 249

Leu Gly Ile Leu Ser Val Met Leu Ile
1               5

<210> SEQ ID NO 250
<211> LENGTH: 9
<212> TYPE: PRT
<213> ORGANISM: Homo sapiens

<400> SEQUENCE: 250

Arg Glu Ser Lys Thr Leu Gly Ala Val
1               5

<210> SEQ ID NO 251
<211> LENGTH: 9
<212> TYPE: PRT
<213> ORGANISM: Homo sapiens

<400> SEQUENCE: 251

Ser Leu Ser Leu Phe Ala Ala Ile Ser
1               5

<210> SEQ ID NO 252
<211> LENGTH: 9
<212> TYPE: PRT
<213> ORGANISM: Homo sapiens

<400> SEQUENCE: 252

Leu Asn Ile Lys Ile Ser His Phe Leu
1               5

<210> SEQ ID NO 253
<211> LENGTH: 9
<212> TYPE: PRT
<213> ORGANISM: Homo sapiens

<400> SEQUENCE: 253

Gln Tyr Cys Tyr Ser Ile Gln Ser Leu
1               5

<210> SEQ ID NO 254
<211> LENGTH: 9
```

<212> TYPE: PRT
<213> ORGANISM: Homo sapiens

<400> SEQUENCE: 254

Phe Gln Glu Leu Val Ile Ala Gly Ile
1               5

<210> SEQ ID NO 255
<211> LENGTH: 9
<212> TYPE: PRT
<213> ORGANISM: Homo sapiens

<400> SEQUENCE: 255

Arg Pro Lys Ser Asn Ile Val Leu Leu
1               5

<210> SEQ ID NO 256
<211> LENGTH: 9
<212> TYPE: PRT
<213> ORGANISM: Homo sapiens

<400> SEQUENCE: 256

Val Leu Leu Ser Ala Glu Glu Lys Lys
1               5

<210> SEQ ID NO 257
<211> LENGTH: 9
<212> TYPE: PRT
<213> ORGANISM: Homo sapiens

<400> SEQUENCE: 257

Gly Leu Phe His Ile Ala Leu Gly Gly
1               5

<210> SEQ ID NO 258
<211> LENGTH: 9
<212> TYPE: PRT
<213> ORGANISM: Homo sapiens

<400> SEQUENCE: 258

Phe His Ile Ala Leu Gly Gly Leu Leu
1               5

<210> SEQ ID NO 259
<211> LENGTH: 9
<212> TYPE: PRT
<213> ORGANISM: Homo sapiens

<400> SEQUENCE: 259

Leu Leu Met Ile Pro Ala Gly Ile Tyr
1               5

<210> SEQ ID NO 260
<211> LENGTH: 9
<212> TYPE: PRT
<213> ORGANISM: Homo sapiens

<400> SEQUENCE: 260

Val Trp Tyr Pro Leu Trp Gly Gly Ile
1               5

<210> SEQ ID NO 261
<211> LENGTH: 9
<212> TYPE: PRT
<213> ORGANISM: Homo sapiens -continued

```
<400> SEQUENCE: 261

Gly Ile Met Tyr Ile Ile Ser Gly Ser
1               5

<210> SEQ ID NO 262
<211> LENGTH: 9
<212> TYPE: PRT
<213> ORGANISM: Homo sapiens

<400> SEQUENCE: 262

Ile Ser Gly Ser Leu Leu Ala Ala Thr
1               5

<210> SEQ ID NO 263
<211> LENGTH: 9
<212> TYPE: PRT
<213> ORGANISM: Homo sapiens

<400> SEQUENCE: 263

Asn Ser Leu Ser Leu Phe Ala Ala Ile
1               5

<210> SEQ ID NO 264
<211> LENGTH: 9
<212> TYPE: PRT
<213> ORGANISM: Homo sapiens

<400> SEQUENCE: 264

Tyr Ile Asn Ile Tyr Asn Cys Glu Pro
1               5

<210> SEQ ID NO 265
<211> LENGTH: 9
<212> TYPE: PRT
<213> ORGANISM: Homo sapiens

<400> SEQUENCE: 265

Leu Phe Leu Gly Ile Leu Ser Val Met
1               5

<210> SEQ ID NO 266
<211> LENGTH: 9
<212> TYPE: PRT
<213> ORGANISM: Homo sapiens

<400> SEQUENCE: 266

Ile Phe Ala Phe Phe Gln Glu Leu Val
1               5

<210> SEQ ID NO 267
<211> LENGTH: 9
<212> TYPE: PRT
<213> ORGANISM: Homo sapiens

<400> SEQUENCE: 267

Phe Ala Phe Phe Gln Glu Leu Val Ile
1               5

<210> SEQ ID NO 268
<211> LENGTH: 9
<212> TYPE: PRT
<213> ORGANISM: Homo sapiens

<400> SEQUENCE: 268

Cys Ser Arg Pro Lys Ser Asn Ile Val
```

1               5

<210> SEQ ID NO 269
<211> LENGTH: 9
<212> TYPE: PRT
<213> ORGANISM: Homo sapiens

<400> SEQUENCE: 269

Lys Asn Glu Glu Asp Ile Glu Ile Ile
1               5

<210> SEQ ID NO 270
<211> LENGTH: 9
<212> TYPE: PRT
<213> ORGANISM: Homo sapiens

<400> SEQUENCE: 270

Pro Met Lys Gly Pro Ile Ala Met Gln
1               5

<210> SEQ ID NO 271
<211> LENGTH: 9
<212> TYPE: PRT
<213> ORGANISM: Homo sapiens

<400> SEQUENCE: 271

Phe Phe Met Arg Glu Ser Lys Thr Leu
1               5

<210> SEQ ID NO 272
<211> LENGTH: 9
<212> TYPE: PRT
<213> ORGANISM: Homo sapiens

<400> SEQUENCE: 272

Ser Lys Thr Leu Gly Ala Val Gln Ile
1               5

<210> SEQ ID NO 273
<211> LENGTH: 9
<212> TYPE: PRT
<213> ORGANISM: Homo sapiens

<400> SEQUENCE: 273

Ala Gly Ile Tyr Ala Pro Ile Cys Val
1               5

<210> SEQ ID NO 274
<211> LENGTH: 9
<212> TYPE: PRT
<213> ORGANISM: Homo sapiens

<400> SEQUENCE: 274

Ile Cys Val Thr Val Trp Tyr Pro Leu
1               5

<210> SEQ ID NO 275
<211> LENGTH: 9
<212> TYPE: PRT
<213> ORGANISM: Homo sapiens

<400> SEQUENCE: 275

Leu Trp Gly Gly Ile Met Tyr Ile Ile
1               5

-continued

```
<210> SEQ ID NO 276
<211> LENGTH: 9
<212> TYPE: PRT
<213> ORGANISM: Homo sapiens

<400> SEQUENCE: 276

Leu Leu Ala Ala Thr Glu Lys Asn Ser
1               5

<210> SEQ ID NO 277
<211> LENGTH: 9
<212> TYPE: PRT
<213> ORGANISM: Homo sapiens

<400> SEQUENCE: 277

Lys Gly Lys Met Ile Met Asn Ser Leu
1               5

<210> SEQ ID NO 278
<211> LENGTH: 9
<212> TYPE: PRT
<213> ORGANISM: Homo sapiens

<400> SEQUENCE: 278

Met Ile Met Asn Ser Leu Ser Leu Phe
1               5

<210> SEQ ID NO 279
<211> LENGTH: 9
<212> TYPE: PRT
<213> ORGANISM: Homo sapiens

<400> SEQUENCE: 279

Lys Ile Ser His Phe Leu Lys Met Glu
1               5

<210> SEQ ID NO 280
<211> LENGTH: 9
<212> TYPE: PRT
<213> ORGANISM: Homo sapiens

<400> SEQUENCE: 280

Arg Ala His Thr Pro Tyr Ile Asn Ile
1               5

<210> SEQ ID NO 281
<211> LENGTH: 9
<212> TYPE: PRT
<213> ORGANISM: Homo sapiens

<400> SEQUENCE: 281

Ala Phe Phe Gln Glu Leu Val Ile Ala
1               5

<210> SEQ ID NO 282
<211> LENGTH: 9
<212> TYPE: PRT
<213> ORGANISM: Homo sapiens

<400> SEQUENCE: 282

Gly Ile Val Glu Asn Glu Trp Lys Arg
1               5

<210> SEQ ID NO 283
<211> LENGTH: 9
<212> TYPE: PRT
```

```
<213> ORGANISM: Homo sapiens

<400> SEQUENCE: 283

Lys Ser Asn Ile Val Leu Leu Ser Ala
1               5

<210> SEQ ID NO 284
<211> LENGTH: 9
<212> TYPE: PRT
<213> ORGANISM: Homo sapiens

<400> SEQUENCE: 284

Asn Ile Val Leu Leu Ser Ala Glu Glu
1               5

<210> SEQ ID NO 285
<211> LENGTH: 9
<212> TYPE: PRT
<213> ORGANISM: Homo sapiens

<400> SEQUENCE: 285

Leu Leu Ser Ala Glu Glu Lys Lys Glu
1               5

<210> SEQ ID NO 286
<211> LENGTH: 9
<212> TYPE: PRT
<213> ORGANISM: Homo sapiens

<400> SEQUENCE: 286

Leu Phe Arg Arg Met Ser Ser Leu Val
1               5

<210> SEQ ID NO 287
<211> LENGTH: 9
<212> TYPE: PRT
<213> ORGANISM: Homo sapiens

<400> SEQUENCE: 287

Met Asn Gly Leu Phe His Ile Ala Leu
1               5

<210> SEQ ID NO 288
<211> LENGTH: 9
<212> TYPE: PRT
<213> ORGANISM: Homo sapiens

<400> SEQUENCE: 288

Met Tyr Ile Ile Ser Gly Ser Leu Leu
1               5

<210> SEQ ID NO 289
<211> LENGTH: 9
<212> TYPE: PRT
<213> ORGANISM: Homo sapiens

<400> SEQUENCE: 289

Leu Phe Ala Ala Ile Ser Gly Met Ile
1               5

<210> SEQ ID NO 290
<211> LENGTH: 9
<212> TYPE: PRT
<213> ORGANISM: Homo sapiens

<400> SEQUENCE: 290
```

Ile Leu Ser Ile Met Asp Ile Leu Asn
1               5

<210> SEQ ID NO 291
<211> LENGTH: 9
<212> TYPE: PRT
<213> ORGANISM: Homo sapiens

<400> SEQUENCE: 291

Gly Ile Leu Ser Val Met Leu Ile Phe
1               5

<210> SEQ ID NO 292
<211> LENGTH: 9
<212> TYPE: PRT
<213> ORGANISM: Homo sapiens

<400> SEQUENCE: 292

Val Met Leu Ile Phe Ala Phe Phe Gln
1               5

<210> SEQ ID NO 293
<211> LENGTH: 9
<212> TYPE: PRT
<213> ORGANISM: Homo sapiens

<400> SEQUENCE: 293

Gln Glu Leu Val Ile Ala Gly Ile Val
1               5

<210> SEQ ID NO 294
<211> LENGTH: 9
<212> TYPE: PRT
<213> ORGANISM: Homo sapiens

<400> SEQUENCE: 294

Ser Arg Pro Lys Ser Asn Ile Val Leu
1               5

<210> SEQ ID NO 295
<211> LENGTH: 9
<212> TYPE: PRT
<213> ORGANISM: Homo sapiens

<400> SEQUENCE: 295

Ser Ala Glu Glu Lys Lys Glu Gln Thr
1               5

<210> SEQ ID NO 296
<211> LENGTH: 9
<212> TYPE: PRT
<213> ORGANISM: Homo sapiens

<400> SEQUENCE: 296

Ala Glu Glu Lys Lys Glu Gln Thr Ile
1               5

<210> SEQ ID NO 297
<211> LENGTH: 9
<212> TYPE: PRT
<213> ORGANISM: Homo sapiens

<400> SEQUENCE: 297

Gly Leu Thr Glu Thr Ser Ser Gln Pro
1               5

```
<210> SEQ ID NO 298
<211> LENGTH: 9
<212> TYPE: PRT
<213> ORGANISM: Homo sapiens

<400> SEQUENCE: 298

Ile Ile Pro Ile Gln Glu Glu Glu
1               5

<210> SEQ ID NO 299
<211> LENGTH: 9
<212> TYPE: PRT
<213> ORGANISM: Homo sapiens

<400> SEQUENCE: 299

Ser Val Asn Gly Thr Phe Pro Ala Glu
1               5

<210> SEQ ID NO 300
<211> LENGTH: 9
<212> TYPE: PRT
<213> ORGANISM: Homo sapiens

<400> SEQUENCE: 300

Phe Met Arg Glu Ser Lys Thr Leu Gly
1               5

<210> SEQ ID NO 301
<211> LENGTH: 9
<212> TYPE: PRT
<213> ORGANISM: Homo sapiens

<400> SEQUENCE: 301

Leu Ala Ala Thr Glu Lys Asn Ser Arg
1               5

<210> SEQ ID NO 302
<211> LENGTH: 9
<212> TYPE: PRT
<213> ORGANISM: Homo sapiens

<400> SEQUENCE: 302

Lys Cys Leu Val Lys Gly Lys Met Ile
1               5

<210> SEQ ID NO 303
<211> LENGTH: 9
<212> TYPE: PRT
<213> ORGANISM: Homo sapiens

<400> SEQUENCE: 303

Asp Ile Leu Asn Ile Lys Ile Ser His
1               5

<210> SEQ ID NO 304
<211> LENGTH: 9
<212> TYPE: PRT
<213> ORGANISM: Homo sapiens

<400> SEQUENCE: 304

Ile Lys Ile Ser His Phe Leu Lys Met
1               5

<210> SEQ ID NO 305
```

```
<211> LENGTH: 9
<212> TYPE: PRT
<213> ORGANISM: Homo sapiens

<400> SEQUENCE: 305

Phe Leu Lys Met Glu Ser Leu Asn Phe
1               5

<210> SEQ ID NO 306
<211> LENGTH: 9
<212> TYPE: PRT
<213> ORGANISM: Homo sapiens

<400> SEQUENCE: 306

Asn Ile Tyr Asn Cys Glu Pro Ala Asn
1               5

<210> SEQ ID NO 307
<211> LENGTH: 9
<212> TYPE: PRT
<213> ORGANISM: Homo sapiens

<400> SEQUENCE: 307

Cys Tyr Ser Ile Gln Ser Leu Phe Leu
1               5

<210> SEQ ID NO 308
<211> LENGTH: 9
<212> TYPE: PRT
<213> ORGANISM: Homo sapiens

<400> SEQUENCE: 308

Met Leu Ile Phe Ala Phe Phe Gln Glu
1               5

<210> SEQ ID NO 309
<211> LENGTH: 9
<212> TYPE: PRT
<213> ORGANISM: Homo sapiens

<400> SEQUENCE: 309

Ile Lys Glu Glu Val Val Gly Leu Thr
1               5

<210> SEQ ID NO 310
<211> LENGTH: 9
<212> TYPE: PRT
<213> ORGANISM: Homo sapiens

<400> SEQUENCE: 310

Ile Glu Ile Ile Pro Ile Gln Glu Glu
1               5

<210> SEQ ID NO 311
<211> LENGTH: 9
<212> TYPE: PRT
<213> ORGANISM: Homo sapiens

<400> SEQUENCE: 311

Glu Ile Ile Pro Ile Gln Glu Glu Glu
1               5

<210> SEQ ID NO 312
<211> LENGTH: 9
<212> TYPE: PRT
<213> ORGANISM: Homo sapiens
```

<400> SEQUENCE: 312

Thr Pro Arg Asn Ser Val Asn Gly Thr
1               5

<210> SEQ ID NO 313
<211> LENGTH: 9
<212> TYPE: PRT
<213> ORGANISM: Homo sapiens

<400> SEQUENCE: 313

Pro Ala Glu Pro Met Lys Gly Pro Ile
1               5

<210> SEQ ID NO 314
<211> LENGTH: 9
<212> TYPE: PRT
<213> ORGANISM: Homo sapiens

<400> SEQUENCE: 314

Ile Ala Met Gln Ser Gly Pro Lys Pro
1               5

<210> SEQ ID NO 315
<211> LENGTH: 9
<212> TYPE: PRT
<213> ORGANISM: Homo sapiens

<400> SEQUENCE: 315

Thr Leu Gly Ala Val Gln Ile Met Asn
1               5

<210> SEQ ID NO 316
<211> LENGTH: 9
<212> TYPE: PRT
<213> ORGANISM: Homo sapiens

<400> SEQUENCE: 316

Tyr Ala Pro Ile Cys Val Thr Val Trp
1               5

<210> SEQ ID NO 317
<211> LENGTH: 9
<212> TYPE: PRT
<213> ORGANISM: Homo sapiens

<400> SEQUENCE: 317

Thr Val Trp Tyr Pro Leu Trp Gly Gly
1               5

<210> SEQ ID NO 318
<211> LENGTH: 9
<212> TYPE: PRT
<213> ORGANISM: Homo sapiens

<400> SEQUENCE: 318

Gly Gly Ile Met Tyr Ile Ile Ser Gly
1               5

<210> SEQ ID NO 319
<211> LENGTH: 9
<212> TYPE: PRT
<213> ORGANISM: Homo sapiens

<400> SEQUENCE: 319

Ala Ala Ile Ser Gly Met Ile Leu Ser
1               5

<210> SEQ ID NO 320
<211> LENGTH: 9
<212> TYPE: PRT
<213> ORGANISM: Homo sapiens

<400> SEQUENCE: 320

Ile Ser Gly Met Ile Leu Ser Ile Met
1               5

<210> SEQ ID NO 321
<211> LENGTH: 9
<212> TYPE: PRT
<213> ORGANISM: Homo sapiens

<400> SEQUENCE: 321

Ser Asn Ile Val Leu Leu Ser Ala Glu
1               5

<210> SEQ ID NO 322
<211> LENGTH: 9
<212> TYPE: PRT
<213> ORGANISM: Homo sapiens

<400> SEQUENCE: 322

Ile Val Leu Leu Ser Ala Glu Glu Lys
1               5

<210> SEQ ID NO 323
<211> LENGTH: 9
<212> TYPE: PRT
<213> ORGANISM: Homo sapiens

<400> SEQUENCE: 323

Glu Lys Lys Glu Gln Thr Ile Glu Ile
1               5

<210> SEQ ID NO 324
<211> LENGTH: 9
<212> TYPE: PRT
<213> ORGANISM: Homo sapiens

<400> SEQUENCE: 324

Ser Gln Pro Lys Asn Glu Glu Asp Ile
1               5

<210> SEQ ID NO 325
<211> LENGTH: 9
<212> TYPE: PRT
<213> ORGANISM: Homo sapiens

<400> SEQUENCE: 325

Pro Lys Asn Glu Glu Asp Ile Glu Ile
1               5

<210> SEQ ID NO 326
<211> LENGTH: 9
<212> TYPE: PRT
<213> ORGANISM: Homo sapiens

<400> SEQUENCE: 326

Ile His Met Arg Pro Leu Ala Ser Trp
1               5

```
<210> SEQ ID NO 327
<211> LENGTH: 9
<212> TYPE: PRT
<213> ORGANISM: Homo sapiens

<400> SEQUENCE: 327

Ile Ala Leu Gly Gly Leu Leu Met Ile
1               5

<210> SEQ ID NO 328
<211> LENGTH: 9
<212> TYPE: PRT
<213> ORGANISM: Homo sapiens

<400> SEQUENCE: 328

Gly Leu Leu Met Ile Pro Ala Gly Ile
1               5
```

IMMUNOGENIC CD19 PEPTIDES

CROSS-REFERENCES TO RELATED APPLICATIONS

This application is a divisional of U.S. application Ser. No. 10/884,862, filed Jul. 2, 2004, which claims priority to U.S. Provisional Application No. 60/484,689, filed Jul. 3, 2003, the entire disclosure of which are incorporated by reference and for all purposes as if fully set forth herein.

FIELD OF INVENTION

The present invention relates to immunogenic peptides. More particularly the present invention relates to CD19 or CD20 peptides that elicit an immune response.

BACKGROUND OF THE INVENTION

B-cell malignancies comprise a heterogeneous group of neoplasms including acute lymphocytic leukemia, chronic lymphocytic leukemia, and B-cell lymphomas. An estimated 65,000 new cases are diagnosed annually in the United States. Current therapeutic strategies can be effective but the majority of patients ultimately relapse and die of their disease. One promising approach for targeting B-cell malignancies involves the cellular immune system through activation of highly efficient T-lymphocytes that mediate key functions such as cytotoxicity, cytokine production, regulation of effector cells, and induction of immunological memory. Earlier clinical studies have shown that dendritic cell vaccination for the priming of naïve T cells can generate tumor-specific CTLs and induce remission in pre-treated patients with human B-cell malignancies. In addition, infusion of HLA-matched allogeneic T lymphocytes has been shown to induce durable long-term remissions in relapsed lymphomas, chronic B-lymphocytic leukemia (CLL), multiple myeloma, or EBV-associated lymphoproliferative disease after stem cell transplantation. However, only a limited percentage of patients with B-cell malignancies will achieve complete remission following donor lymphocyte infusion and the patients are at risk of developing graft-versus-host-disease, which can be associated with significant morbidity and mortality. Therefore, developing peptide-based immunotherapies against specific over-expressed tumor-associated antigens offer an attractive approach for boosting patients' immune system to treat recurrent B-cell malignancies.

CD19, a 95 kDa B lineage-specific transmembrane glycoprotein, functions as a central response regulator in B cells and offers many unique characteristics that make it a relevant target for developing immunotherapeutic strategies. With the important exception of hematopoietic stem cells, CD19 is expressed during all stages of on B cell differentiation, is down regulated on plasma cells,[15] and is maintained on cells that have undergone neoplasic transformation. It is expressed on >95% of cells in patients with B cell lymphoma, chronic B-lymphocytic leukemia, and on the acute B-lymphocytic leukemia progenitor cells. The CD19 antigen is also internalized after binding to antibody. Studies have also shown that CD19 expression is maintained despite loss of CD20 expression following treatment with anti-CD20 antibodies.

CD20 is a non-glycosylated 33-37 kDa integral membrane phosphoprotein involved in regulation of B-cell proliferation and differentiation. It is expressed slightly later in B-cell development than CD19, is not rapidly internalized, is expressed at a high surface density on the vast majority of lymphomas, and is eventually down-regulated on terminally differentiated plasma cells. Recently, in the treatment of these cancers, clinical work has focused on passive therapy using rituximab, a monoclonal antibody directed against the CD20 antigen, either alone or coupled to a radioactive compound. Although favorable clinical responses have been observed, these antibodies alone are not curative with most responders achieving only partial remissions with a mean time to disease progression of 13.2 months following antibody treatment.

It is appealing to identify, at a molecular level, the antigens that may be effective immunogens for development of protective immunity against cancer cells. Identifying these antigens would allow vaccination with immunogenic cancer-associated molecules rather than with an uncharacterized mixture of tumor molecules including both immunogenic and immunosuppressive components. Because T cells are critical for the eradication of tumors, it is necessary to understand the nature of the antigens recognized by these cells. CD19 and CD20 are well known as the B cell lymphoma associated surface antigen due to the over-expression on those cells. Monoclonal antibodies to CD20 such as rituximab have been suggested as an effective immunotherapy for B cell lymphomas. However, as set forth above, treatment with rituximab does not result in a cure. Vaccination is an alternative immunotherapeutic approach for the treatment of lymphoma. Peptide vaccines have been the subject of pre-clinical and clinical studies for the treatment of various types of tumors, including melanoma, leukemia, and breast cancer.

There continues to be a strong need for methods of diagnosing and viable treatment regimens for diseases or conditions, such as B cell lymphomas, associated with the expression of CD19 and/or CD20.

SUMMARY OF THE INVENTION

One aspect of the present invention provides isolated or recombinant leukemic antigens comprising a fragment of CD19 or CD20 antigen or a variant thereof that is capable of stimulating a cytotoxic T-lymphocyte reaction. The fragment or variant thereof can be 8, 9, 10, 11 or 12 amino acids in length. In some embodiments, the fragment or variant thereof can be up to 50 or 80 amino acids in length. In some embodiments, when the fragment is a CD20 fragment, the fragment is not a 44 amino acid extracellular domain of CD20.

In some embodiments, the fragments have defined anchor positions. In some embodiments, the second position of the fragment is L or I. In these and other embodiments, the ninth position, relative to the other anchor fragments, is L or V. In these and other embodiments, the first anchor position is preferably not N, E or P. In these and other embodiments, the third anchor position, relative to the first anchor position, is preferably not N or E. In these and other embodiments, the fourth anchor position, relative to the first anchor position, is preferably not R, K, H, or A. In these and other embodiments, the fifth anchor position, relative to the first anchor position, is preferably not P. In these and other embodiments, the seventh anchor position, relative to the first anchor position, is preferably not R, K or H. In these and other embodiments, the eighth anchor position, relative to the first anchor position, is preferably not D, E, R, K, or H. In these and other embodiments, the ninth anchor position, relative to the first anchor position, is preferably not R, K or H.

In some aspects the isolated leukemic antigen is immunologically recognized by MHC restricted T-lymphocytes that are HLA-A2.1 restricted. When the fragment is from CD19 or a variant thereof the identified leukemic antigen can include the amino acid sequence RLLFFLLFL (SEQ ID NO: 1), TLAYLIFCL (SEQ ID NO: 2), LLFLTPMEV (SEQ ID NO:

3), KLMSPKLYV (SEQ ID NO: 4), or LLFFLLFLV (SEQ ID NO: 5). When the fragment is from CD20 or a variant thereof the identified leukemic antigen can include the amino acid sequence SLFLGILSV (SEQ ID NO: 6), AISGMILSI (SEQ ID NO: 7), FIRAHTPYI (SEQ ID NO: 8), SLNFIRAHT (SEQ ID NO: 9), LKMESLNFI (SEQ ID NO: 10), SHFLKMESL (SEQ ID NO: 11), or YLFLGILSV (SEQ ID NO: 12). Suitable fragments can also include these sequences with or without one or more, such as one, two, three, four, five or more conservative or nonconservative amino acid substitutions. The isolated leukemic antigen can also be combined with one or more co-immunostimulatory molecules.

The present invention also provides a method for stimulating an immune effector cell response achieved by contacting the isolated leukemic antigen with an immune effector cell which stimulates the immune effector cell to respond against the isolated leukemic antigen. In some methods the immune effector cell is a naïve T-lymphocyte or a memory T-lymphocyte. The method can be performed by contacting the isolated leukemic antigen with an antigen presenting cell, in vivo or in vitro, such that the antigen presenting cell contacts the isolated leukemic antigen with the immune effector cell. Suitable antigen presenting cells are dendritic cells or T2 cells.

The present invention also pertains to immune effector cells and antigen presenting cells produced by these methods. Nucleic acids encoding the present isolated leukemic antigens also form part of the present invention.

DETAILED DESCRIPTION

Figure 1:
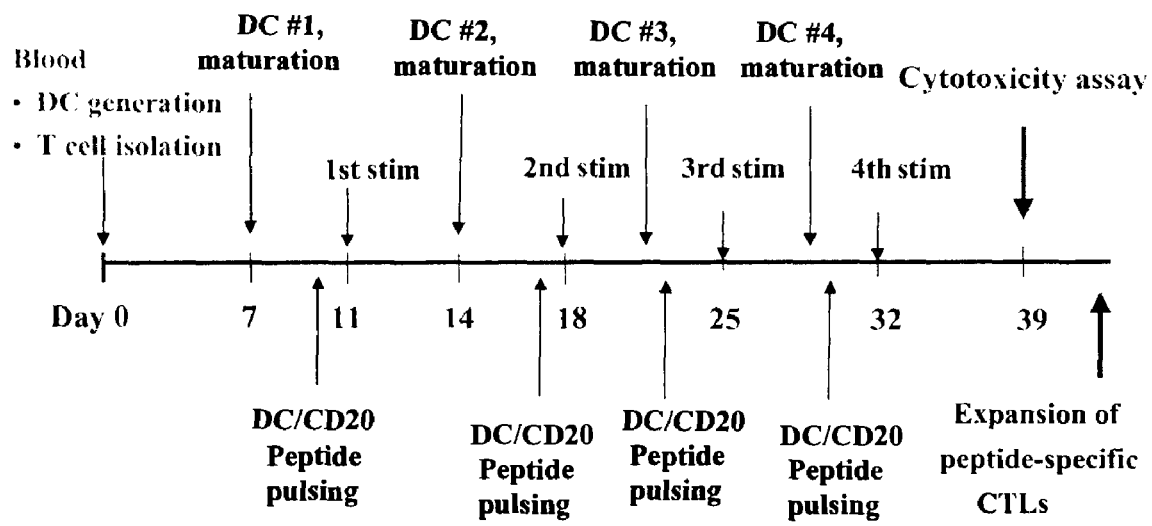
FIG. 1 is a timeline of events performed for the generation of CD20 peptide-specific cytotoxic T-lymphocytes.

The present invention encompasses fragments of the CD19 or CD20 antigen, variants, isoforms and other mammalian homologs thereof which are immunologically recognized by T lymphocytes of the immune system. CD19 antigen is a member of the Ig superfamily and is generally expressed by normal B cells including early B cells. Gene structure is highly conserved between the mouse and human homologs of this gene. Zhou et al., *Immunogenetics*, 35(2):102-111 (1992). CD19 is also found on follicular dendritic cells, early cells of myelomonocytic lineage and most stabilized B cells. The CD19 antigen is not present on T cells or on normal granulocytes.

The present invention further encompasses the antigen cancer epitope(s) which are contained in the tumor antigen. The antigenic cancer epitope specifically causes a cellular mediated immune response by interaction with T cells of the immune system. This interaction between the antigenic cancer epitope and the T cells causes the T cells to respond against, and prevent, eliminate or reduce the cancer in a mammal, including humans. The CD19 and CD20 peptides, nucleic acid molecules which code for such peptides, CD19 and CD20 binding agents such as antibodies, antigen presenting cells (APCs) and/or immune system cells (e.g., T cells), antibodies against such peptides and nucleic acids, are useful, inter alia, in diagnostic and therapeutic contexts. Thus, the present invention provides a cancer vaccine.

The CD19 antigen is discussed in Stamenkovic et al., *J Exp Med*, 168:1205-1210 (1988); and Tedder et al., *Immunol Today*, 15:437 (1994). The CD19 antigen and its murine homolog are discussed in Tedder et al., *J Immunol*, 143:712-717 (1989). The CD19 homolog of *mus musculus* is discussed in Otero et al., *J Immunol*, 170(1):73-83 (2003). The structure and domain organization of the CD19 antigen of human, mouse, and guinea pig B lymphocytes is discussed by Zhou et al., *J Immunol*, 147(4):1424-1432 (1991). The canine CD19 gene is discussed by Liu et al., *Anim Genet.* 29(1):64-65 (1998). The sequence of the CD19 homolog of *Sus scrofa* has been described by Sun et al., and is available at GenBank Accession GI:18496846.

The sequence for the CD19 antigen as reported in Tedder et al. and disclosed in the SwissProt annotated protein record P15391 is as follows:

(SEQ ID NO: 13)

```
  1 MPPPRLLFFL LFLTPMEVRP EEPLVVKVEE GDNAVLQCLK GTSDGPTQQL TWSRESPLKP

61 FLKLSLGLPG LGIHMRPLAS WLFIFNVSQQ MGGFYLCQPG PPSEKAWQPG WTVNVEGSGE

121 LFRWNVSDLG GLGCGLKNRS SEGPSSPSGK LMSPKLYVWA KDRPEIWEGE PPCVPPRDSL

181 NQSLSQDLTM APGSTLWLSC GVPPDSVSRG PLSWTHVHPK GPKSLLSLEL KDDRPARDMW

241 VMETGLLLPR ATAQDAGKYY CHRGNLTMSF HLEITARPVL WHWLLRTGGW KVSAVTLAYL

301 IFCLCSLVGI LHLQRALVLR RKRKRMTDPT RRFFKVTPPP GSGPQNQYGN VLSLPTPTSG

361 LGRAQRWAAG LGGTAPSYGN PSSDVQADGA LGSRSPPGVG PEEEEGEGYE EPDSEEDSEF

421 YENDSNLGQD QLSQDGSGYE NFEDEPLGPE DEDSFSNAES YENEDEELTQ PVARTMDFLS

481 PHGSAWDPSR EATSLGSQSY EDMRGILYAA PQLHSIRGQP GPNHEEDADS YENNDNPDGP

541 DPAWGGGGRM GTWSTR.
```

The extracellular domain of the CD19 antigen comprises residues 20-291. Other domains or regions of CD19 are set forth in the following chart. Generally, a description of "potential" in the chart can be understood as indicating that the underlying classification of the listed stretch of amino acids has not been completely elucidated.

| Key | Begin | End | Length | Description |
|---|---|---|---|---|
| SIGNAL | 1 | 19 | 19 | POTENTIAL |
| CHAIN | 20 | 556 | 537 | B-LYMPHOCYTE ANTIGEN CD 19 |
| DOMAIN | 20 | 291 | 272 | EXTRACELLULAR (POTENTIAL) |
| TRANSMEM | 292 | 313 | 22 | POTENTIAL |
| DOMAIN | 314 | 556 | 243 | CYTOPLASMIC (POTENTIAL) |
| DOMAIN | 31 | 104 | 74 | IG-LIKE C2-TYPE DOMAIN 1 |
| DOMAIN | 193 | 268 | 76 | IG-LIKE C2-TYPE DOMAIN 2 |
| DISULFIDE | 38 | 97 | 60 | POTENTIAL |
| DISULFIDE | 200 | 261 | 62 | POTENTIAL |
| CARBOHYD | 86 | 86 | 1 | N-LINKED (GLCNAX (POTENTIAL) |
| CARBOHYD | 125 | 125 | 1 | N-LINKED (GLCNAC ...) (POTENTIAL) |
| CARBOHYD | 138 | 138 | 1 | N-LINKED (GLCNAC ...) (POTENTIAL) |
| CARBOHYD | 181 | 181 | 1 | N-LINKED (GLCNAC ...) (POTENTIAL) |
| CARBOHYD | 265 | 265 | 1 | N-LINKED (GLCNAC ...) (POTENTIAL) |

References discussing antibodies against the CD19 antigen include Bejcek et al., *Cancer Res*, 55(11):2346-2351 (1995); and Tulpule et al., *Proc Ann Meet Am Soc Clin Oncol*, 13:A10 (1994). Rituximab is a monoclonal antibody that recognizes the CD20 antigen.

The CD20 antigen is a non-glycosylated phosphoprotein of approximately 35 kD. The CD20 antigen is expressed on B lymphocytes synchronously with the expression of surface IgM. Dörken et al., "Leucocyte Typing IV: White Cell Differentiation Antigens," In: Knapp W., Dörken B, Gilks W R et al., eds. *Leucocyte Typing IV: White Cell Differentiation Antigens*. Oxford: Oxford University Press, 46-48 (1989); Loken et al., *Blood*, 70:1316-1324 (1987). The antigen is present on both resting and activated B lymphocytes but is lost prior to differentiation into plasma cells. The CD20 antigen is found in both mantle-zone and germinal center areas of secondary follicles of lymphoid tissue and may be expressed on follicular dendritic cells (FDC) in germinal centers. Low-level expression of the CD20 antigen has been detected on a sub-population of T lymphocytes. Hultin et al., *Cytometry*, 14:196-204 (1993); Algino et al., *Am J Clin Pathol*, 106(1):78-81 (July 1996). CD20 antigen expression generally occurs after CD19 and CD10 expression but before CD21/22 expression and surface immunoglobulin expression. CD20 expression may be associated with acute leukemias, chronic lymphocytic leukemias and lymphomas, including B cell lymphomas, pre B ALL/LBL, lymphocyte predominant Hodgkin's lymphoma, spindle cell thymomas, and non-Hodgkin's lymphoma including mantle cell lymphoma. Scheuermann et al., *Leuk Lymphoma*, 18(5-6):385-397 (1995). Generally, CD20 is dimly expressed in both benign and neoplastic T cells. Stem cells (B cell progenitors) in bone marrow lack the CD19 and CD20 antigens, allowing healthy B cells to regenerate after treatment and return to normal levels.

The CD20 antigen is discussed by Stamenkovic et al., *J Exp Med*, 167(6):1975-1980 (1988); Tedder et al., *Proc Natl Acad Sci USA*, 85(1):208-212 (1988); Tedder et al., *J Immunol*, 142 (7):2560-2568 (1989); Einfeld et al., *EMBO J*, 7(3):711-717 (1988); and Strausberg et al., *Proc Natl Acad Sci USA*, 99(26):16899-16903 (2002). A mammalian CD20 homolog is discussed by Macardle et al., *J Bio. Regul Homeost Agents*, 16(2):136-138 (2002) (*mus musculus*). The CD20 homolog of *Rattus norvegicus* is also known and the sequence is available at GenBank Accession GI:27681331.

The sequence for the CD20 antigen disclosed in the SwissProt annotated protein record P11836 is as follows:

(SEQ ID NO: 14)

```
  1 MTTPRNSVNG TFPAEPMKGP IAMQSGPKPL FRRMSSLVGP TQSFFMRESK TLGAVQIMNG

61 LFHIALGGLL MIPAGIYAPI CVTVWYPLWG GIMYIISGSL LAATEKNSRK CLVKGKMIMN

121 SLSLFAAISG MILSIMDILN IKISHFLKME SLNFIRAHTP YINIYNCEPA NPSEKNSPST

181 QYCYSIQSLF LGILSVNLIF AFFQELVIAG IVENEWKRTC SRPKSNIVLL SAEEKKEQTI

241 EIKEEVVGLT ETSSQPKNEE DIEIIPIQEE EEEETETNFP EPPQDQESSP IENDSSP
```

The extracellular portion of CD20 comprises residues 142-188. Other domains or regions of CD20 are set forth in the following chart. Generally, a description of "potential" in the chart can be understood as indicating that the underlying classification of the listed stretch of amino acids has not been completely elucidated.

| Key | Begin | End | Length | Description |
|---|---|---|---|---|
| DOMAIN | 1 | 63 | 63 | CYTOPLASMIC (POTENTIAL) |
| TRANSMEM | 64 | 84 | 21 | POTENTIAL |
| TRANSMEM | 85 | 105 | 21 | POTENTIAL |
| TRANSMEM | 121 | 141 | 21 | POTENTIAL |
| EXTRACELL | 142 | 188 | 46 | POTENTIAL |
| TRANSMEM | 189 | 209 | 21 | POTENTIAL |
| DOMAIN | 210 | 297 | 88 | CYTOPLASMIC (POTENTIAL) |
| DISULFIDE | 111 | 220 | 110 | PROBABLE |

I. Proteins/Polypeptides/Peptides/Fragments Thereof

The compounds of this invention generally comprise a polypeptide, sometimes in isolated form, that stimulates a Th1 or CTL (cytotoxic T-lymphocyte) immune response in peripheral blood mononuclear cells (PBMCs). In particular, polypeptides 8-12 amino acids in length comprising a stimulatory portion of the CD19 or CD20 antigen are disclosed, such as a cancer or tumor rejection antigen. The peptides of the present invention can be from 8 to 80 amino acids in length, such as 8, 9, 10, 11, 12, 13, 14, 15, 16, 17, 18, 19 or 20, 25, 30, 32, 35, 40, 45, 50, 55, 60, 65, 70, 75 or 80 residues, or consecutive amino acids of CD19 or CD20, in length. Preferably, when the peptide is longer in length, the sequence of the peptide will substantially correspond with the sequence of CD19 or CD20, for example within about 1, 2, 5, 10 or 20 percent homology or identity. A cancer or tumor rejection antigen is an example of a unique fragment of a polypeptide specific to cancer that retains the functional capability of HLA binding and interaction with cytotoxic T lymphocytes. Tumor rejection antigens presented by HLA molecules typically are 9 amino acids in length, although peptides of 8, 9, 10, 11 and 12 and more amino acids, up to about 80, and can retain the capability to interact with HLA and cytotoxic T lymphocytes to an extent effective to provoke a cytotoxic T lymphocyte response (see, e.g., Van den Eynde & Brichard, *Curr Opin Immunol,* 7:674-681 (1995); Coulie et al., *Stem Cells,* 13:393-403 (1995); and discussed in U.S. Pat. No. 6,271,001). In some embodiments, the polypeptides may encompass amino acid chains of any length, including full length proteins and portions thereof, wherein amino acid residues are linked by covalent peptide bonds. Although CD19 and CD20 fragments are described herein for exemplary purposes, portions thereof, variants of the polypeptide (or portions thereof) and homologous proteins in other non-human mammals can also be used. In one preferred embodiment, the polypeptides are substantially free of contaminating endogenous materials. In some embodiments, the peptides are derived from the signaling domain, extracellular domain, transmembrane spanning domain or cytoplasmic tail of CD19 or CD20. In some embodiments, the peptide is not a 44 amino acid extracellular domain of CD20 or peptide disclosed by Robert et al., *Blood,* 99(10):3748-3755 (2002).

In certain embodiments, the components of the invention may be isolated. Generally, the term "isolated" means separated from constituents, cellular and otherwise, in which the polynucleotide, peptide, polypeptide, protein, antibody, or fragments thereof, are normally associated with in nature. As used herein, a peptide can be defined as any compound consisting of two or more amino acids. The skilled artisan will understand that a peptide and a polypeptide and protein may be used interchangeably when describing the components of the invention. A polypeptide is generally a chain of peptides or amino acids that is usually less than 100 amino acids long. A protein is a large molecule composed of one or more chains of amino acids in a specific order. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated," "separated" or "diluted" polynucleotide, peptide, polypeptide, protein, antibody, or fragment thereof is distinguishable from its naturally occurring counterpart in that the concentration or number of molecules per volume is greater than (concentrated) or less than (separated) than that of its naturally occurring counterpart. A polynucleotide, peptide, polypeptide, protein, antibody, or fragment thereof, which differs from the naturally occurring counterpart in its primary sequence or for example, by its glycosylation pattern, need not be present in its isolated form. The compound is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions are provided by this invention. Thus, as a non-limiting example, a non-naturally occurring polynucleotide is provided as a separate embodiment from the isolated naturally occurring polynucleotide. Furthermore, a protein produced in a bacterial cell is provided as a separate embodiment from the naturally occurring protein isolated from a eukaryotic cell which produces it in nature.

Several peptide fragments of the CD19 and CD20 have the ability to stimulate a T-lymphocyte mediated cellular immune response. Peptides of the present invention can include the amino acid sequences of these peptide fragments in any configuration or location in the peptide. In some embodiments, specific positions in the peptides, referred to hereinafter as anchor positions, have defined amino acids. Examples of such anchor positions associated with strong HLA-A2.1 binding to the peptide can include Leu or Ile at position 2, and/or Val at position 9. Residues putatively identified as strongly associated with weak HLA-A2.1 binding at the anchor positions are Asp, Glu, or Pro at position 1; Asp or Glu at position 3; Arg, Lys, His, or Ala at position 4; Pro at position 5; Arg, Lys, or His at position 7; Asp, Glu, Arg, Lys, or His at position 8; and Arg, Lys, and/or His at position 9. In some embodiments, the peptides disclosed herein do not have one, two, three, four or more of the above residues at the identified anchor positions that are associated with poor HLA-A2.1 binding. Generally, throughout this specification the one and three letter codes denoting amino acid residues are used in accordance with standard naming conventions, such as set forth by IUPAC.

In some embodiments, position 2 of the peptide L or I. In these and other embodiments, position 9, relative to the other anchor fragments, is V. Preferably, peptide fragments of the CD19 or CD20 protein having one or more of these anchor positions at position 2 and/or position 9, such as those shown below, are used in the present methods and compositions. Specifically, such peptide fragments can have the following sequences, where a 2 indicates the presence of an anchor amino acid at the second position as recited above, i.e., a L or I, and a 9 indicates the presence of an anchor amino acid at the ninth position as recited above, i.e., a V. An X indicates the presence of any amino acid residue.

| | |
|---|---|
| X2XXXXXX | (SEQ ID NO: 15) |
| XXXXXXXX9 | (SEQ ID NO: 16) |
| X2XXXXXX9 | (SEQ ID NO: 17) |

In some embodiments, the present peptides will contain the motif LLF, LLFF (SEQ ID NO: 18), LLFL (SEQ ID NO: 19), FLLFL (SEQ ID NO: 20), FFLLFL (SEQ ID NO: 21), LLFFLL (SEQ ID NO: 22), LFFLLFL (SEQ ID NO: 23) or LLFFLLFL (SEQ ID NO: 24), particularly when the fragment is derived from CD19. In other embodiments, the peptides can contain the motifs ILS, MES, KMES (SEQ ID NO: 25), MESL (SEQ ID NO: 26), KMESL (SEQ ID NO: 27) or LKMESL (SEQ ID NO: 28), particularly when the fragment is derived from CD20.

The present peptides should be capable of stimulating a cytotoxic T-lymphocyte reaction. The anchor positions provide a guide to the skilled artisan for modifying fragments of CD19 or CD20 to increase the immunogenicity of the peptide and "modify" the cytotoxic T-lymphocyte reaction. As will be understood by one skilled in the art, generally, the first, second, and ninth amino acids in the peptide fragments are considered to be important for binding to MHC molecules and the third, fourth, fifth, sixth and seventh amino acids are considered as important for recognition by T cell receptors. However, the interactions with neighboring amino acids within the peptide are also important to MHC binding and recognition by T cell receptors. As will be understood by the skilled artisan, the anchor positions denoted above are only numbered with respect to one another the anchor positions can be placed in any relative orientation or appropriate place within a larger immunogenic peptide. For example, any of these sequences can be part of 25 amino acid peptide and anchor position 1 can start at position 5, 7, 8, etc. within the larger peptide. Preferably, larger peptides having these anchor positions embedded within them have sequences at the non-anchor positions that correspond to the CD19 or CD20 sequence. Thus, target fragments of CD19 and CD20 and mammalian homologs thereof can be identified by aligning the desired anchor position or positions with the CD19 or CD20 or homologous protein sequence and selecting the desired portion of the CD19 or CD20 sequence or homolog.

Specific examples of CD19 peptides include those containing the sequences: RLLFFLLFL (SEQ ID NO: 1), TLAYLIFCL (SEQ ID NO: 2), LLFLTPMEV (SEQ ID NO: 3), KLMSPKLYV (SEQ ID NO: 4), or LLFFLLFLV (SEQ ID NO: 5) with or without one or more conservative or nonconservative amino acid substitutions. Specific examples of CD20 peptides include those containing the sequences: SLFLGILSV (SEQ ID NO: 6), AISGMILSI (SEQ ID NO: 7), FIRAHTPYI (SEQ ID NO: 8), SLNFIRAHT (SEQ ID NO: 9), LKMESLNFI (SEQ ID NO: 10), SHFLKMESL (SEQ ID NO: 11), or YLFLGILSV (SEQ ID NO: 12) with or without one or more conservative or nonconservative amino acid substitutions. Combinations of these peptides are also suitable for use in the present compounds and methods described herein. In some embodiments, the present peptides can also be made up of repeats of any of the above sequences, combinations of the sequences or both.

Biologically functionally equivalent variants of the present CD19 or CD20 polypeptide fragments, i.e., variants of polypeptides which retain the function of the natural polypeptide fragment, can be prepared according to methods for altering polypeptide sequence known to one of ordinary skill in the art. Examples of these methods may be such as methods, e.g., *Molecular Cloning: A Laboratory Manual*, J. Sambrook et al., eds., Second Edition, Cold Spring Harbor Laboratory Press, Cold Spring Harbor, N.Y.) 1989); or *Current Protocols in Molecular Biology*, F. M. Ausubel et al., eds., John Wiley & Sons, Inc., New York. The skilled artisan will also realize that conservative amino acid substitutions can be made in the present polypeptides to provide such functionally active homologs of the forgoing polypeptides, i.e., the homologs retain the functional capabilities of the polypeptides. As used herein, a "conservative amino acid substitution" refers to an amino acid substitution which does not alter the relative charge or size characteristics of the protein in which the amino acid substitution is made. Conservative substitutions of amino acids generally are understood to include substitutions made amongst amino acids within the following groups: (a) M, I, L, V; (b) F, Y, W; (c) K, R, H; (d) A, G; (e) S, T; (f) Q, N; and (g) E, D. Nevertheless, this grouping is meant to be non-limiting. The present invention also encompasses polypeptides with one or more nonconservative amino acid substitutions that retain similar functionality as compared to the non-modified peptide. Generally a "nonconservative amino acid substitution" is understood to be an amino acid substituted by an alternative amino acid of differing charge density, hydrophilicity/hydrophobicity, size, and/or configuration (e.g., Val for Phe). The means of making such modifications are well known in the art and can be readily accomplished by means of commercially available kits and vectors (e.g., New England Biolabs, Inc., Beverly, Mass.; Clontech, Palo Alto, Calif.). Moreover, the means of assessing such substitutions (e.g., in terms of effect on ability to bind and enter cells) are known in the art and described for example in U.S. Pat. No. 6,329,190.

The polypeptides of the present invention also include variants of the CD19 or CD20 fragments that retain the ability to stimulate a Th1 or CTL immune response in PBMCs. Such variants may include various structural forms of the primary protein, including related and homologous proteins that can be found in non-human species. Due to the presence of ionizable amino and carboxyl groups, for example, a polypeptide fragment can be in the form of an acidic or basic salt, or it can be in neutral form. Individual amino acid residues can also be modified by oxidation or reduction.

Variants within the scope of this invention also include polypeptides in which the primary amino acid structure of the polypeptide fragment is modified by forming covalent or aggregative conjugates with other polypeptides or chemical moieties such as glycosyl groups, lipids, phosphate, acetyl groups and the like. Covalent derivatives can be prepared, for example, by linking particular functional groups to amino acid side chains or at the N- or C-termini. Alternatively, for derivatives in which an additional polypeptide is joined to a CD19 or CD20 fragment, a fusion protein can be prepared using recombinant DNA techniques, such as described below. As will be understood by the skilled artisan, fusion peptides containing the 8-12 amino acid CD19 or CD20 fragment of the present invention are not limited to 8-12 amino acids in total size, but instead set forth only that the immunogenic fragment of the CD19 or CD20 antigen is 8-12 residues in size. In one such embodiment, the CD19 or CD20 polypeptide can be conjugated to a signal (or leader) polypeptide sequence at the N-terminal region of the CD19 or CD20 protein which co-translationally or post-translationally directs transfer of the protein from its site of synthesis to a site of function inside or outside of the cell membrane or wall (e.g., the yeast α-factor leader).

Also provided by this application are the polypeptides and proteins described herein conjugated to a detectable agent for use in diagnostic methods. For example, detectably labeled proteins and polypeptides can be bound to a column and used for the detection and purification of antibodies. They also are useful as immunogens for the production of antibodies as described below. Furthermore, the proteins and fragments of this invention are useful in an in vitro assay system to screen for agents or drugs that modulate cellular processes. This assay system is described in more detail in a later paragraph.

Detectable agents used in the diagnostic methods include fusions proteins that facilitate purification or identification of the polypeptides (e.g., poly-His). However, as the skilled artisan understands these types of detectable agent are meant to illustrate a non-limiting example. For instance, the peptide described by Hopp et al., *Bio/Technol* 6:1204 (1988), is a highly antigenic peptide that can be used to facilitate identification. Such a peptide provides an epitope reversibly bound by a specific monoclonal antibody, enabling rapid assay and facile purification of expressed recombinant protein. The peptide of Hopp et al. contains a sequence that may be specifically cleaved by bovine mucosal enterokinase, allowing removal of the peptide from the purified CD19 or CD20 fragment. As another advantage, fusion proteins capped with such peptides can be resistant to intracellular degradation in *E. coli.*

Protein fusions encompassed by this invention further include, for example, the polypeptides linked to an immunoglobulin Fc region. For example, if fusion proteins are made with both heavy and light chains of an antibody, it is possible to form a protein oligomer with as many as four CD19 or CD20 protein fragment regions. Also within the scope of the present invention are fusion proteins consisting of CD19 and CD20 fragments fused to polypeptides linked to a leucine zipper domain. Leucine zipper domains are described, for example, in published PCT Application WO 94/10308. The present polypeptides comprising leucine zippers may, for example, be oligomeric, dimeric or trimeric. All of the above protein fusions can be prepared by chemical linkage or as fusion proteins, as described in U.S. Pat. No. 6,013,268. Preferred protein fusions include polypeptides that comprise sequences useful for stimulating immunity to infectious pathogens (e.g., antigens). Such sequences can be derived, for example, from viruses, tumor cells, parasites or bacteria.

The proteins and polypeptides of this invention can be obtained by chemical synthesis using a commercially available automated peptide synthesizer such as those manufactured by Perkin Elmer/Applied Biosystems, Inc., Model 430A or 431A, Foster City, Calif. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods using the host cell and vector systems described throughout this specification.

Nonpeptide analogs of peptides, e.g., structures provide an increase in stabilization or lessened biodegradation, are also contemplated. Peptide mimetic analogs can be prepared based on a selected binding peptide by replacement of one or more amino acid residues by nonpeptide moieties. Preferably, the nonpeptide moieties permit the peptide to retain its natural conformation, and/or stabilize a preferred, e.g., bioactive, confirmation. Peptides containing nonpeptide moieties can be tested in molecular or cell-based binding assays to assess the effect of the substitution(s) on conformation and/or activity. One example of methods for preparation of nonpeptide mimetic analogs from peptides is described in Nachman et al., *Regul Pept* 57:359-370 (1995), and disclosed in U.S. Pat. No. 6,291,430.

The proteins of this invention also can be combined with various liquid phase carriers, such as sterile or aqueous solutions, pharmaceutically acceptable carriers, suspensions and emulsions. Examples of non-aqueous solvents that may be combined with the proteins of this invention include propyl ethylene glycol, polyethylene glycol and vegetable oils. When used to prepare antibodies, the carriers also can include an adjuvant that is useful to non-specifically augment a specific immune response. In a particular situation, a skilled artisan can easily determine whether an adjuvant is required and select one. However, for the purpose of illustration only, suitable adjuvants include, but are not limited to Freund's Complete and Incomplete, mineral salts, polynucleotides, GM-CSF and Keyhole Limpet Hemocyanin (KLH). Adjuvant can be used as is known in the art.

II. Nucleic Acids/Polynucleotides/Nucleotides/Fragments Thereof

Polynucleotides of the subject invention generally comprise a DNA or RNA sequence that encodes all or a portion of the above CD19 or CD20 polypeptide fragments, or that is complementary to such a sequence. Nucleic acids may encode proteins related or homologous to the CD19 or CD20 polypeptides discussed above. Preferably, the CD19 or CD20 nucleotide fragment is a lymphoma associated nucleic acid or is a nucleic acid or polypeptide expressed preferentially in lymphomas. Various methods for determining the expression of a nucleic acid and/or a polypeptide in normal and leukemia cells are known to those of skill in the art.

The reported nucleic acid sequence encoding the CD19 protein described above, as reported in Tedder et al., *J Immunol,* 143(2):712-717 (1989), is (SEQ ID NO: 29):

```
  1 GAATTCCTCT GACCACCATG CCACCTCCTC GCCTCCTCTT CTTCCTCCTC TTCCTCACCC

62 CCATGGAAGT CAGGCCCGAG GAACCTCTAG TGGTGAAGGT GGAAGAGGGA GATAACGCTG

121 TGCTGCAGTG CCTCAAGGGG ACCTCAGATG GCCCCACTCA GCAGCTGACC TGGTCTCGGG

181 AGTCCCCGCT TAAACCCTTC TTAAAACTCA GCCTGGGGCT GCCAGGCCTG GGAATCCACA

241 TGAGGCCCCT GGCATCCTGG CTTTTCATCT TCAACGTCTC TCAACAGATG GGGGCTTCT

301 ACCTGTGCCA GCCGGGGCCC CCCTCTGAGA AGGCCTGGCA GCCTGGCTGG ACAGTCAATG

361 TGGAGGGCAG CGGGGAGCTG TTCCGGTGGA ATGTTTCGGA CCTAGGTGGC CTGGGCTGTG

421 GCCTGAAGAA CAGGTCCTCA GAGGGCCCCA GCTCCCCTTC CGGGAAGCTC ATGAGCCCCA

481 AGCTGTATGT GTGGGCCAAA GACCGCCCTG AGATCTGGGA GGGAGAGCCT CCGTGTGTCC

541 CACCGAGGGA CAGCCTGAAC CAGAGCCTCA GCCAGGACCT CACCATGGCC CCTGGCTCCA

601 CACTCTGGCT GTCCTGTGGG GTACCCCCTG ACTCTGTGTC CAGGGGCCCC CTCTCCTGGA

661 CCCATGTGCA CCCCAAGGGG CCTAAGTCAT TGCTGAGCCT AGAGCTGAAG GACGATCGCC

721 CGGCCAGAGA TATGTGGGTA ATGGAGACGG GTCTGTTGTT GCCCCGGGCC ACAGCTCAAG

781 ACGCTGGAAA GTATTATTGT CACCGTGGCA ACCTGACCAT GTCATTCCAC CTGGAGATCA

841 CTGCTCGGCC AGTACTATGG CACTGGCTGC TGAGGACTGG TGGCTGGAAG GTCTCAGCTG
```

-continued

```
 901 TGACTTTGGC TTATCTGATC TTCTGCCTGT GTTCCCTTGT GGGCATTCTT CATCTTCAAA
 961 GAGCCCTGGT CCTGAGGAGG AAAAGAAAGC GAATGACTGA CCCCACCAGG AGATTCTTCA
1021 AAGTGACGCC TCCCCCAGGA AGCGGGCCCC AGAACCAGTA CGGGAACGTG CTGTCTCTCC
1081 CCACACCCAC CTCAGGCCTC GGACGCGCCC AGCGTTGGGC CGCAGGCCTG GGGGCACTG
1141 CCCCGTCTTA TGGAAACCCG AGCAGCGACG TCCAGGCGGA TGGAGCCTTG GGGTCCCGGA
1201 GCCCGCCGGG AGTGGGCCCA GAAGAAGAGG AAGGGGAGGG CTATGAGGAA CCTGACAGTG
1261 AGGAGGACTC CGAGTTCTAT GAGAACGACT CCAACCTTGG GCAGGACCAG CTCTCCCAGG
1321 ATGGCAGCGG CTACGAGAAC CCTGAGGATG AGCCCCTGGG TCCTGAGGAT GAAGACTCCT
1381 TCTCCAACGC TGAGTCTTAT GAGAACGAGG ATGAAGAGCT GACCCAGCCG GTCGCCAGGA
1441 CAATGGACTT CCTGAGCCCT CATGGGTCAG CCTGGGACCC CAGCCGGGAA GCAACCTCCC
1501 TGGGGTCCCA GTCCTATGAG GATATGAGAG GAATCCTGTA TGCAGCCCCC CAGCTCCACT
1561 CCATTCGGGG CCAGCCTGGA CCCAATCATG AGGAAGATGC AGACTCTTAT GAGAACATGG
1621 ATAATCCCGA TGGGCCAGAC CCAGCCTGGG GAGGAGGGGG CCGCATGGGC ACCTGGAGCA
1681 CCAGGTGATC CTCAGGTGGC CAGCCTGGAT CTCCTCAAGT CCCCAAGATT CACACCTGAC
1741 TCTGAAATCT GAAGACCTCG AGCAGATGAT GCCAACCTCT GGAGCAATGT TGCTTAGGAT
1801 GTGTGCATGT GTGTAAGTGT GTGTGTGTGT GTGTGTGTGT GTGTGTGTGT ATACATGCCA
1861 GTGACACTTC CAGTCCCCTT TGTATTCCTT AAATAAACTC AATGAGCTCT TCCAATCCAA
1921 AAATGTTAAA ATTAGCCAGG CATAGTTGTG TGTGCCTACA GTGCTACAGG AGGCTGAGGC
1981 AAGAGGATTG CTTGAGTTAA GGAAGGAAGT CAAGGCTGCA GTGAGCTATG GTCATGCCAC
2041 TGCACTCCAG CCTGGGCAAC AGCAAGACCC TGTGTCCAAA AAAAAAAAAG GAATTC
```

The reported nucleic acid sequence encoding the CD20 protein described above is (SEQ ID NO: 30):

```
  1 AAAGACAAAC TGCACCCACT GAACTCCGCA GCTAGCATCC AAATCAGCCC TTGAGATTTG
 61 AGGCCTTGGA GACTCAGGAG TTTTGAGAGC AAAATGACAA CACCCAGAAA TTCAGTAAAT
121 GGGACTTTCC CGGCAGAGCC AATGAAAGGC CCTATTGCTA TGCAATCTGG TCCAAAACCA
181 CTCTTCAGGA GGATGTCTTC ACTGGTGGGC CCCACGCAAA GCTTCTTCAT GAGGGAATCT
241 AAGACTTTGG GGCTGTCCA GATTATGAAT GGGCTCTTCC ACATTGCCCT GGGGGGTCTT
301 CTGATGATCC CAGCAGGGAT CTATGCACCC ATCTGTGTGA CTGTGTGGTA CCCTCTCTGG
361 GGAGGCATTA TGTATATTAT TTCCGGATCA CTCCTGGCAG CAACGGAGAA AAACTCCAGG
421 AAGTGTTTGG TCAAAGGAAA AATGATAATG AATTCATTGA GCCTCTTTGC TGCCATTTCT
481 GGAATGATTC TTTCAATCAT GGACATACTT AATATTAAAA TTTCCCATTT TTTAAAAATG
541 GAGAGTCTGA ATTTTATTAG AGCTCACACA CCATATATTA ACATATACAA CTGTGAACCA
601 GCTAATCCCT CTGAGAAAAA CTCCCCATCT ACCCAATACT GTTACAGCAT ACAATCTCTG
661 TTCTTGGGCA TTTTGTCAGT GATGCTGATC TTTGCCTTCT TCCAGGAACT TGTAATAGCT
721 GGCATCGTTG AGAATGAATG GAAAAGAACG TGCTCCAGAC CCAAATCTAA CATAGTTCTC
781 CTGTCAGCAG AAGAAAAAAA AGAACAGACT ATTGAAATAA AAGAAGAAGT GGTTGGGCTA
841 ACTGAAACAT CTTCCCAACC AAAGAATGAA GAAGACATTG AAATTATTCC AATCCAAGAA
901 GAGGAAGAAG AAGAAACAGA GACGAACTTT CCAGAACCTC CCCAAGATCA GGAATCCTCA
961 CCAATAGAAA ATGACAGCTC TCCTTAAGTG ATTTCTTCTG TTTTCTGTTT CCTTTTTTAA
```

```
-continued
1021  ACATTAGTGT TCATAGCTTC CAAGAGACAT GCTGACTTTC ATTTCTTGAG GTACTCTGCA

1081  CATACGCACC ACATCTCTAT CTGGCCTTTG CATGGAGTGA CCATAGCTCC TTCTCTCTTA

1141  CATTGAATGT AGAGAATGTA GCCATTGTAG CAGCTTGTGT TGTCACGCTT CTTCTTTTGA

1201  GCAACTTTCT TACACTGAAG AAAGGCAGAA TGAGTGCTTC AGAATGTGAT TTCCTACTAA

1261  CCTGTTCCTT GGATAGGCTT TTTAGTATAG TATTTTTTTT TGTCATTTTC TCCATCAGCA

1321  ACCAGGGAGA CTGCACCTGA TGGAAAAGAT ATATGACTGC TTCATGACAT TCCTAAACTA

1381  TCTTTTTTTT ATTCCACATC TACGTTTTTG GTGGAGTCCC TTTTTATCAT CCTTAAAACA

1441  ATGATGCAAA AGGGCTTTAG AGCACAATGG ATCT
```

The nucleic acids encompassed by the invention contemplate the degeneracy of the genetic code in which nucleic acids can be coded by alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets can be employed to direct the protein synthesis apparatus, in vivo or in vitro, to incorporate a serine residue. Biological molecules may also be different when isolated. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). As understood by the skilled artisan, other amino acid residues can be encoded similarly by multiple nucleotide sequences. Thus, the invention embraces degenerate nucleic acids that differ from one or more or the biologically isolated nucleic acids in codon sequence due to the degeneracy of the genetic code. Further contemplated by the invention are antisense oligonucleotides that selectively bind to a leukemia associated gene nucleic acid molecule. Additionally, nucleic acid mimetics, such as peptide nucleic acids are contemplated in the definition of nucleic acids.

The disclosed polynucleotides and peptides can be used for comparison to known and unknowns sequences using a computer-based method to match a sample sequence with known sequences. Thus, this invention also provides the polynucleotides or peptides in a computer database or in computer readable form, including applications utilizing the internet.

A linear search through such a database can be used. Alternatively, the polynucleotide sequence can be converted into a unique numeric representation. The comparison aspects can be implemented in hardware or software, or a combination of both. Preferably, these aspects of the invention are implemented in computer programs executing on a programmable computer comprising a processor, a data storage system (including volatile and non-volatile memory and/or storage elements), at least one input device, and at least one output device. Data input through one or more input devices for temporary or permanent storage in the data storage system includes both polypeptide and polynucleotide sequences, and can include previously generated polynucleotides, polypeptides and related codes for known and/or unknown sequences. Program code is applied to the input data to perform the functions described above and generate output information. The output information is applied to one or more output devices, in known fashion.

Each such computer program is preferably stored on a storage media or device (e.g., ROM or magnetic diskette) readable by a general or special purpose programmable computer for configuring and operating the computer when the storage media or device is read by the computer to perform the procedures described herein. The inventive system can also be considered to be implemented as a computer-readable storage medium, configured with a computer program, where the storage medium so configured causes a computer to operate in a specific and predefined manner to perform the functions described herein.

The polynucleotides of the present invention also can serve as primers for the detection of genes or gene transcripts that are expressed in antigen presenting cells, for example, to confirm entry of the polynucleotides into host cells by amplification or other methods known in the art. In this context, amplification means any method employing a primer-dependent polymerase capable of replicating a target sequence with reasonable fidelity. Amplification can be carried out by natural or recombinant DNA-polymerases such as T7 DNA polymerase, Klenow fragment of *E. coli* DNA polymerase, and reverse transcriptase.

The invention further provides the polynucleotide of interest operatively linked to a promoter of nucleotide, including RNA transcription, as well as other regulatory sequences for replication and/or transient or stable expression. As used herein, the term "operatively linked" means positioned in such a manner that the promoter will direct transcription off the nucleotide of interest. Examples of promoters that may be used "include" SP6, T4 and T7. In certain embodiments, cell-specific promoters are used for cell-specific expression of the polynucleotide of interest. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, (see Gene Expression Technology, Goeddel ed., Academic Press, Inc. (1991), and references cited therein; and Vectors: *Essential Data Series*, Gacesa and Ramji, eds., John Wiley & Sons, NY (1994)). These references contain maps, functional properties, commercial suppliers and a reference to Gen-EMBL accession numbers for various suitable vectors. Preferable, these vectors are capable of transcribing RNA in vivo or in vitro.

Expression vectors containing the polynucleotides are useful to obtain host vector systems that produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc.

Adenoviral vectors are particularly useful for introducing genes into tissues in vivo because of their high levels of expression and efficient transformation of cells both in vivo and in vitro. When using these vectors, and/or a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells. See Sambrook et al., 1989, supra. In addition to the use of the above vectors, including viral vectors for insertion of exogenous nucleic acid into cells, the nucleic acid can be inserted into the host cell by other methods well known in the art such as transformation for bacterial cells; transfection, for example by calcium phosphate precipitation, for mammalian cells; or DEAE-dextran; electroporation; or microinjection for mammalian cells. These methodologies are well known in the art and are demonstrated in Sambrook. See Sambrook et al., 1989, supra, for this methodology. Thus, this invention also provides a host cell, e.g., a mammalian cell, an animal cell (rat or mouse), a human cell, or a prokaryotic cell such as a bacterial cell, containing a polynucleotide encoding a protein or polypeptide or antibody.

When vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this invention can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector's biological material in the infected host cell. An example of a replication-incompetent retroviral vector is LNL6 (Miller A D et al., *BioTechniques* 7:980-990 (1989)). The methodology of using replication-incompetent retroviruses for retroviral-mediated gene transfer of gene markers is well established (Correll et al., *Proc Natl Acad Sci USA* 86:8912 (1989); Bordignon, *Proc Natl Acad Sci USA,* 86:8912-8952 (1989); Culver K, *Proc Natl Acad Sci USA* 88:3155 (1991); and Rill D R, Blood, 79(10): 2694-2700 (1991)) and will be understood by one of skill in the art.

The host cells containing the polynucleotides of this invention are useful for the recombinant replication of the polynucleotides and for the recombinant production of peptides. Alternatively, the cells can be used to induce an immune response in a subject in the methods described herein. When the host cells are antigen presenting cells, they can be used to expand a population of immune effector cells such as tumor infiltrating lymphocytes, which in turn are useful in adoptive immunotherapies.

III. Protein Binding Agents (Antibodies)

The invention also involves agents which bind to the leukemia associated polypeptides disclosed herein. Such binding agents can be used in screening assays to detect the presence or absence of the polypeptides. The binding agents may also be used in purification protocols to isolate these polypeptides. Such binding partners can be used further to selectively target drugs, toxins or other molecules to leukemia cells which present the associated polypeptides. In this manner, cells present in cells which express the CD19 or CD20 fragments can be treated with cytotoxic compounds.

The invention, therefore, involves antibodies or fragments of antibodies having the ability to selectively bind to the disclosed polypeptides. Antibodies against the CD19 or CD20 antigens are discussed above. Antibodies include polyclonal and monoclonal antibodies, prepared according to conventional methodology. The antibodies can include, but are not limited to mouse, rat, rabbit, and/or human antibodies. The antibodies are useful to identify and purify polypeptides and APCs expressing the polypeptides.

The antibodies of the present invention are prepared by any of a variety of methods, including administering protein, fragments of protein, cells expressing the protein or fragments thereof and the like to an animal to induce polyclonal antibodies. Laboratory methods for producing polyclonal antibodies and monoclonal antibodies, as well as deducing their corresponding nucleic acid sequences, are known in the art, for example, see Harlow and Lane, 1988, supra, and Sambrook et al, 1989, supra. The monoclonal antibodies of this invention can be biologically produced by introducing protein or a fragment thereof into an animal, e.g., a mouse or a rabbit. The antibody producing cells in the animal are then isolated and fused with myeloma cells or heteromyeloma cells to produce hybrid cells or hybridomas. Accordingly, hybridoma cells producing the monoclonal antibodies of this invention also are provided.

The antibodies of this invention can be linked to a detectable agent or label. There are many different labels and methods of labeling known to those of ordinary skill in the art. The coupling of antibodies to low molecular weight haptens can increase the sensitivity of various biological assays. The haptens can then be specifically detected by means of a second reaction. For example, it is common to use haptens such as biotin, which reacts with avidin, or dinitropherryl, pyridoxal, and fluorescein, which can react with specific anti-hapten antibodies. See Harlow and Lane, 1988, supra. Antibodies also can be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention preferably are specific for the CD19 or CD20 complexes described herein.

The monoclonal antibodies of the invention also can be bound to many different carriers. Thus, this invention provides compositions containing the antibodies and another substance, which may be active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Thus, using the protein or fragment thereof, and well known methods, one of skill in the art can produce and screen the hybridoma cells and antibodies of this invention for antibodies having the ability to bind the proteins or polypeptides. As detailed herein, such antibodies can also be used to identify tissues expressing protein or to purify protein.

If a monoclonal antibody being tested binds with the protein or polypeptide, then the antibody being tested and the antibodies provided by the hybridomas of this invention are equivalent. It also is possible to determine without undue experimentation, whether an antibody has overlapping specificity with the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate with the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" is intended to include antibodies of all isotypes. Particular isotypes of a monoclonal antibody can be prepared either directly by selecting from the initial fusion, or prepared secondarily, such as from a parental hybridoma secreting a monoclonal antibody of different isotype by using the sib selection technique to isolate class switch variants. This procedure is described in Steplewski et al., Proc Natl Acad Sci, 82:8653 (1985); and Spira et al., J Immunol Methods, 74:307 (1984).

This invention also contemplates the use of biological active fragments of the polyclonal and monoclonal antibodies described above. These "antibody fragments" retain some ability to selectively bind with their antigen or immunogen. Such antibody fragments can include, but are not limited to: (1) Fab, (2) Fab', (3) F(ab')$_2$, (4) Fv, and (5) SCA. A specific example of "a biologically active antibody fragment" is a CDR region of an antibody. Methods of making these antibody fragments are known in the art, see for example, Harlow and Lane, 1988, supra.

The isolation of hybridomas secreting monoclonal antibodies with the specificity of the monoclonal antibodies of the invention can be accomplished by the production of one of ordinary skill in the art anti-idiotypic antibodies (Herlyn et al., Science, 232:100 (1986)). An anti-idiotypic antibody is an antibody that recognizes unique determinants present on the monoclonal antibody produced by the hybridoma of interest. Generally, idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Compositions containing the antibodies, fragments thereof or cell lines which produce the antibodies, are encompassed by this invention. When these compositions are to be used pharmaceutically, they can be combined with a pharmaceutically acceptable carrier.

IV. Pulsing Antigen Presenting Cells

The polypeptides of this invention can be pulsed into antigen presenting cells either in vivo or in vitro using the methods described herein. Various methods of pulsing antigen presenting cells are disclosed in U.S. Pat. No. 6,306,640; Lodge et al., Cancer Res, 60:829 (2000); Lau et al., J Immun, 24 (1):66 (2001); Gajewski et al., Clin Cancer Res, 7:895 (2001); Morse et al., Clin Cancer Res, 5:1331 (1999); and Schmidt et al., Proc Natl Acad Sci, 94:3262 (1997). Antigen-presenting cells, include, but are not limited to dendritic cells (DCs), monocytes/macrophages, B lymphocytes or other cell type(s) expressing the necessary MHC/co-immunostimulatory molecules. The methods described below focus primarily on DCs which are the most potent, preferred APCs. These antigen presenting host cells containing the polypeptides or proteins are further provided.

The term "antigen-presenting cells" or "APCs" includes both intact, whole cells as well as other molecules that are capable of inducing the presentation of one or more antigens, preferably in association with MHC molecules. Examples of suitable APCs are discussed in detail below and include, but are not limited to, whole cells such as macrophages, dendritic cells, B cells, purified MHC class I molecules complexed to beta 2-microglobulin and foster antigen presenting cells.

Dendritic cells (DCs) are the most effective type of antigen presenting cells (APC) in the human body. Dendritic cells express significant levels of co-immunostimulatory (CD86, CD80) and MHC class I and class II molecules on their cell surface. Many different factors and cytokine combinations have been demonstrated to produce mature dendritic cells (mDCs) in vitro. It has been shown that DCs provide all the signals, which are generally characterized into two types, required for T cell activation and proliferation. The first type of signal, which gives specificity to the immune response, is mediated through interaction between the T cell receptor/CD3 ("TCR/CD3") complex and an antigenic peptide presented by a major histocompatibility complex ("MHC") class I or II protein on the surface of DCs and other APCs. This interaction between TCR/CD3 and the antigenic peptide is necessary, but not sufficient, for T cell activation to occur. In fact, without the second type of signal, the signal between the TCR/CD3 and Antigenic peptide result in T cell energy. The second type of signal, called a co-immunostimulatory signal, is neither antigen-specific nor MHC-restricted, this second type of signal, and can lead to a full proliferation response of T cells and induction of T cell effector functions in the presence of the first type of signals. As used herein, "dendritic cell" is to include, but not be limited to a pulsed dendritic cell, a foster cell or a dendritic cell hybrid.

As demonstrated in the Examples, the present methods, peptides and effector cells can induce or provide not only significant levels of cytotoxicity, but levels of cytotoxicity from about 10 percent up to about 50 percent, or more specifically 21, 29, 31, 33, 34, 35, 36, 37 or 39 percent to 42, 43, 45, 46, 50 percent in various cell types.

Isolated antigen presenting host cells that present the polypeptides of this invention in the context of MHC molecules are further useful to expand and isolate a population of educated, antigen-specific immune effector cells. The term "immune effector cells" refers to cells capable of binding an antigen or mediating an immune response. These cells include, but are not limited to, T cells, B cells, monocytes, macrophages, NK cells and cytotoxic T lymphocytes (CTLs), for example CTL lines, CTL clones, and CTLs from tumor inflammatory regions, or other infiltrates. The immune effector cells, e.g., cytotoxic T lymphocytes, are preferably produced by culturing naive immune effector cells with antigen-presenting cells that present the polypeptides in the context of MHC molecules on the surface of the APCs. A "naive" cell is a cell that has never been exposed to an antigen. The population of educated, antigen-specific immune effector cells can be purified using methods known in the art, e.g., FACS analysis or ficoll gradients. The methods used to generate and culture the immune effector cells as well as the populations produced thereby also are the inventor's contribution and invention. [Pharmaceutical compositions comprising the cells and pharmaceutically acceptable carriers are useful in adoptive immunotherapy. Prior to administration in vivo, the immune effector cells can be screened in vitro for their ability to lyse melanoma tumor cells.]

In one embodiment, the immune effector cells and/or the APCs are genetically modified. Using standard gene transfer, genes coding for co-immunostimulatory molecules and/or stimulatory cytokines can be inserted prior to, concurrent to or subsequent to expansion of the immune effector cells.

The present invention also encompasses immune effector cells that have been exposed to polypeptides of the present invention, preferably where the polypeptides are in an isolated form. Alternative to the above, the immune effector cells can be exposed to the polypeptides, preferably in the presence of one or more stimulatory molecules, without the help of antigen presenting cells.

V. Immune Response Induction

This invention also provides methods of inducing an immune response in a subject, comprising administering to the subject an effective amount of the polypeptides described above under the conditions that induce an immune response to the polypeptide. The polypeptides can be administered in formulations or as polynucleotides encoding the polypeptides. The polynucleotides can be administered in a gene delivery vehicle or by inserting into a host cell that in turn recombinantly transcribes, translates and processes the encoded polypeptide. Isolated host cells containing the polynucleotides of this invention and a pharmaceutically acceptable carrier can therefore be combined with an appropriate and effective amount of an adjuvant, cytokine or co-immunostimulatory molecule for an effective vaccine regimen. The vaccination can either be prophylactic or for treatment of established cancer. In one embodiment, the host cell used in the vaccine regimen is an APC such as a dendritic cell. In some embodiments, host cell can be further modified by inserting a polynucleotide coding for an effective amount of either or both of a cytokine or co-immunostimulatory molecule.

Co-administering an effective amount of a cytokine or co-immunostimulatory molecule with the methods of the invention. As used herein, the term "cytokine" refers to any one of the numerous factors that exert a variety of effects on cells, for example, inducing growth or proliferation. Non-limiting examples of cytokines which can be used alone or in combination in the practice of the present invention include, interleukin-2 (IL-2), stem cell factor (SCF), interleukin 3 (IL-3), interleukin 6 (IL-6), interleukin 12 (IL-12), granulocyte colony stimulating factor (G-CSF), granulocyte macrophage-colony stimulating factor (GM-CSF), interleukin-1 alpha (IL-1.sub.I), interleukin-11 (IL-11), MIP-1$_f$, leukemia inhibitory factor (LIF), c-kit ligand, thrombopoietin (TPO) and flt3 ligand. The present invention also anticipates use of culture conditions in which one or more of the above cytokines is specifically excluded from the medium. Generally, these cytokines are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). It is intended, although not always explicitly stated, that molecules having similar biological activity as wild-type or purified cytokines (e.g., recombinantly produced or muteins thereof) may be used while still maintaining within the spirit and scope of the invention.

Co-immunostimulatory molecules may also be used in the present invention. "Co-immunostimulatory molecules" are involved in the interaction between receptor-ligand pairs expressed on the surface of antigen presenting cells and T cells. One exemplary receptor-ligand pair is the B7 co-immunostimulatory molecule on the surface of DCs and its counter-receptor CD28 or CTLA-4 on T cells (Freeman et al., *Science*, 262:909-991 (1993); Young et al., *J Clin Invest*, 90:229 (1992); Nabavi et al., *Nature*, 360:266 (1992)). Other important co-immunostimulatory molecules are CD40, CD54, CD80, CD86.

Patient T cell assays can generally be performed by treating patient PBMCs with the reactive antigens and analyzing the cells for a suitable response. For example, the PBMC supernatant can be assayed for the level of secreted cytokines. Preferably, the cytokine assayed is interferon-gamma, (ICN-y) IL-2, IL-12 (either the p40 subunit or biologically active p70), IL-1 or tumor necrosis factor-α TNF-α. The cytokines interleukin-4 and interleukin-10 can also be assayed, since the levels of these representative Th2-type cytokines generally decrease in response to treatment with a polypeptide as described herein. Cytokines can be assayed, for example, in an ELISA format using commercially available antibodies specific for the cytokine of interest. Generally, positive results will be determined according to the manufacturer's instructions. Suitable antibodies can be obtained from many commercial suppliers including Chemicon, Temucula, Calif. and PharMingen, San Diego, Calif. Alternatively, the treated PBMCs can be assayed for mRNA encoding one or more of the cytokines interferon-gamma, interleukin-2, interleukin-12 p40 subunit, interleukin-1 or tumor necrosis factor-α, or the PBMCs can be assayed for a proliferative response as described herein. Alternatively, cytokines can be measured by testing PBMC supernatants for cytokine-specific biological activities.

VI. Method of Diagnosis

According to one aspect of the invention, methods for diagnosing a disorder that is characterized by expression of a CD19 or CD20 nucleic acid or polypeptide are provided. The methods involve contacting a biological sample isolated from a subject with an agent specific for the leukemia associated nucleic acid or polypeptide to detect the presence of the leukemia associated nucleic acid or polypeptide in the biological sample. As used herein, "contacting" means placing the biological sample in sufficient proximity to the agent and under the appropriate conditions, e.g., concentration, temperature, time, ionic strength, etc. to allow the specific interaction between the agent and the leukemia associated nucleic acid or polypeptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a hematopoietic tissue in vivo and the agent specific for the leukemia associated nucleic acid or polypeptide can be used to detect the presence of such molecules in the hematopoietic tissue (e.g., for imaging portions of the hematopoietic tissue that express the leukemia associated genes and gene products). Alternatively, the biological sample can be located in vitro (e.g., a blood sample, a bone marrow biopsy, a tissue extract). In a particularly preferred embodiment, the biological sample can be a cell-containing sample, more preferably a sample containing hematopoietic cells.

Although the method is not meant to be limiting, the skilled artisan can determine which HLA molecule binds to the CD19 or CD20 fragments by experiments utilizing antibodies to block specific individual HLA class I molecules or experiments using labeled fragments. For example, antibodies which bind selectively to HLA-A2 will prevent efficient presentation of antigens specifically presented by HLA-A2. Thus, if the present peptides are presented by HLA-A2, then the inclusion of anti-HLA-A2 antibodies in an in vitro assay will block the presentation of these antigens. An assay for determining the nature of the HLA molecule is found in U.S. Pat. No. 5,939,526.

VII. Therapeutic Compositions/Vaccines

When administered, the therapeutic compositions of the present invention are administered in pharmaceutically acceptable preparations. Such preparations can routinely contain pharmaceutically acceptable concentrations of salt, buffering agents, preservatives, compatible carriers, supplementary immune potentiating agents such as adjuvants and cytokines and optionally other therapeutic agents.

The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The present invention provides therapeutic compositions including vaccine compositions comprising the CD19 or CD20 antigen peptide fragments or nucleic acids encoding these fragments as described above. Vaccines can be prepared from antigen presenting cells that have been pulsed with the peptides or nucleic acids or immune effector cells which have been exposed to the peptides or nucleic acids. The vaccine can contain a single peptide or a range of peptides that cover different or similar epitopes. In addition or alternatively, the vaccine can be a polyvalent vaccine where a single polypeptide can be provided with multiple epitopes. The vaccine compositions of the present invention may be cancer vaccines In one embodiment of a vaccine composition, the peptide is conjugated to a carrier protein, for example a polycation (poly-L-Lysine or poly-L-arginine), tetanus toxoid, diphtheria toxoid or oxidized KLH or the like in order to stimulate T cell help as disclosed in U.S. Pat. No. 6,344,203.

Included as part of the vaccine, substances that potentiate the immune response can be administered with nucleic acid or peptide components. Such immune response potentiating compounds can be classified as either adjuvants or cytokines. Adjuvants can enhance the immunological response by providing a reservoir of antigen (extracellularly or within macrophages), activating macrophages, and stimulating specific sets of lymphocytes. Adjuvants of many kinds are well known in the art; specific examples include MPL (SmithKline Beecham), a congener obtained after purification and acid hydrolysis of *Salmonella* minnesota R595 lipopolysaccharide, QS21 (SmithKline Beecham), a pure QA-21 saponin purified from *Quillja saponaria* extract, GM-CSF, Incomplete Freund's adjuvant, KLH and various water-in-oil emulsions prepared from biodegradable oils such as squalene and/or tocopherol. Because of their lymphocyte stimulatory properties, cytokines are also useful in vaccination protocols. Many cytokines useful for such purposes will be known to one of ordinary skill in the art and may include interleukin-12 (IL-12) which has been shown to enhance the protective effects of vaccines (Hall, *Science*, 268:1432-1434 (1995)).

The therapeutics of the invention can be administered by any conventional route, including injection or by gradual infusion over time. Following immunization protocols standard in the art, initial doses can be followed by booster doses. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, Gennaro et al., 18 ed.: 1694-1712 (1990)). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Aqueous carriers include water, alcoholic/aqueous solutions, emulsions or suspensions, including saline and buffered media. Examples of non-aqueous solvents include propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's or fixed oils. If the preparation is administered intravenously, intravenous vehicles include fluid and nutrient replenishers, electrolyte replenishers (such as those based on Ringer's dextrose), and the like. Preservatives and other additives such as, for example, antimicrobials, anti-oxidants, chelating agents, and inert gases and the like may also be present.

In cases where cells are used as a vaccine, these can be cells transfected with coding sequences for one or both of the components necessary to provoke a CTL response, or be cells that already express both molecules without the need for transfection. Vaccines also encompass naked DNA or RNA, encoding the present peptides, which can be produced in vitro and administered via injection, particle bombardment, nasal aspiration and using other methods. Vaccines of the "naked nucleic acid" type have been demonstrated to provoke an immunological response including generation of CTLs specific for the peptide encoded by the naked nucleic acid (Ulmer et al., *Science,* 259:1745-1748 (1993)). When "disorder" is used herein, it refers to any pathological condition where the tumor rejection antigen precursor is expressed. In particular examples of such disorders are cancers, leukemias and lymphomas.

The peptides of the present invention can also be used to elicit or enhance an immune response to an antigen encoded by a DNA vaccine. DNA vaccines may encode one or more immunostimulating antigens such that the antigen is generated in situ. For instance, the DNA vaccine can encode a tumor antigen and, optionally, a peptide as described herein. In such vaccines, the DNA can be present within any of a variety of delivery systems known to those of ordinary skill in the art, including nucleic acid expression systems, such as bacteria and viral expression systems. Appropriate nucleic acid expression systems contain the necessary DNA sequences for expression in the patient (such as a suitable promoter). Bacterial delivery systems involve the administration of a bacterium (such as *Bacillus*-Calmette-Guerrin) that expresses an epitope of a leukemia cell antigen on its cell surface. The DNA can be introduced using a viral expression system (e.g., vaccinia or other pox virus, retrovirus, or adenovirus), which may involve the use of a non-pathogenic (defective), replication competent virus. A variety of suitable delivery systems are disclosed, for example, in Fisher-Hoch et al., *Proc Natl Acad Sci,* 86:317-321 (1989); Flexner et al., *Ann NY Acad Sci,* 569:86-103 (1989); Flexner et al., *Vaccine,* 8:17-21 (1990); U.S. Pat. Nos. 4,603,112; 4,769,330; 4,777,127; and 5,017,487; WO 89/01973; GB 2,200,651; EP 0,345,242; WO 91/02805; Berkner, *Biotechniques,* 6:616-627 (1988); Rosenfeld et al., *Science* 252:431-434 (1991); Kolls et al., *Proc Natl Acad Sci,* 91:215-219 (1994); Kass-Eisler et al., *Proc Natl Acad Sci* 90:11498-11502 (1993); Guzman et al., circ. 88:2838-2848 (1993); and Guzman et al., *Cir Res,* 73:1202-1207 (1993). Techniques for incorporating DNA into such expression systems are well known to those of ordinary skill in the art. The DNA can also be "naked," as described, for example, in published PCT Appl. No. WO 90/11092; and Ulmer et al., *Science,* 259:1745-1749 (1993), reviewed by Cohen, *Science,* 259:1691-1692 (1993). The uptake of naked DNA can be increased by coating the DNA onto biodegradable beads, which are efficiently transported into the cells.

VIII. Method of Treatment

The present invention provides a method of treating individuals suffering from leukemia. In such methods, the introduction of peptides, nucleic acids, protein binding agents, antigen presenting cells and/or immune effector cells as described above serves as an immunotherapeutic, directing and promoting the immune system of the individual to combat leukemic cells that display the CD19 or CD20 antigen fragments. The methods can comprise administering, through the means described above, an effective amount of any of the above compounds to a patient in need of such treatment. The methods can further comprise a course of chemotherapy, such as with 5-FU or cisplatin, prior to administration of the above compounds. See, e.g., Tanaka et al., *Int J Cancer,* 101:265 (2002).

Individuals at risk of developing cancers displaying CD19 and/or CD20, such as those having a genetic predisposition, can be treated with the formulations of the present invention in a prophylactic attempt to delay or eliminate the onset of the leukemic state. Those individuals who have already developed cancer and who have been treated to remove the cancer or are otherwise in remission are particularly susceptible to relapse and reoccurrence. As part of a treatment regimen, to combat a recurrence such individuals can be immunized against the cancer that they have been diagnosed as having had. Thus, once it is known that an individual has had a type of cancer and is at risk of a relapse, they can be immunized in order to prepare their immune system to combat any future appearance of the cancer.

Therapeutic approaches based upon the disclosure are premised on a response by a subject's immune system, which potentially leads to lysis of leukemia cells. One such therapeutic approach is the administration of autologous CTLs specific to the complex to a subject with abnormal cells of the phenotype at issue. It is within the skill of the artisan to develop such autologous CTLs in vitro. Specific production of a CTL is well known to one of ordinary skill in the art. Generally, a sample of cells taken from a subject, such as blood cells, are contacted with a cell presenting the complex and capable of provoking CTLs to proliferate. The target cell can be a transfectant. These transfectants present the desired complex on their surface and, when combined with a CTL of interest, stimulate the CTL's proliferation. The clonally expanded autologous CTLs can then be administered to the subject.

In one therapeutic methodology, referred to as adoptive transfer (Greenberg J, *Immunol,* 136(5):1917 (1986); Riddel et al., *Science,* 257:238 (1992); Lynch et al, *Eur J Immunol,* 21:1403-1410 (1991); Kast et al., *Cell,* 59:603-614 (1989)), cells presenting the desired complex are combined with CTLs thereby leading to proliferation of the CTLs specific. The proliferated CTLs are then administered to a subject with a cellular abnormality to the complex that may be characterized by certain of the abnormal cells presenting the particular complex. The CTLs can then lyse the abnormal cells, thereby achieving the desired therapeutic goal.

The foregoing therapy assumes that at least some of the subject's abnormal cells present the relevant HLA complex. This can be determined easily, as the art is familiar with methods for identifying cells presenting a particular HLA molecule. The art also encompasses methods of identifying cells expressing DNA of the pertinent sequences, in this case a leukemia associated gene sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a leukemia associated gene is being presented, and the subject is an appropriate candidate for the therapeutic approaches set forth herein.

Adoptive transfer is not the only form of therapy that is available in accordance with the invention. CTLs can also be provoked in vivo using a number of approaches. One approach is the use of non-proliferative cells expressing the relevant HLA complex, such as antigen presenting cells. The cells used in this approach can be those that normally express the complex, such as irradiated tumor cells or cells they can be transfected with one or both of the genes necessary for presentation of the complex. Chen et al., *Proc Natl Acad Sci USA,* 88:110-114 (1991), which exemplifies the transfected cell approach, shows the use of transfected cells expressing HPV E7 peptides in a therapeutic regime. In different embodiments, various cell types that express the complex can be used. Vectors carrying one or both of CD19 and/or CD20 can be used. Viral or bacterial vectors are especially preferred. In certain embodiments, the nucleic acid can be incorporated into an expression vector. Expression vectors can be unmodified extrachromosomal nucleic acids, plasmids or viral genomes constructed or modified to enable insertion of exogenous nucleic acids, such as those encoding the present peptides. Nucleic acids encoding these peptides can also be inserted into a retroviral genome, thereby facilitating integration of the nucleic acid into the genome of the target tissue or cell type. In these systems, the gene of interest is "carried" by carrier, e.g., a Vaccinia virus, retrovirus or the bacteria BCG, and the materials defacto "infect" host cells. The cells that result from this "infection" present the complex of interest, and are recognized by autologous CTLs, which then proliferate.

IX. Kits

The invention also provides isolated proteins and peptides, and antibodies to those proteins and peptides. Kits containing any of the foregoing molecules, alone or in combination, are additionally provided. The foregoing kits can be used in the diagnosis or treatment of conditions characterized by the expression of the present peptides. The kits can also be used to pulse antigen presenting cells or t-lymphocytes, and, as such, can contain appropriate culture media, culture media supplements such as cytokines, disposable laboratory equipment and the like. Examples of such kit components can be found in the following examples.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products. The notice may reflect approval by the agency of manufacture, use, or sale for human administration. In addition, the pharmaceutical compositions can be employed in conjunction with other therapeutic compounds.

The invention in another aspect involves a kit for detecting the presence of the expression of the present polypeptide.

Such kits employ two or more of the above-described nucleic acid molecules isolated in separate containers and packaged in a single package. In one such kit, a pair of isolated nucleic acid molecules is provided. In certain embodiments, the pair of isolated nucleic acid molecules are PCR primers.

The invention also embraces so-called expression kits, which allow the artisan to prepare a desired expression vector or vectors. Such expression kits include at least separate portions of each of the previously discussed coding sequences. Other components can be added, as desired, as long as the previously mentioned sequences, which are required, are included.

This invention is further illustrated by the following non-limiting examples.

EXAMPLES

Example 1

A total of 556 amino acids of CD19 protein, listed above as SEQ ID NO: 13, were retrieved from the SWISS-PROT databank and analyzed for HLA-A2.1 binding epitopes as nonamers by the peptide motif search software SYFPEITHI which is supported by DFG-Sonderforschungsbereich 510 and the European Union: EU BIOMED CT95-1627, BIO-TECH CT95-0263, and EU QLQ-CT-1999-00713. The algorithms used are based on the book MHC Ligands and Peptide Motifs, by H. G. Rammensee et al., Landes Bioscience, 1997. The prediction of the SYFPEITHI program is based on published motifs (pool sequencing, natural ligands) and the score is calculated by the consideration of specific amino acids of the peptide in a numeric value depending on whether the peptide is a carrying anchor, auxiliary anchor, or preferred residue. Ideal anchors are given 10 points, unusual anchors 6-8 points, auxiliary anchors 4-6 points and preferred residues 1-4 points. Amino acids that are regarded as having a negative effect on the binding are given values between −1 and −3. Besides a prediction for binding, the preferred amino acids in the peptide of CD19 antigen were examined for the possible immunogenic epitopes. Peptides are grouped based on overall score. As shown, the values for the tested CD19 peptides ranged from an overall high score of 29 to an overall low score of 10.

| Position | 1 | 2 | 3 | 4 | 5 | 6 | 7 | 8 | 9 | Score | SEQ ID NO. |
|---|---|---|---|---|---|---|---|---|---|---|---|
| 63 | K | L | S | L | G | L | P | G | L | 29 | 32 |
| 299 | Y | L | I | F | C | L | C | S | L | 29 | 33 |
| 5 | R | L | L | F | F | L | L | F | L | 27 | 1 |
| 284 | L | L | R | T | G | G | W | K | V | 26 | 34 |
| 296 | T | L | A | Y | L | I | F | C | L | 26 | 2 |
| 353 | S | L | P | T | P | T | S | G | L | 26 | 35 |
| 10 | L | L | F | L | T | P | M | E | V | 25 | 3 |
| 303 | C | L | C | S | L | V | G | I | L | 25 | 36 |
| 508 | Y | A | A | P | Q | L | H | S | I | 25 | 37 |
| 150 | K | L | M | S | P | K | L | Y | V | 24 | 4 |
| 310 | I | L | H | L | Q | R | A | L | V | 24 | 38 |
| 65 | S | L | G | L | P | G | L | G | I | 23 | 39 |
| 128 | D | L | G | G | L | G | C | G | L | 23 | 40 |
| 309 | G | I | L | H | L | Q | R | A | L | 23 | 41 |
| 245 | G | L | L | L | P | R | A | T | A | 22 | 42 |
| 300 | L | I | F | C | L | C | S | L | V | 22 | 43 |
| 6 | L | L | F | F | L | L | F | L | T | 21 | 44 |
| 70 | G | L | G | I | H | M | R | P | L | 21 | 45 |
| 74 | H | M | R | P | L | A | S | W | L | 21 | 46 |
| 279 | V | L | W | H | W | L | L | R | T | 21 | 47 |
| 505 | G | I | L | Y | A | A | P | Q | L | 21 | 48 |
| 27 | K | V | E | E | G | D | N | A | V | 20 | 49 |
| 183 | S | L | S | Q | D | L | T | M | A | 20 | 50 |
| 188 | L | T | M | A | P | G | S | T | L | 20 | 51 |
| 194 | S | T | L | W | L | S | C | G | V | 20 | 52 |
| 346 | N | Q | Y | G | N | V | L | S | L | 20 | 53 |
| 105 | K | A | W | Q | P | G | W | T | V | 19 | 54 |
| 190 | M | A | P | G | S | T | L | W | L | 19 | 55 |
| 238 | D | M | W | V | M | E | T | G | L | 19 | 56 |
| 266 | L | T | M | S | F | H | L | E | I | 19 | 57 |
| 271 | H | L | E | I | T | A | R | P | V | 19 | 58 |
| 292 | V | S | A | V | T | L | A | Y | L | 19 | 59 |
| 305 | C | S | L | V | G | I | L | H | L | 19 | 60 |
| 306 | S | L | V | G | I | L | H | L | Q | 19 | 61 |
| 502 | D | M | R | G | I | L | Y | A | A | 19 | 62 |
| 56 | S | P | L | K | P | F | L | K | L | 18 | 63 |
| 67 | G | L | P | G | L | G | I | H | M | 18 | 64 |
| 79 | A | S | W | L | F | I | F | N | V | 18 | 65 |
| 151 | L | M | S | P | K | L | Y | V | W | 18 | 66 |
| 220 | K | G | P | K | S | L | L | S | L | 18 | 67 |
| 224 | S | L | L | S | L | E | L | K | D | 18 | 68 |
| 240 | W | V | M | E | T | G | L | L | L | 18 | 69 |
| 302 | F | C | L | C | S | L | V | G | I | 18 | 70 |
| 20 | P | E | E | P | L | V | V | K | V | 17 | 71 |
| 50 | L | T | W | S | R | E | S | P | L | 17 | 72 |
| 113 | V | N | V | E | G | S | G | E | L | 17 | 73 |
| 179 | S | L | N | Q | S | L | S | Q | D | 17 | 74 |
| 197 | W | L | S | C | G | V | P | P | D | 17 | 75 |
| 246 | L | L | L | P | R | A | T | A | Q | 17 | 76 |
| 351 | V | L | S | L | P | T | P | T | S | 17 | 77 |

-continued

| Position | 1 | 2 | 3 | 4 | 5 | 6 | 7 | 8 | 9 | Score | SEQ ID NO. |
|---|---|---|---|---|---|---|---|---|---|---|---|
| 363 | R | A | Q | R | W | A | A | G | L | 17 | 78 |
| 467 | E | L | T | Q | P | V | A | R | T | 17 | 79 |
| 9 | F | L | L | F | L | T | P | M | E | 16 | 80 |
| 31 | G | D | N | A | V | L | Q | C | L | 16 | 81 |
| 34 | A | V | L | Q | C | L | K | G | T | 16 | 82 |
| 81 | W | L | F | I | F | N | V | S | Q | 16 | 83 |
| 107 | W | Q | P | G | W | T | V | N | V | 16 | 84 |
| 121 | L | F | R | W | N | V | S | D | L | 16 | 85 |
| 131 | G | L | G | C | G | L | K | N | R | 16 | 86 |
| 247 | L | L | P | R | A | T | A | Q | D | 16 | 87 |
| 287 | T | G | G | W | K | V | S | A | V | 16 | 88 |
| 293 | S | A | V | T | L | A | Y | L | I | 16 | 89 |
| 312 | H | L | Q | R | A | L | V | L | R | 16 | 90 |
| 370 | G | L | G | G | T | A | P | S | Y | 16 | 91 |
| 42 | T | S | D | G | P | T | Q | Q | L | 15 | 92 |
| 58 | L | K | P | F | L | K | L | S | L | 15 | 93 |
| 124 | W | N | V | S | D | L | G | G | L | 15 | 94 |
| 199 | S | C | G | V | P | P | D | S | V | 15 | 95 |
| 225 | L | L | S | L | E | L | K | D | D | 15 | 96 |
| 241 | V | M | E | T | G | L | L | L | P | 15 | 97 |
| 267 | T | M | S | F | H | L | E | I | T | 15 | 98 |
| 272 | L | E | I | T | A | R | P | V | L | 15 | 99 |
| 311 | L | H | L | Q | R | A | L | V | L | 15 | 100 |
| 318 | V | L | R | R | K | R | K | R | M | 15 | 101 |
| 360 | G | L | G | R | A | Q | R | W | A | 15 | 102 |
| 367 | W | A | A | G | L | G | G | T | A | 15 | 103 |
| 439 | Y | E | N | P | E | D | E | P | L | 15 | 104 |
| 484 | S | A | W | D | P | S | R | E | A | 15 | 105 |
| 494 | S | L | G | S | Q | S | Y | E | D | 15 | 106 |
| 12 | F | L | T | P | M | E | V | R | P | 14 | 107 |
| 17 | E | V | R | P | E | E | P | L | V | 14 | 108 |
| 18 | V | R | P | E | E | P | L | V | V | 14 | 109 |
| 23 | P | L | V | V | K | V | E | E | G | 14 | 110 |
| 28 | V | E | E | G | D | N | A | V | L | 14 | 111 |
| 35 | V | L | Q | C | L | K | G | T | S | 14 | 112 |
| 54 | R | E | S | P | L | K | P | F | L | 14 | 113 |
| 61 | F | L | K | L | S | L | G | L | P | 14 | 114 |
| 83 | F | I | F | N | V | S | Q | Q | M | 14 | 115 |
| 88 | S | Q | Q | M | G | G | F | Y | L | 14 | 116 |
| 95 | Y | L | C | Q | P | G | P | P | S | 14 | 117 |
| 143 | G | P | S | S | P | S | G | K | L | 14 | 118 |
| 148 | S | G | K | L | M | S | P | K | L | 14 | 119 |
| 158 | V | W | A | K | D | R | P | E | I | 14 | 120 |
| 166 | I | W | E | G | E | P | P | C | V | 14 | 121 |
| 187 | D | L | T | M | A | P | G | S | T | 14 | 122 |
| 189 | T | M | A | P | G | S | T | L | W | 14 | 123 |
| 217 | V | H | P | K | G | P | K | S | L | 14 | 124 |
| 274 | I | T | A | R | P | V | L | W | H | 14 | 125 |
| 276 | A | R | P | V | L | W | H | W | L | 14 | 126 |
| 286 | R | T | G | G | W | K | V | S | A | 14 | 127 |
| 289 | G | W | K | V | S | A | V | T | L | 14 | 128 |
| 391 | L | G | S | R | S | P | P | G | V | 14 | 129 |
| 468 | L | T | Q | P | V | A | R | T | M | 14 | 130 |
| 478 | F | L | S | P | H | G | S | A | W | 14 | 131 |
| 77 | P | L | A | S | W | L | F | I | F | 13 | 132 |
| 180 | L | N | Q | S | L | S | Q | D | L | 13 | 133 |
| 264 | G | N | L | T | M | S | F | H | L | 13 | 134 |
| 366 | R | W | A | A | G | L | G | G | T | 13 | 135 |
| 377 | S | Y | G | N | P | S | S | D | V | 13 | 136 |
| 383 | S | D | V | Q | A | D | G | A | L | 13 | 137 |
| 390 | A | L | G | S | R | S | P | P | G | 13 | 138 |
| 426 | N | L | G | Q | D | Q | L | S | Q | 13 | 139 |
| 460 | S | Y | E | N | E | D | E | E | L | 13 | 140 |
| 471 | P | V | A | R | T | M | D | F | L | 13 | 141 |
| 506 | I | L | Y | A | A | P | Q | L | H | 13 | 142 |
| 2 | P | P | P | R | L | L | F | F | L | 12 | 143 |
| 8 | F | F | L | L | F | L | T | P | M | 12 | 144 |
| 38 | C | L | K | G | T | S | D | G | P | 12 | 145 |
| 57 | P | L | K | P | F | L | K | L | S | 12 | 146 |
| 60 | P | F | L | K | L | S | L | G | L | 12 | 147 |
| 66 | L | G | L | P | G | L | G | I | H | 12 | 148 |
| 73 | I | H | M | R | P | L | A | S | W | 12 | 148 |
| 90 | Q | M | G | G | F | Y | L | C | Q | 12 | 149 |
| 118 | S | G | E | L | F | R | W | N | V | 12 | 150 |
| 120 | E | L | F | R | W | N | V | S | D | 12 | 151 |
| 127 | S | D | L | G | G | L | G | C | G | 12 | 152 |
| 135 | G | L | K | N | R | S | S | E | G | 12 | 153 |
| 172 | P | C | V | P | P | R | D | S | L | 12 | 154 |

| Position | 1 | 2 | 3 | 4 | 5 | 6 | 7 | 8 | 9 | Score | SEQ ID NO. |
|---|---|---|---|---|---|---|---|---|---|---|---|
| 207 | V | S | R | G | P | L | S | W | T | 12 | 155 |
| 218 | H | P | K | G | P | K | S | L | L | 12 | 156 |
| 227 | S | L | E | L | K | D | D | R | P | 12 | 157 |
| 236 | A | R | D | M | W | V | M | E | T | 12 | 158 |
| 239 | M | W | V | M | E | T | G | L | L | 12 | 159 |
| 258 | K | Y | Y | C | H | R | G | N | L | 12 | 160 |
| 283 | W | L | L | R | T | G | G | W | K | 12 | 161 |
| 295 | V | T | L | A | Y | L | I | F | C | 12 | 162 |
| 369 | A | G | L | G | G | T | A | P | S | 12 | 163 |
| 386 | Q | A | D | G | A | L | G | S | R | 12 | 164 |
| 424 | D | S | N | L | G | Q | D | Q | L | 12 | 165 |
| 498 | Q | S | Y | E | D | M | R | G | I | 12 | 166 |
| 499 | S | Y | E | D | M | R | G | I | L | 12 | 167 |
| 515 | S | I | R | G | Q | P | G | P | N | 12 | 168 |
| 16 | M | E | V | R | P | E | E | P | L | 11 | 169 |
| 49 | Q | L | T | W | S | R | E | S | P | 11 | 170 |
| 72 | G | I | H | M | R | P | L | A | S | 11 | 171 |
| 76 | R | P | L | A | S | W | L | F | I | 11 | 172 |
| 146 | S | P | S | G | K | L | M | S | P | 11 | 173 |
| 155 | K | L | Y | V | W | A | K | D | R | 11 | 174 |
| 165 | E | I | W | E | G | E | P | P | C | 11 | 175 |
| 195 | T | L | W | L | S | C | G | V | P | 11 | 176 |
| 201 | G | V | P | P | D | S | V | S | R | 11 | 177 |
| 206 | S | V | S | R | G | P | L | S | W | 11 | 178 |
| 222 | P | K | S | L | L | S | L | E | L | 11 | 179 |
| 243 | E | T | G | L | L | L | P | R | A | 11 | 180 |
| 260 | Y | C | H | R | G | N | L | T | M | 11 | 181 |
| 308 | V | G | I | L | H | L | Q | R | A | 11 | 182 |
| 316 | A | L | V | L | R | R | K | R | K | 11 | 183 |
| 325 | R | M | T | D | P | T | R | R | F | 11 | 184 |
| 343 | G | P | Q | N | Q | Y | G | N | V | 11 | 185 |
| 350 | N | V | L | S | L | P | T | P | T | 11 | 186 |
| 431 | Q | L | S | Q | D | G | S | G | Y | 11 | 187 |
| 464 | E | D | E | E | L | T | Q | P | V | 11 | 188 |
| 474 | R | T | M | D | F | L | S | P | H | 11 | 189 |
| 487 | D | P | S | R | E | A | T | S | L | 11 | 190 |
| 547 | G | G | R | M | G | T | W | S | T | 11 | 191 |
| 13 | L | T | P | M | E | V | R | P | E | 10 | 192 |
| 176 | P | R | D | S | L | N | Q | S | L | 10 | 193 |
| 209 | R | G | P | L | S | W | T | H | V | 10 | 194 |
| 216 | H | V | H | P | K | G | P | K | S | 10 | 195 |
| 251 | A | T | A | Q | D | A | G | K | Y | 10 | 196 |
| 265 | N | L | T | M | S | F | H | L | E | 10 | 197 |
| 275 | T | A | R | P | V | L | W | H | W | 10 | 198 |
| 277 | R | P | V | L | W | H | W | L | L | 10 | 199 |
| 317 | L | V | L | R | R | K | R | K | R | 10 | 200 |
| 328 | D | P | T | R | R | F | F | K | V | 10 | 201 |
| 344 | P | Q | N | Q | Y | G | N | V | L | 10 | 202 |
| 419 | E | F | Y | E | N | D | S | N | L | 10 | 203 |
| 492 | A | T | S | L | G | S | Q | S | Y | 10 | 204 |
| 512 | Q | L | H | S | I | R | G | Q | P | 10 | 205 |
| 542 | P | A | W | G | G | G | G | R | M | 10 | 206 |

A similar search for CD20 provided the following sequences:

| Position | 1 | 2 | 3 | 4 | 5 | 6 | 7 | 8 | 9 | Score | SEQ ID NO. |
|---|---|---|---|---|---|---|---|---|---|---|---|
| 188 | S | L | F | L | G | I | L | S | V | 32 | 6 |
| 127 | A | I | S | G | M | I | L | S | I | 27 | 7 |
| 64 | I | A | L | G | G | L | L | M | I | 25 | 205 |
| 68 | G | L | L | M | I | P | A | G | I | 24 | 206 |
| 87 | P | L | W | G | G | I | M | Y | I | 24 | 207 |
| 116 | K | M | I | M | N | S | L | S | L | 24 | 208 |
| 190 | F | L | G | I | L | S | V | M | L | 24 | 209 |
| 198 | L | I | F | A | F | F | Q | E | L | 24 | 210 |
| 56 | Q | I | M | N | G | L | F | H | I | 23 | 211 |
| 92 | I | M | Y | I | I | S | G | S | L | 23 | 212 |
| 130 | G | M | I | L | S | I | M | D | I | 23 | 234 |
| 241 | E | I | K | E | E | V | V | G | L | 23 | 214 |
| 95 | I | I | S | G | S | L | L | A | A | 22 | 215 |
| 123 | S | L | F | A | A | I | S | G | M | 22 | 216 |
| 22 | A | M | Q | S | G | P | K | P | L | 21 | 217 |

-continued

| Position | 1 | 2 | 3 | 4 | 5 | 6 | 7 | 8 | 9 | Score | SEQ ID NO. |
|---|---|---|---|---|---|---|---|---|---|---|---|
| 135 | I | M | D | I | L | N | I | K | I | 21 | 218 |
| 185 | S | I | Q | S | L | F | L | G | I | 21 | 219 |
| 29 | P | L | F | R | R | M | S | S | L | 20 | 220 |
| 76 | I | Y | A | P | I | C | V | T | V | 20 | 221 |
| 131 | M | I | L | S | I | M | D | I | L | 20 | 222 |
| 154 | F | I | R | A | H | T | P | Y | I | 20 | 8 |
| 193 | I | L | S | V | M | L | I | F | A | 20 | 223 |
| 238 | Q | T | I | E | I | K | E | E | V | 20 | 224 |
| 36 | S | L | V | G | P | T | Q | S | F | 19 | 225 |
| 57 | I | M | N | G | L | F | H | I | A | 19 | 226 |
| 65 | A | L | G | G | L | L | M | I | P | 19 | 227 |
| 75 | G | I | Y | A | P | I | C | V | T | 19 | 228 |
| 94 | Y | I | I | S | G | S | L | L | A | 19 | 229 |
| 70 | L | M | I | P | A | G | I | Y | A | 18 | 230 |
| 99 | S | L | L | A | A | T | E | K | N | 18 | 231 |
| 138 | I | L | N | I | K | I | S | H | F | 18 | 232 |
| 147 | L | K | M | E | S | L | N | F | I | 18 | 10 |
| 151 | S | L | N | F | I | R | A | H | T | 18 | 9 |
| 206 | L | V | I | A | G | I | V | E | N | 18 | 233 |
| 239 | T | I | E | I | K | E | E | V | V | 18 | 234 |
| 33 | R | M | S | S | L | V | G | P | T | 17 | 235 |
| 50 | K | T | L | G | A | V | Q | I | M | 17 | 236 |
| 53 | G | A | V | Q | I | M | N | G | L | 17 | 237 |
| 61 | L | F | H | I | A | L | G | G | L | 17 | 238 |
| 63 | H | I | A | L | G | G | L | L | M | 17 | 239 |
| 118 | I | M | N | S | L | S | L | F | A | 17 | 240 |
| 125 | F | A | A | I | S | G | M | I | L | 17 | 241 |
| 133 | L | S | I | M | D | I | L | N | I | 17 | 242 |
| 134 | S | I | M | D | I | L | N | I | K | 17 | 243 |
| 186 | I | Q | S | L | F | L | G | I | L | 17 | 244 |
| 207 | V | I | A | G | I | V | E | N | E | 17 | 245 |
| 71 | M | I | P | A | G | I | Y | A | P | 16 | 246 |
| 72 | I | P | A | G | I | Y | A | P | I | 16 | 247 |
| 111 | C | L | V | K | G | K | M | I | M | 16 | 248 |
| 144 | S | H | F | L | K | M | E | S | L | 16 | 11 |
| 191 | L | G | I | L | S | V | M | L | I | 16 | 249 |
| 47 | R | E | S | K | T | L | G | A | V | 15 | 250 |
| 121 | S | L | S | L | F | A | A | I | S | 15 | 251 |
| 139 | L | N | I | K | I | S | H | F | L | 15 | 252 |
| 181 | Q | Y | C | Y | S | I | Q | S | L | 15 | 253 |
| 203 | F | Q | E | L | V | I | A | G | I | 15 | 254 |
| 222 | R | P | K | S | N | I | V | L | L | 15 | 255 |
| 228 | V | L | L | S | A | E | E | K | K | 15 | 256 |
| 60 | G | L | F | H | I | A | L | G | G | 14 | 257 |
| 62 | F | H | I | A | L | G | G | L | L | 14 | 258 |
| 69 | L | L | M | I | P | A | G | I | Y | 14 | 259 |
| 84 | V | W | Y | P | L | W | G | G | I | 14 | 260 |
| 91 | G | I | M | Y | I | I | S | G | S | 14 | 261 |
| 96 | I | S | G | S | L | L | A | A | T | 14 | 262 |
| 120 | N | S | L | S | L | F | A | A | I | 14 | 263 |
| 161 | Y | I | N | I | Y | N | C | E | P | 14 | 264 |
| 189 | L | F | L | G | I | L | S | V | M | 14 | 265 |
| 199 | I | F | A | F | F | Q | E | L | V | 14 | 266 |
| 200 | F | A | F | F | Q | E | L | V | I | 14 | 267 |
| 220 | C | S | R | P | K | S | N | I | V | 14 | 268 |
| 257 | K | N | E | E | D | I | E | I | I | 14 | 269 |
| 16 | P | M | K | G | P | I | A | M | Q | 13 | 270 |
| 44 | F | F | M | R | E | S | K | T | L | 13 | 271 |
| 49 | S | K | T | L | G | A | V | Q | I | 13 | 272 |
| 74 | A | G | I | Y | A | P | I | C | V | 13 | 273 |
| 80 | I | C | V | T | V | W | Y | P | L | 13 | 274 |
| 88 | L | W | G | G | I | M | Y | I | I | 13 | 275 |
| 100 | L | L | A | A | T | E | K | N | S | 13 | 276 |
| 114 | K | G | K | M | I | M | N | S | L | 13 | 277 |
| 117 | M | I | M | N | S | L | S | L | F | 13 | 278 |
| 142 | K | I | S | H | F | L | K | M | E | 13 | 279 |
| 156 | R | A | H | T | P | Y | I | N | I | 13 | 280 |
| 201 | A | F | F | Q | E | L | V | I | A | 13 | 281 |
| 210 | G | I | V | E | N | E | W | K | R | 13 | 282 |
| 224 | K | S | N | I | V | L | L | S | A | 13 | 283 |
| 226 | N | I | V | L | L | S | A | E | E | 13 | 284 |
| 229 | L | L | S | A | E | E | K | K | E | 13 | 285 |
| 30 | L | F | R | R | M | S | S | L | V | 12 | 286 |
| 58 | M | N | G | L | F | H | I | A | L | 12 | 287 |
| 93 | M | Y | I | I | S | G | S | L | L | 12 | 288 |
| 124 | L | F | A | A | I | S | G | M | I | 12 | 289 |
| 132 | I | L | S | I | M | D | I | L | N | 12 | 290 |
| 192 | G | I | L | S | V | M | L | I | F | 12 | 291 |

-continued

| Position | 1 | 2 | 3 | 4 | 5 | 6 | 7 | 8 | 9 | Score | SEQ ID NO. |
|---|---|---|---|---|---|---|---|---|---|---|---|
| 196 | V | M | L | I | F | A | F | F | Q | 12 | 292 |
| 204 | Q | E | L | V | I | A | G | I | V | 12 | 293 |
| 221 | S | R | P | K | S | N | I | V | L | 12 | 294 |
| 231 | S | A | E | E | K | K | E | Q | T | 12 | 295 |
| 232 | A | E | E | K | K | E | Q | T | I | 12 | 296 |
| 248 | G | L | T | E | T | S | S | Q | P | 12 | 297 |
| 264 | I | I | P | I | Q | E | E | E | E | 12 | 298 |
| 7 | S | V | N | G | T | F | P | A | E | 11 | 299 |
| 45 | F | M | R | E | S | K | T | L | G | 11 | 300 |
| 101 | L | A | A | T | E | K | N | S | R | 11 | 301 |
| 110 | K | C | L | V | K | G | K | M | I | 11 | 302 |
| 137 | D | I | L | N | I | K | I | S | H | 11 | 303 |
| 141 | I | K | I | S | H | F | L | K | M | 11 | 304 |
| 146 | F | L | K | M | E | S | L | N | F | 11 | 305 |
| 163 | N | I | Y | N | C | E | P | A | N | 11 | 306 |
| 183 | C | Y | S | I | Q | S | L | F | L | 11 | 307 |
| 197 | M | L | I | F | A | F | F | Q | E | 11 | 308 |
| 242 | I | K | E | E | V | V | G | L | T | 11 | 309 |
| 262 | I | E | I | I | P | I | Q | E | E | 11 | 310 |
| 263 | E | I | I | P | I | Q | E | E | E | 11 | 311 |
| 3 | T | P | R | N | S | V | N | G | T | 10 | 312 |
| 13 | P | A | E | P | M | K | G | P | I | 10 | 313 |
| 21 | I | A | M | Q | S | G | P | K | P | 10 | 314 |
| 51 | T | L | G | A | V | Q | I | M | N | 10 | 315 |
| 77 | Y | A | P | I | C | V | T | V | W | 10 | 316 |
| 83 | T | V | W | Y | P | L | W | G | G | 10 | 317 |
| 90 | G | G | I | M | Y | I | I | S | G | 10 | 318 |
| 126 | A | A | I | S | G | M | I | L | S | 10 | 319 |
| 128 | I | S | G | M | I | L | S | I | M | 10 | 320 |
| 225 | S | N | I | V | L | L | S | A | E | 10 | 321 |
| 227 | I | V | L | L | S | A | E | E | K | 10 | 322 |
| 234 | E | K | K | E | Q | T | I | E | I | 10 | 323 |
| 254 | S | Q | P | K | N | E | E | D | I | 10 | 324 |
| 256 | P | K | N | E | E | D | I | E | I | 10 | 325 |

As shown, the values for the tested CD20 peptides ranged from an overall high score of 32 to an overall low score of 10.

Based on high HLA-A2.1 binding scores, several 9 mer fragments of the CD19 peptide (SEQ ID NO: 13) or CD20 peptide (SEQ ID NO: 14) were identified using SYFPEITHI software and are listed above. The score demonstrates the calculated potential capability for binding to a HLA-A2 molecule.

The following peptides were tested for their ability to bind to HLA-A2.1+T2 cells and their binding scores under Brefeldin A treatment were evaluated. Tourdot at al., *Eur J Immunol*, 30:3411-3421 (2000). This experiment was performed to measure the peptide/HLA-A2.1 complex stability using the native or modified CD19 or CD20 peptides. As the immunogenicity of a peptide depends primarily on its capacity to stabilize the HLA-A2.1 molecules, a peptide that greatly stabilizes HLA-A2.1 could generate more effective cytotoxic T cells that recognize leukemia cells.

T2 cells, a transporter antigen processing (TAP) gene-deficient cell line that express only HLA-A2.1 MHC class I molecules (Zweerink H J et al., *J Immunol*, 150:1763-1771 (1993)), were used to evaluate CD19 or CD20 peptide specific binding to HLA-A2.1. HLA-A2.1-specific influenza virus matrix peptide 58-66 (GILGFVFTL, SEQ ID NO: 31), which is known to bind very tightly to HLA-A2.1, was used as an HLA-A2.1-specific control peptide.

Peptide Synthesis

The peptides set forth in the table below were synthesized by standard fmoc (9-fluorenylmethyl-oxycarbonyl) chemistries and were purified to >90% using reverse-phase chromatography (Biosynthesis, Lewisville, Tex.). A HLA-A2.1-specific influenza virus protein matrix peptide (GILGFVFTL: residues 58-66, SEQ ID NO: 31) was synthesized and used as a positive control in these studies. The identity of each peptide was validated by measuring mass-spectrometry for molecular weight.

| | | Brefeldin A treatment | | | | | |
|---|---|---|---|---|---|---|---|
| | Peptide Sequence | None | 0 hr | 2 hr | 4 hr | 6 hr | Overnight |
| T2 alone | | 215 | 226 | 200 | 187 | 157 | 255 |
| T2 plus influenza virus peptide | | | | | | | |
| SEQ ID NO: 31 | GILGFVFTL | 605 | 807 | 897 | 909 | 759 | 504 |
| | CD19 | | | | | | |
| SEQ ID NO: 1 | RLLFFLLFL | N/A | 167 | 202 | 174 | 152 | 248 |
| SEQ ID NO: 2 | TLAYLIFCL | 363 | 530 | 608 | 513 | 387 | 312 |
| SEQ ID NO: 3 | LLFLTPMEV | 556 | 770 | 924 | 880 | 573 | 453 |
| SEQ ID NO: 4 | KLMSPKLYV | 600 | 683 | 759 | 796 | 642 | 540 |
| SEQ ID NO: 5 | LLFFLLFLV | 164 | 200 | 202 | 163 | 143 | 200 |

-continued

| | Peptide Sequence | None | Brefeldin A treatment | | | | Overnight |
| --- | --- | --- | --- | --- | --- | --- | --- |
| | | | 0 hr | 2 hr | 4 hr | 6 hr | |
| | CD20 | | | | | | |
| SEQ ID NO: 6 | SLFLGILSV | 637 | 672 | 703 | 762 | 770 | 410 |
| SEQ ID NO: 7 | AISGMILSI | 162 | 220 | 256 | 165 | 144 | 232 |
| SEQ ID NO: 8 | FIRAHTPYI | 167 | 232 | 215 | 192 | 154 | 250 |
| SEQ ID NO: 9 | SLNFIRAHT | 172 | 212 | 200 | 180 | 128 | 195 |
| SEQ ID NO: 10 | LKMESLNFI | 215 | 245 | 291 | 227 | 190 | 225 |
| SEQ ID NO: 11 | SHFLKMESL | 172 | 216 | 218 | 199 | 127 | 277 |

As can be seen from these results, the peptides of SEQ ID NOS: 2, 3, 4 and 6 gave good and prolonged stable binding. Several other peptides provided good initial binding over baseline values.

Example 2

The present example illustrates that that the peptides of the invention are capable of inducing a T-lymphocyte response. FIG. 1 is a timeline of events performed for the generation of CD20 peptide-specific cytotoxic T-lymphocytes. A similar timeline can be used to produce CD19 peptide-specific cytotoxic T lymphocytes. CD19 or CD20 peptide-specific cytotoxic T lymphocytes were generated by stimulating T lymphocytes from HLA-A2+ normal donors with dendritic cells pulsed with a peptide of interest. In this and the following examples, antigen presenting cells were pulsed at 150 micrograms of the peptide per 1 million antigen presenting cells with SLFLGILSV (SEQ ID NO: 6). CD19 peptide specific cytotoxic T-lymphocytes were generated by contacting TLAYLIFCL (SEQ ID NO: 2), KLMSPKLYV (SEQ ID NO: 4), or LLFLTPMEV (SEQ ID NO: 3) with the cytotoxic T-lymphocytes once per week for 4 to 5 weeks.

Other peptides that include the sequences listed above can be similarly tested by the skilled artisan in the course of normal experimentation to determine whether peptides including any of the recited sequences can be effectively used as described herein.

Figure 2A:
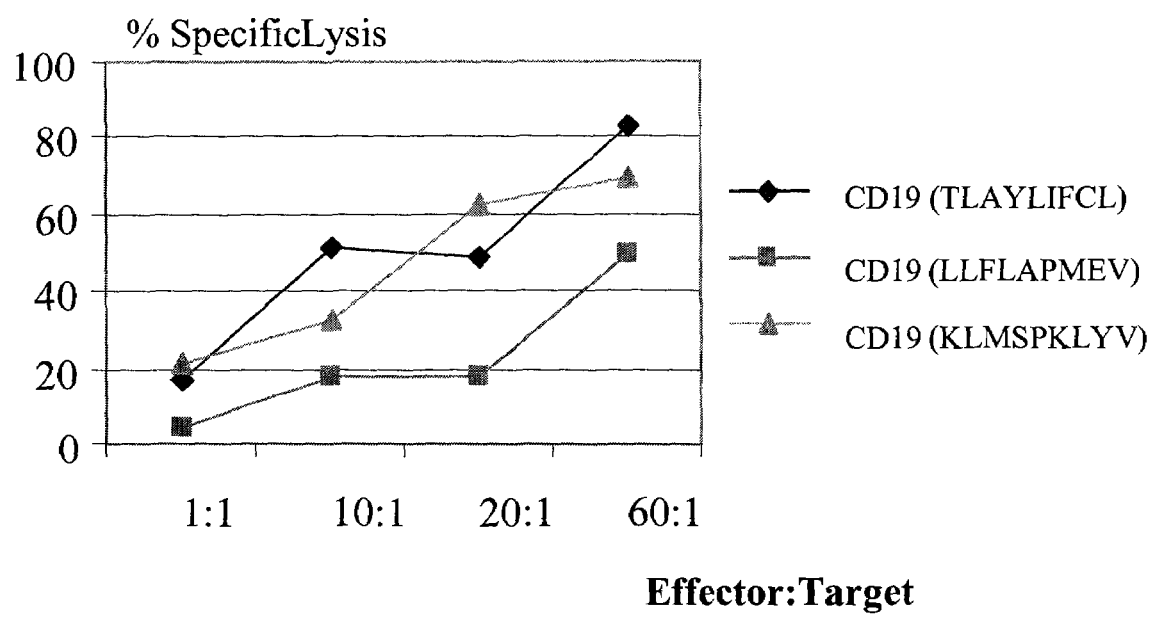
FIGS. 2a and 2b show the cytotoxic activity of CD19 and CD20 peptide-specific CTLs against ST486 (Burkett's lymphoma cell line)
Figure 2B:
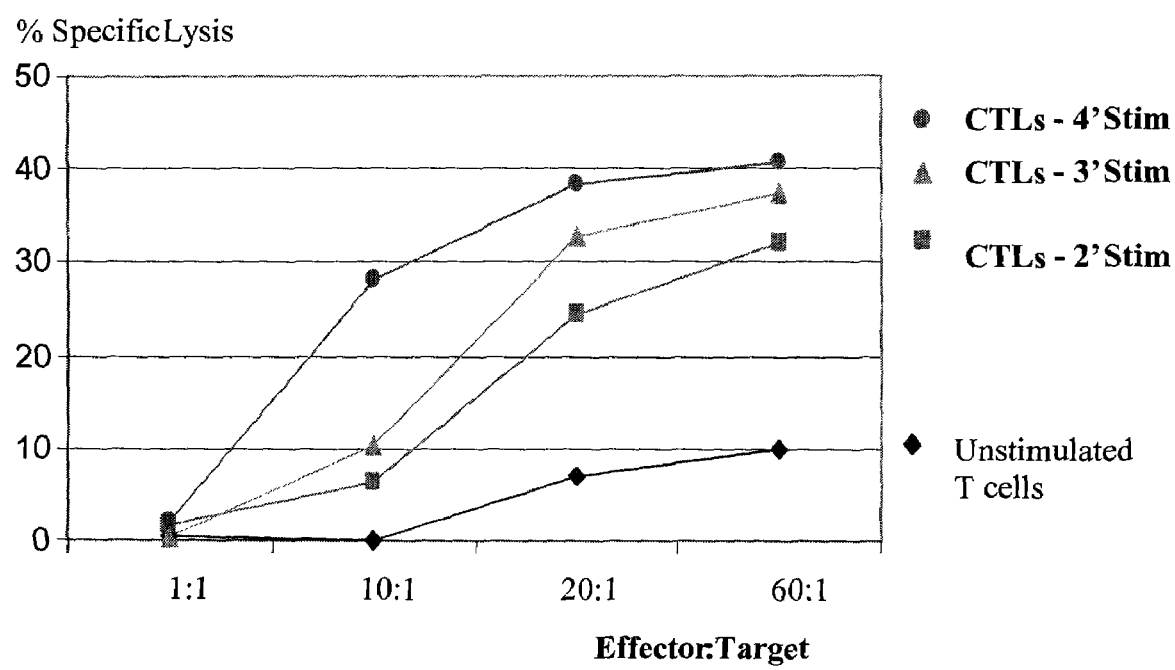
Figure 3:
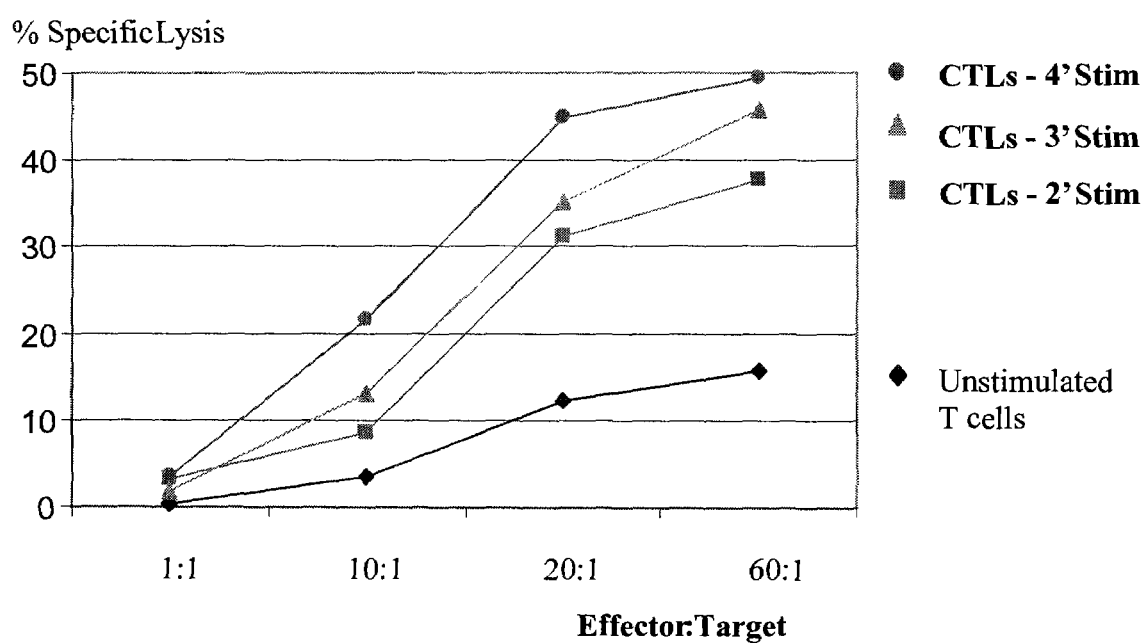
FIG. 3 shows the cytotoxic activity of CD20 peptide-specific CTLs to IFN-γ/TNF-α treated ST486 cells.
Figure 4:
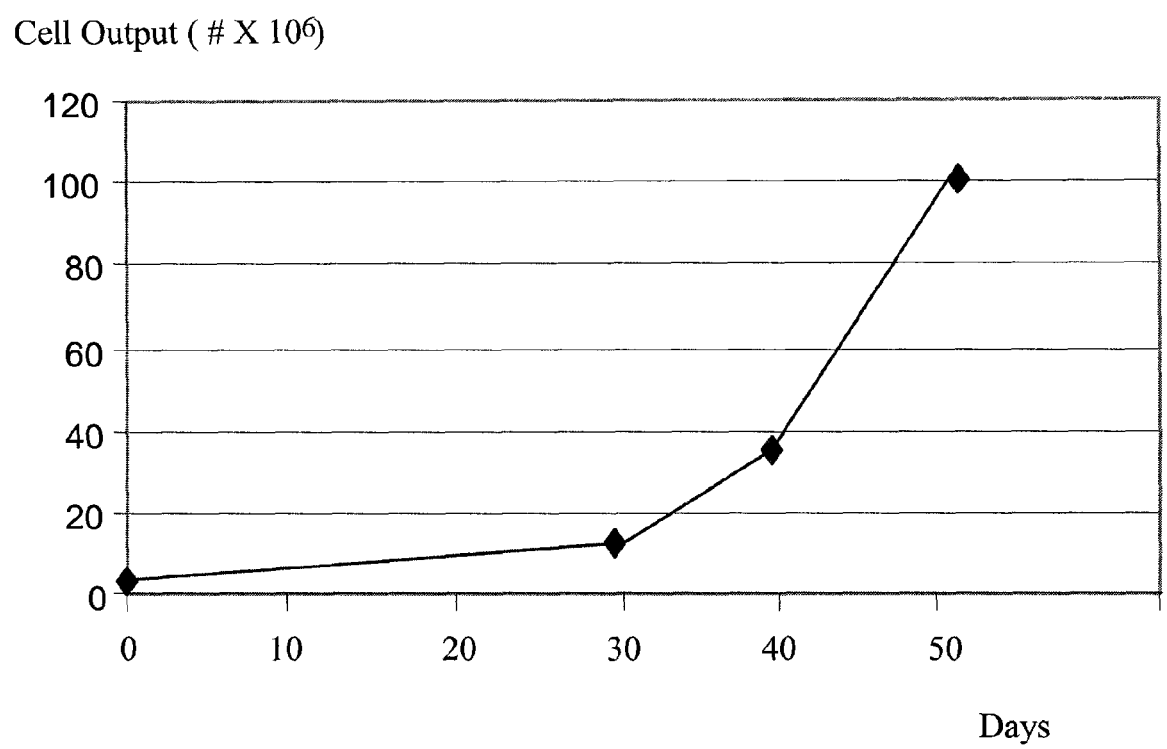
FIG. 4 shows the expansion of CD20 peptide specific cytotoxic T-lymphocytes over time using CD3/CD28 beads and IL-2.
Figure 5:
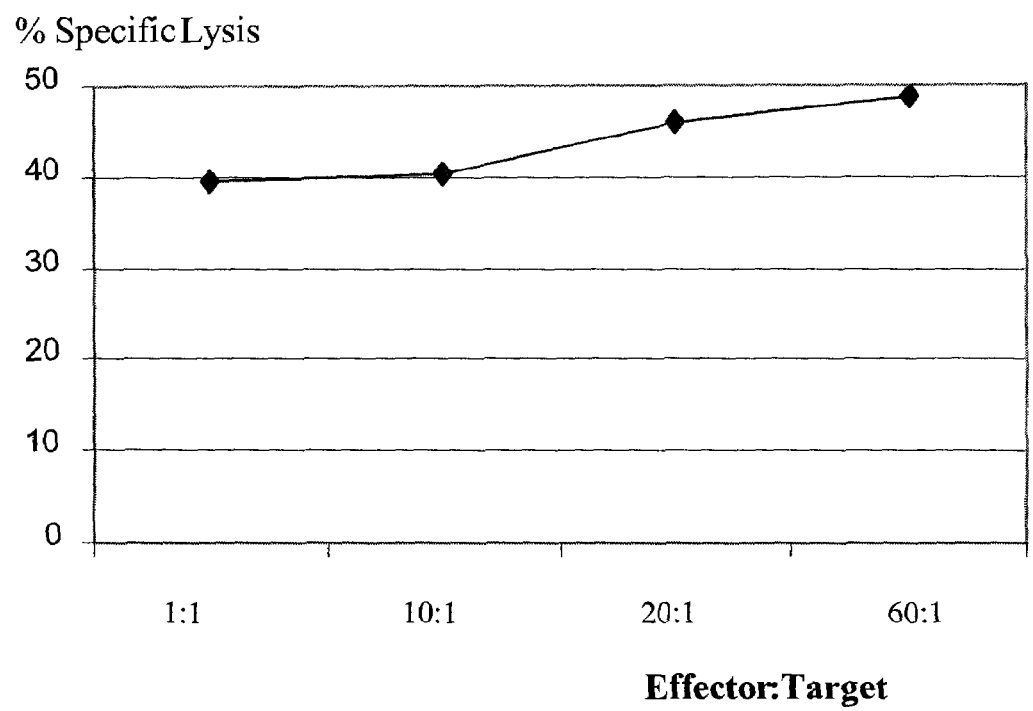
FIG. 5 shows the cytotoxic activity of expanded CD20 peptide specific cytotoxic T-lymphocytes to ST486 at different effector:target cell ratios.

The antigen presenting cells were stimulated one to four times by contacting them with effector cells at different effector:target cell ratios. The effector cells were then contacted with HLA-A2.1 positive ST486 cells and the cytotoxicity to the ST486 cells were measured. ST486 cells are Burkett's lymphoma cells which are HLA-A2.1 positive. The ratios of target: effectorized were 1:1, 10:1, 20:1, and 60:1. The results for CD19 peptide specific cytotoxic T-lymphocytes are set forth in FIG. 2a. The results for CD20 peptide specific cytotoxic T-lymphocytes are shown in FIG. 2b and FIG. 3. FIG. 4 shows the expansion of CD20 peptide specific cytotoxic T-lymphocytes over time using CD3/CD28 beads and IL-2. FIG. 5 shows the cytotoxic activity of expanded CD20 peptide specific cytotoxic T-lymphocytes to ST486 at different effector:target cell ratios. FIGS. demonstrate that the expanded cytotoxic T-lymphocytes retain their cytotoxic activity after expansion. CTLs were expanded in AIM-V media containing CD3/CD28 beads to stimulate T cells and IL-2 to proliferate CTLs at cell density of 0.5-0.0×10$^6$ cells/ml.

Cell Lines

A ST486 cell line, purchased from American Tissue Culture Collection (ATCC) was maintained in liquid culture in RPMI 1640 and 10% fetal calf serum (FCS; Biowhittaker, Walkersville, Md.). T2 cells, a human B and T cell hybrid expressing HLA-A2.1, were maintained in RPMI 1640 plus 20% FCS and used as antigen presenting cells in these studies.

MHC Peptide Binding Assay

The assay for peptide binding to HLA-A2.1 was performed (Nijman H W et al., *Eur J Immunol*, 23:1215-1219 (1993)) using the TAP-deficient T2 hybrid cell line, which is known to up-regulate HLA-A2.1 expression on the cell surface by acquiring only exogenous epitope (Salter et al. *EMBO J*, 5:943-949 (1986); Zweerink H J et al., *J Immunol*, 150:1763-1771 (1993)). T2 cells were washed and resuspended in serum-free AIM-V™ (Gibco-Life Technologies, Rockville, Md.) at a final concentration of 1×10$^6$ cells/ml and transferred into a 24-well tissue culture plate. Cells were pulsed with respective CD19 or CD20 peptides at different concentrations (5-150 µg/ml) or HLA-A2.1-specific influenza virus protein matrix peptide (30 µg/ml) plus 3 µg human β2-microglobulin (Sigma), and incubated for overnight at 37° C., 5% $CO_2$ in humidified air. After incubation, cells were washed once with PBS containing 3% FCS, and stained with mouse anti-HLA-A2.1 monoclonal antibody for 15 minutes at 4° C. After washing, the cells were incubated with goat anti-mouse IgG (F(ab')2)-FITC for 15 minutes at 4° C. The cells were washed once, and fluorescence was measured on a FACSort™ flow cytometer (Becton Dickson, San Jose, Calif.). The fluorescence index was calculated as follows: (mean channel fluorescence of sample−mean channel fluorescence of unstained control cells)/mean channel fluorescence of unstained control cells.

Cell Isolation

Peripheral blood mononuclear cells (PBMCs) were isolated from heparinized whole blood of healthy HLA-A2.1+ donors by standard gradient centrifugation with Ficoll-Paque™ Plus (Amersham Pharmacia Biotech AB, Uppsala, Sweden). PBMCs were harvested from the interface, washed twice, and resuspended in PBS supplemented with 5 mM EDTA and 0.5% human serum albumin. Informed consent was obtained from all donors and the protocol was approved by the Rush Medical School Institutional Review Board.

CD14+ monocytes were separated from the isolated PBMCs using a magnetic sorting technique (Miltenyi Biotec, Auburn, Calif.). PBMCs were incubated with colloidal superparamagnetic microbeads conjugated with anti-human CD14 mAb for 15 minutes at 4° C., and passed over a column in a magnetic field. After washing, positively enriched CD14+ cells were eluted from the magnetic columns. Purity (mean±standard deviation) of CD14+ monocytes was examined by flow cytometry and was found to be 92±4%.

CD3+ T cells were isolated from the monocyte depleted cell fractions using the Pan T cell isolation kit from Miltenyi Biotec (Auburn, Calif.). The T cell isolation was done by depletion of B cells, NK cells, early erythroid cells, platelets and basophils by indirectly labeling with a cocktail of haptenconjugated CD11b, CD16, CD19, CD36 and CD56 antibodies, and MACS® microbeads (Miltenyi Biotech) coupled to an anti-hapten monoclonal antibody. The effluent (negative fraction cells) was collected from the column as the enriched CD3+ T cell fraction. Purity (mean±standard deviation) of CD3+ T cells was examined by flow cytometry and was found to be 94±4%.

Dendritic Cell (DC) Generation.

Immature DCs can be generated according to modified protocols of Romani N, et al., *J Exp Med*, 180:83-89 (1994); and Bakker et al., *Cancer Res*, 55:5330-5334 (1995). Briefly, fresh or frozen/thawed CD14+ cells are cultured in RPMI 1640 medium (Gibco-Life Technologies, Gaithersburg, Md.) supplemented with 10% FCS, 1,000 U/ml GM-CSF and 1,000 U/ml IL-4. The cell cultures are fed with fresh medium and GM-CSF and IL-4 every other day and cell differentiation is monitored by light microscopy. On day 7, the cultures are supplemented with different combinations of DC maturation factors such as lipopolysaccharide (100 U/ml), TNF-α (10 ng/ml), or IFN-α (1,000 U/ml) plus TNF-α (10 ng/ml). After three days of incubation, mature DCs (mDC) are harvested and their phenotypes are evaluated by flow cytometry. The maturation factor(s) yielding optimal DC maturation are determined and used to generate mDCs for peptide pulsing in upcoming studies.

Induction of Peptide-Specific CTLs.

Two different types of antigen-presenting cells (APCs), mDCs and T2 cells, are used to generate CD19 or CD20 peptide-specific CTLs. APCs are washed three times in serum-free AIM-V™ culture media and pulsed with peptide at 150 μg/ml in the media overnight. The peptide-loaded APCs are then irradiated at 10 Gy, washed once, and resuspended in RPMI 1640 media supplemented with 10% human AB serum (Biowhittaker, Walkersville, Md.). Peptide-pulsed APCs are used to prime autologous CD3+ T cells at a 1:20 stimulator-to-responder cell ratio in RPMI 1640 media supplemented with 10% human AB serum, 5 ng/ml IL-6, 20 ng/ml IL-7, and 1 ng/ml IL-12. CTL cultures are restimulated weekly for a total of 4 cycles of stimulation. IL-2 (50 U/ml) is added to the culture one day after the third stimulation and the cells are fed three times a week with fresh medium containing the cytokines.

Cytotoxicity Assay

The cytolytic activity of the CD19 or CD20 peptide-specific CTLs is measured in a standard $^{51}$Cr-release assay. The CTLs (effector cells) are seeded with $^{51}$Cr-labeled 5×10$^3$ lymphoma cells (target cells) per well at various effector: target cell ratios in 96-well U-bottom microtiter plates and incubated for 4 hours at 37° C., 5% CO$_2$. After the incubation, the supernatants (100 ul) are harvested and the specific $^{51}$Cr-release is measured using a Beckman LS6500 liquid scintillation counter (Beckman Coulter, Brea, Calif.). The percent specific cell lysis is calculated as [(experimental release−spontaneous release)÷(maximum release−spontaneous release)]. Maximum release is determined from detergent-releasable target cell counts and spontaneous release is determined from the target cell counts in the absence of CTLs.

Cold Target Inhibition Assays

Antigen-specific lysis is evaluated in a cold target inhibition assay by analyzing the capacity of unlabeled lymphoma cells to block lysis of $^{51}$Cr-labeled lymphoma cells. Effector cells are incubated with an equal number of the unlabeled "cold" target cells (ML-2) for 1 hour at 37° C., 5% CO$_2$ before the addition of $^{51}$Cr-labeled "hot" lymphoma target cells. Although ML-2 cells, a human, peripheral blood, acute myelomonocytic leukemia cell line are used in certain experiments of the invention, the skilled artisan understands that alternative cell lines may be used with the invention. After a 4-hour incubation, the supernatants (100 ul) are harvested and the specific $^{51}$Cr-release is measured. The inhibition of lymphoma-specific lysis is measured by comparing the percent cytotoxicity of the effector cells incubated with or without the unlabeled "cold" target cells.

IFN-γ Release by CD19 or CD20 Peptide-Specific CTLs

IFN-γ release by the CTLs is measured using an IFN-γ ELISA kit (PBL-Biomedical Lab., Piscataway, N.J.). Briefly, IFN-γ standards or the supernatant from CD19 or CD20 peptide-specific CTL cultures are transferred into a 96-well plate pre-coated with anti-human IFN-γ capture monoclonal antibody and incubated for 1 hour in a closed chamber at 24° C. After washing the plate with PBS/0.05% Tween 20, anti-human IFN-γ antibody is added to the wells and incubated for 1 hour at 24° C. Wells are then developed by incubation with horseradish peroxidase conjugate and TMB substrate solution. Stop solution is added to each well and the absorbance is determined at 450 nm with a SpectraMAX Plus plate reader (Stratagene, La Jolla, Calif.). The amount of cytokine present in the CTL culture supernatant is calculated based on the IFN-γ standard curve.

Phenotypic Analysis of CD19 or CD20 Peptide-Specific CTLs

CTLs are stained with anti-CD8-FITC, —CD45RA-FITC or -CD28-PE, -CD45RO-PE, or -CD69-PE monoclonal antibodies for 15 minutes at 4° C. After incubation, the cells are washed and analyzed by flow cytometry. Live gating of the forward and scatter channels is used to exclude debris and to selectively acquire the lymphocyte population for analysis. Individual fluorescence data are determined using CellQuest™ v2.1 acquisition and analysis software (Becton Dickinson, Franklin Lakes, N.J.).

Peptide-MHC Tetramer Staining

A Streptavidin-PE-labeled HLA-2.1/peptide tetramer is produced, using either provided peptide or provided sequence, to Beckman Coulter (Fullerton, Calif.) using the methods described by Altman J D et al., *Science*, 274:94-96 (1996). Two-color flow cytometry assays are performed by stainings with anti-CD8-FITC and tetramer-PE. Briefly, the CTLs (2×10$^5$ cells) are stained with 300 ng of tetramer and incubated for 30 minutes at 37° C. After a washing, the cells are stained with anti-CD8-FITC mAb for 15 minutes at 4° C. Cells are washed and analyzed by flow cytometry.

RESULTS

Identification of HLA-A2.1-Specific CD19 or CD20 Epitope

The results, expressed as the Fluorescence Index (HLA-A2.1 mean channel fluorescence T2 cells pulsed with β2 microglobulin and CD19 or CD20 peptide÷HLA-A2.1 mean channel fluorescence T2 cells pulsed with β2 microglobulin) are used to select the best HLA-A2.1 binding peptide. A Fluorescence Index (FI) of >1.0 indicates the up-regulation of HLA-A2.1 molecules by peptide binding on the surface of T2 cells. Based on these results, the specific peptides are chosen for evaluation as a potential immunogenic epitope for use in generating peptide-specific CTLs against target cells.

Dendritic and T2 Cells as Antigen Presenting Cells

In this example, immature DCs obtained by the culture of CD14+ monocytes with GM-CSF (1,000 U/ml) and IL-4 (1,000 U/ml) are induced to undergo maturation by incubation with LPS (100 Units/ml), TNF-α (10 ng/ml) or TNF-α (10 ng/ml)+IFN-γ (50 ng/ml) during the final three days of the culture period. Flow cytometric analysis of the respective DC cultures shows a phenotypic profile characterized by high expression of CD40, CD80, CD83, and/or CD86. HLA-DR and no expression of CD3 or CD14 (data not shown). The highest up-regulation of the co-immunostimulatory (CD80 and CD86) and HLA-A2.1 MHC class I molecules is detected on DCs treated with TNF-α+IFN-γ (Table 5). LPS or TNF-α alone also induced the high expression of CD80, CD86 and HLA-A2.1 molecules compared to the GM-CSF+IL-4 (immature DC) control group. However, this up-regulation was not as high as seen with the TNF-α+IFN-γ treated combination.

The phenotype of the T2 cell line is evaluated to determine its potential for use as an alternative type of antigen presenting cell. The results (Table 4) show that T2 cells express high levels of co-immunostimulatory and HLA-A2.1 molecules. The expression levels of CD83 and CD86 molecules on T2 cells are comparable to those observed on mDCs (Table 4). The expression of CD80 is higher on T2 cells compared to mDCs. The phenotypic profiles of both the mDCs and T2 cells make them ideal candidates for use as antigen presenting cells in the generation of CD19 or CD20 peptide-specific CTLs.

TABLE 4

Phenotypic analysis of mature dendritic (mDC) and T2 antigen-presenting cells.

| | HLA-A2.1 | CD80 | CD86 | CD83 |
|---|---|---|---|---|
| Immature DCs | 94 | 56 | 21 | ND[1] |
| DCs matured by LPS | 316 | 71 | 40 | ND |
| DCs matured by TNF-α | 475 | 107 | 96 | ND |
| DCs matured by IFN-γ + TNF-α | 749 | 137 | 149 | 67 |
| T2 cells | 577 | 1214 | 155 | 50 |

ND[1] = not done
Phenotypic analysis of culture derived mDC or T2 antigen-presenting cells. Immature DCs are generated in vitro from CD14+ monocytes of HLA-A2.1+ normal donors by incubation with GM-CSF and IL-4 for 10 days in liquid culture. Immature DCs are induced to undergo maturation by the addition of LPS, TNF-α or TNF-α + IFN-γ during the last three days of culture. Results are expressed as the mean channel fluorescence (MCF) for each antigen tested. Dendritic cells matured with TNF-α + IFN-γ display the highest levels of HLA-A2.1, CD80, and CD86 expression compared to LPS or TNF-α treated dendritic cell cultures. The T2 cell line had the highest level of CD80 expression and similar levels of HLA-A2.1 and CD86 expression to the TNF-α + IFN-γ dendritic cells.

Cytolytic Activity by CD19 or CD20 Peptide-Specific CTLs

CD19 or CD20 peptide-specific CTLs are generated by repeated stimulation of T-lymphocytes from healthy HLA-A2.1+ donors with peptide-pulsed autologous mDC. CTLs are harvested one week after the respective peptide stimulation and examined for their cytolytic activity against the ST486 lymphoma cell line.

Autologous mDCs or T2 cells as antigen presenting cells are also evaluated to induce peptide-specific CTLs. T-lymphocytes from healthy HLA-A2.1+ donors are stimulated with either autologous mDC or T2 cells pulsed with the HLA-A2.1-specific peptide. The CTLs are harvested one week after the second, third or fourth stimulation and analyzed for their cytotoxic activities against the ST486 cell line. Generally, generating CTLs with a minimum of three cycles of stimulation with peptide-pulsed mDCs to obtain highly effective CD19 or CD20 peptide-specific CTLs is preferred. In further experimentation, the possibility of the inhibition of normal cells expressing low levels of CD19 or CD20 antigen by the CD19 or CD20 peptide-specific CTLs is examined. CTLs are generated as previously described using mDCs or T2 cells and examined a week after the first, second, third or fourth stimulation.

Lymphoma-Specific Cell Lysis

Lymphoma-specific cell lysis by CD19 or CD20 peptide-specific CTLs is confirmed using a cold target inhibition assay. In this assay, CTLs are pre-incubation with "cold" ST486 cells for 1 hour before the addition of $^{51}$Cr-labeled ("hot") ST486 target cells. B cell lymphoma-specific cytotoxicity by CD19 or CD20 peptide-specific CTLs is confirmed using the cold target inhibition assay.

IFN-γ Elisa

Figure 6:
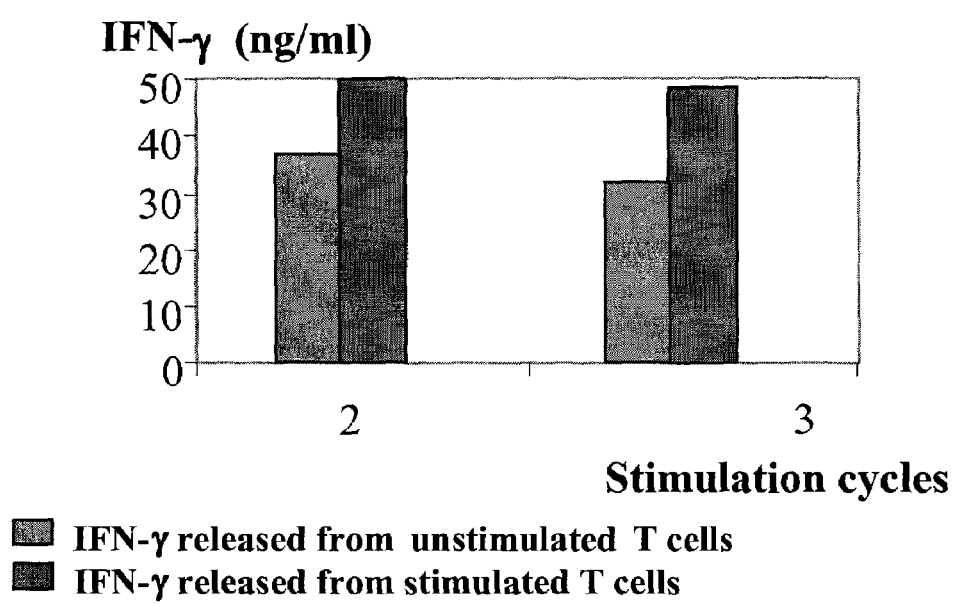
FIG. 6 shows the IFN-γ released by CD20 peptide specific cytotoxic T-lymphocytes to ST486 compared against unstimulated cytotoxic T-lymphocytes.

The secretion of cytokines by antigen-specific T cells helps determine their effector cell function. IFN-γ secretion by antigen-specific T cells has been shown to contribute to host defense by initiating a potent local inflammatory response. Generally, IFN-γ secretion serves as an important cytokine against tumor progression by orienting T lymphocytes into the Th1-subtype (Ikeda H et al., *Cytokine Growth Factor Rev*, 13:95-109 (2002); Beatty G L et al., *Immunol Res*, 24:201-210 (2001)). The CD20 peptide-specific CTLs are evaluated for secretion of IFN-γ as a way to analyze their potential anti-cancer activity based on the Th1 cell subtype. Supernatants from HLA-A2.1+ peptide-specific CTL cultures are analyzed for IFN-γ production after repeated stimulation with the peptide. The production of IFN-γ by the peptide-specific CTL cultures are shown in FIG. 6. IFN-γ production by CD19 peptide-specific CTLs can be analyzed in a similar manner.

Isotypes of CD19 or CD20 Peptide-Specific CTLs

Phenotypic analysis of the CD19 or CD20 peptide-specific CTLs is performed to determine the expression of antigenic markers including CD8, CD69, CD45RA, CD45RO, and CD28 on the cell surfaces. The phenotypic analysis of CD19 or CD20 peptide specific CTLs is determined by flow cytometry following repeated stimulation of the CTLs with mDCs pulsed with peptide.

Detection of CD19 or CD20 Peptide-Recognizing CTLs by Tetramer Staining

The CTL population recognizing specific peptides is characterized using peptide specific-HLA-A2.1-tetramers. Peptide-HLA-A2.1 tetramers are complexes of four HLA-A2.1 molecules associated with a specific peptide and a fluorochrome (Altman J D et al., *Science*, 274:94-96 (1996)). The complexes bind to a distinct set of T cell receptors on a subset of CD8+ T cells that recognize the specific peptide. CTLs recognizing the peptides are identified by staining with peptide-HLA-A2.1-tetramers-PE and CD8-FITC antibodies.

Determination of CD19 or CD20 Epitope Specificity to HLA

In this example, the CD19 or CD20 epitope specific to HLA-A2.1 is examined. This particular epitope was examined as this is the most dominant HLA class I molecule, representing approximately 50% of North American Caucasians, 34% of African-Americans, and 55% of Asian-Americans (Baur M P et al., *Genet Epidemiol*, 6:15-20 (1989)). The identification of the CD19 or CD20 epitope is performed by the evaluation of the amino acid sequence of CD19 or CD20 peptide motifs that are likely to bind to HLA-A2.1.

Dendritic cells (DCs) have been used in the present experiments as an APC because of their unique capacity to activate naïve T cells and initiate primary antigen-specific T cell responses (Steinman A M, *Annu Rev Immunol*, 9:271-296 (1991); Porgador A et al., *J Exp Med*, 182:255-260 (1995); Zitvogel L et al., *J Exp Med*, 183:87-97 (1996)). Presentation of antigens by DCs may be especially important to inducing heightened immune responses to self-antigens since many immunization protocols targeting self-antigens use whole cells and often result in the induction of low-affinity CTL responses (Brossart P et al., *J Exp Med*, 183:2449-2458 (1996); Houbiers J G et al., *Eur J Immunol*, 23:2072-2077 (1993)). In this example, mature dendritic cells are used to present exogeneous peptide sufficiently to T cells to evoke the peptide-specific CTLs. Optimal maturation factors for DCs are also examined.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references disclosed herein, including those cited hereafter, are specifically incorporated herein by reference thereto.

While preferred embodiments have been illustrated and described, it should be understood that changes and modifications can be made therein in accordance with ordinary skill in the art without departing from the invention in its broader aspects as defined in the following claims.

What is claimed is:

1. An isolated leukemic antigen consisting of the peptide KLMSPKLYV (SEQ ID NO: 4) or a variant thereof having one or two conservative or non-conservative amino acid substitutions that is capable of stimulating a cytotoxic T-lymphocyte reaction against a cell expressing CD19.

2. The isolated leukemic antigen of claim 1 consisting of the peptide KLMSPKLYV (SEQ ID NO: 4).

3. A pharmaceutical composition comprising the isolated leukemic antigen of claim 1 and a pharmaceutically acceptable carrier.

4. The pharmaceutical composition of claim 3 further comprising one or more co-immunostimulatory molecules.

* * * * *